US012331315B2

(12) United States Patent
Meng et al.

(10) Patent No.: US 12,331,315 B2
(45) Date of Patent: Jun. 17, 2025

(54) CHIMERIC ANTIGEN RECEPTOR

(71) Applicant: Kite Pharma, Inc., Santa Monica, CA (US)

(72) Inventors: Kevin P. Meng, Gaithersburg, MD (US); Jodi Murakami, Culver City, CA (US); Samuel T. Haile, Castro Valley, CA (US); Edward H. Liao, Petaluma, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 0 days.

(21) Appl. No.: 17/751,266

(22) Filed: May 23, 2022

(65) Prior Publication Data

US 2023/0013874 A1 Jan. 19, 2023

Related U.S. Application Data

(60) Provisional application No. 63/192,296, filed on May 24, 2021.

(51) Int. Cl.
| | |
|---|---|
| *A61K 35/17* | (2025.01) |
| *A61K 40/11* | (2025.01) |
| *A61K 40/31* | (2025.01) |
| *A61K 40/32* | (2025.01) |
| *A61K 40/42* | (2025.01) |
| *A61K 40/46* | (2025.01) |
| *A61P 35/00* | (2006.01) |
| *C07K 14/725* | (2006.01) |
| *C12N 5/0783* | (2010.01) |
| *C12N 15/85* | (2006.01) |
| *A61K 39/00* | (2006.01) |

(52) U.S. Cl.
CPC ............ *C12N 5/0636* (2013.01); *A61K 40/11* (2025.01); *A61K 40/31* (2025.01); *A61K 40/32* (2025.01); *A61K 40/4224* (2025.01); *A61K 40/46* (2025.01); *A61P 35/00* (2018.01); *C07K 14/7051* (2013.01); *C12N 15/85* (2013.01); *A61K 2039/505* (2013.01); *A61K 2239/38* (2023.05); *A61K 2239/59* (2023.05); *C07K 2317/53* (2013.01); *C07K 2319/02* (2013.01); *C07K 2319/03* (2013.01); *C12N 2510/00* (2013.01)

(58) Field of Classification Search
CPC ............... A61K 35/17; A61K 39/0011; A61K 2039/505; A61K 2039/5158; A61K 39/001129; A61K 40/11; A61K 40/31; A61K 40/32; A61K 40/4224; A61P 35/00; C07K 14/7051; C07K 2317/53; C07K 2319/03; C12N 5/0636; C12N 15/85

See application file for complete search history.

(56) References Cited

U.S. PATENT DOCUMENTS

| | | | | |
|---|---|---|---|---|
| 2016/0272718 A1* | 9/2016 | Wang | ............. | A61K 39/464424 |
| 2018/0230193 A1* | 8/2018 | Loew | ............. | C07K 16/30 |
| 2018/0369285 A1* | 12/2018 | Dai | ............. | C12N 15/625 |
| 2020/0131244 A1* | 4/2020 | Leong | ............. | A61P 35/00 |
| 2021/0363218 A1* | 11/2021 | Fan | ............. | A61K 35/17 |

FOREIGN PATENT DOCUMENTS

| | | | | |
|---|---|---|---|---|
| CN | 111995688 A | 11/2020 | | |
| CN | 110724199 B | 12/2023 | | |
| WO | WO-2017027392 A1 * | 2/2017 | ......... | C07K 14/7051 |
| WO | WO-2018/183385 A1 | 10/2018 | | |
| WO | WO-2020/005837 A1 | 1/2020 | | |
| WO | WO-2020/068702 A1 | 4/2020 | | |
| WO | WO-2021/045692 A1 | 3/2021 | | |
| WO | WO-2021045693 A1 | 3/2021 | | |

OTHER PUBLICATIONS

Intl. Search Report—Written Opinion dated Dec. 23, 2022 for Intl. Appl. No. PCT/US2022/030557.
Office Action dated Sep. 11, 2023 for Taiwanese Appl. No. 111119272.
Garber, K. (2018) "Driving T-cell immunotherapy to solid tumors" Nature Biotechnology 36:215-219.
Office Action dated Jun. 24, 2024 for Taiwanese Appl. No. 111119272.
Examination Report dated Sep. 11, 2024 for Australian Appl. No. 2022282266.
Examination Report dated Sep. 13, 2024 for Australian Appl. No. 2022282266.
Office Action dated Sep. 23, 2024 for Israeli Appl. No. 308696.
Office Action dated Jan. 7, 2025 for Japanese Appl. No. 2023-572609.
Bettini M. et al. (2017) "Cutting Edge: CD3 Itam Diversity is Required for Optimal TCR Signaling and Thymocyte Development" The Journal of Immunology 199:1555-1560.
Kusmartsev, S. et al. (2017) "Development of human NKG2D-CD3E chimeric antigen receptor (CAR) for T-cell-mediated cancer immunotherapy" Journal of Clinical Oncology 35:Abstract150.
Wu, W. et al. (2020) "Multiple Signaling Roles of CD38 and Its Application in CAR-T Cell Therapy" Cell 182:855-871.

* cited by examiner

*Primary Examiner* — Jeremy C Flinders
*Assistant Examiner* — Masudur Rahman

(57) ABSTRACT

Provided are chimeric antigen receptors (CARs) comprising an NGK2D ecto domain. Provided are compositions, cells and cell therapies comprising the same. Further provided are methods of treatment.

7 Claims, No Drawings

Specification includes a Sequence Listing.

CHIMERIC ANTIGEN RECEPTOR

CROSS-REFERENCES TO RELATED APPLICATIONS

This application claims the benefit of priority to U.S. Provisional Patent Application No. 63/192,296, filed 24 May 2021 and titled "Chimeric Antigen Receptor," the entirety of which is incorporated by reference herein.

SEQUENCE LISTING

The instant application contains a Sequence Listing which has been submitted electronically in ASCII format and is hereby incorporated by reference in its entirety. Said ASCII copy, created on Jul. 13, 2022, is named K-1106-WO-PCT_SL.txt and is 91,720 bytes in size.

TECHNICAL FIELD

The present disclosure relates to the field of cell therapy, and more specifically, NKG2D chimeric antigen receptors.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen. However, some tumor types, and in particular solid tumors, are resistant to T cell immunotherapy, and a need for development of next-generation enhancement strategies to target tumor intrinsic resistance mechanisms to T cell immunotherapy. NKG2D ligands are expressed on most types of tumors, and they demonstrate relative selectivity of ligand expression on tumor cells compared with healthy cells and represent a target to augment traditional T cell therapies.

SUMMARY

Disclosed is a chimeric antigen receptor (CAR), comprising a NKG2D ecto domain; a transmembrane domain; a 4-1BB costimulatory domain; and a signaling domain comprising a CD3-zeta signaling domain. In embodiments, the 4-1BB costimulatory domain comprises the amino acid sequence according to SEQ ID NO: 33. In embodiments, the CD3zeta signaling domain comprises the amino acid sequence according to SEQ ID NO: 27. In embodiments, the CAR further comprises a CD8-alpha hinge domain. In embodiments, the CD8-alpha hinge domain comprises the amino acid sequence according to SEQ ID NO: 15. In embodiments, the NKG2D ecto domain comprises the amino acid sequence according to SEQ ID NO: 3. In embodiments, the transmembrane domain comprises a CD28 transmembrane domain. In embodiments, the CD28 transmembrane domain comprises the amino acid sequence according to SEQ ID NO: 21. In embodiments, the signaling domain further comprises a CD3-epsilon signaling domain. In embodiments, the CD3-epsilon signaling domain comprises the amino acid sequence according to SEQ ID NO: 31.

Disclosed is a nucleic acid encoding a disclosed CAR and a vector comprising the same. In embodiments, the recombinant vector or nucleic acid further comprises a nucleic acid encoding an engineered T cell receptor (TCR) specific for a tumor antigen. In embodiments, the recombinant vector or nucleic acid further comprises a nucleic acid encoding a second CAR that is specific for a tumor antigen. In embodiments, the tumor antigen comprises HPV-16 E6, HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, CS1. EGFR, EGFR family including ErbB2 (HERII), EGFRvIII, EGP2, EGP40, EPCAM, EphA2, EpCAM, Flt3, FAP, fetal AchR, FRa, GD2, GD3, Glypican-3 (GPC3), HLA-A1+MAGEI, HLA-A2+MAGE1, HLAA3+MAGE1, HLA-A1+NY-ES0-1, HLA-A2+NY-ES0-1, HLA-A3+NY-ES0-1, IL-11Rα, IL-13Rα2, Lambda, Lewis-Y, Kappa, Mesothelin, Muc1, Muc16, NCAM, NKG2D Ligands, NYE-S0-1, PRAME, PSCA, PSMA, RORI, SSX, Survivin, TACI, TAG72, TEMs, or VEGFRII.

Disclosed is a host cell transformed with a disclosed nucleic acid or recombinant vector. In embodiments, a host cell is transformed with disclosed nucleic acid or recombinant vector and a nucleic acid or recombinant vector encoding an engineered T cell receptor (TCR) that is specific for a tumor antigen or a second CAR that is specific for a tumor antigen. In embodiments, the tumor antigen comprises HPV-16 E6, HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, CS1, EGFR, EGFR family including ErbB2 (HERII), EGFRvIII, EGP2, EGP40, EPCAM, EphA2, EpCAM, FAP, fetal AchR, FRa, Flt3, GD2, GD3, Glypican-3 (GPC3), HLA-A1+MAGEI, HLA-A2+MAGE1, HLAA3+MAGE1, HLA-A1+NY-ES0-1, HLA-A2+NY-ES0-1, HLA-A3+NY-ES0-1, IL-11Rα, IL-13Rα2, Lambda, Lewis-Y, Kappa, Mesothelin, Muc1, Muc16, NCAM, NKG2D Ligands, NYE-S0-1, PRAME, PSCA, PSMA, RORI, SSX, Survivin, TACI, TAG72, TEMs, or VEGFRII. In embodiments, the host cell comprises an induced pluripotent stem cell (iPSC), a T cell, or a NK cell. Disclosed is a pharmaceutical composition comprising a disclosed T cell and/or an NK cell. Disclosed is a method of treating disease in a patient in need of thereof, comprising administering a disclosed T cell and/or an NK cell, or the pharmaceutical composition to the patient. In embodiments, the host cell is allogeneic to the patient.

DETAILED DESCRIPTION OF THE INVENTION

Terms

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systeme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, such as a modified T cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the $C_H2$ domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof, and human heavy-chain antibodies (UniAbs)), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Trans-Bodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," "antigen binding fragment," or "antibody fragment"

or "antigen binding domain" refers to any molecule that comprises the antigen binding parts of the molecule. In an example an antigen binding molecule is an antibody, or portion thereof, such as an scFv. In an example an antigen biding molecule is a portion of a TCR that binds antigen, and may be the antigen binding portion of the TCR alpha chain and/or the antigen binding portion of a TCR alpha chain. In an example, an antigen biding molecule may be a portion of NKG2D that binds an NKG2D ligand. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In embodiments, an antigen binding molecule is a chimeric antigen receptor (CAR) or an engineered T cell receptor (TCR). In certain embodiments, the antigen binding molecule or domain is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule or domain comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| | CDR Numbering | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. A "target" is any molecule bound by a binding motif, CAR, TCR or antigen binding agent, e.g., an antibody.

"Antigen-specific targeting region" (ASTR) refers to the region of the CAR or TCR which targets specific antigens. The targeting regions on the CAR or TCR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, such as NKG2D, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular binding pair, such as an antibody-antigen interaction, or the dissociation rate constant of a binding pair, such as an antibody or antibody-binding fragment. Said value is also referred to as the $k_{off}$ value.

The term "$k_a$" (M-1×sec-1 or 1/M) refers to the association rate constant of a particular binding pair, such as antibody-antigen interaction, or the association rate constant of a particular binding pair, such as an antibody or antibody-binding fragment.

The term "$K_A$" (M-1 or 1/M) refers to the association equilibrium constant of a particular binding pair, such as antibody-antigen interaction, or the association equilibrium constant of a binding pair, such as an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding domain, antibody, or antigen binding system with a target of the binding domain, antibody, or antigen binding system as compared to association of the binding domain, antibody, or antigen binding system with an entity that is not the target (i.e. non-target). In some embodiments, a binding domain, antibody, or antigen binding system selectively binds a target if binding between the binding domain, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding domain, antibody, or antigen binding system and a non-target. In some embodiments, a binding domain, antibody, or antigen binding system selectively binds a target if the binding affinity is less than about $10^{-5}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$.

In certain embodiments, provided herein is an antibody or an antigen binding molecule thereof that binds to the target human antigen with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. In some embodiments, the methods of the present disclosure can be used to reduce the tumor size of a tumor derived from, for example, prostate cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, multiple myeloma, and combinations of said cancers. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1α), MIP-1β (MIP-1b), gamma-induced protein 10 (IP-10), and thymus and activation regulated chemokine (TARC or CCL17).

"Chimeric antigen receptor" or "CAR" refers to a molecule engineered to comprise a binding domain and a means of activating immune cells (for example T cells such as naive T cells, central memory T cells, effector memory T cells, NK cells or combination thereof) upon antigen binding. CARs are also known as artificial T cell receptors, chimeric T cell receptors or chimeric immunoreceptors. In some embodiments, a CAR comprises a binding domain, an extracellular domain, a transmembrane domain, one or more co-stimulatory domains, and an intracellular signaling domain. A T cell that has been genetically engineered to express a chimeric antigen receptor may be referred to as a CAR T cell. Similarly, an NK cell that has been genetically engineered to express a chimeric antigen receptor may be referred to as a CAR NK cell.

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition.

"Extracellular domain" (or "ECD") refers to a portion of a polypeptide that, when the polypeptide is present in a cell membrane, is understood to reside outside of the cell membrane, in the extracellular space. Ecto domain may be used herein interchangeably with extracellular domain.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region, such as an Igg4 hinge. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, NKG2D, 2B4 and CD154. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling domains which are known as immunoreceptor tyrosine-based activation domain or ITAMs.

Examples of ITAM containing primary cytoplasmic signaling sequences that are of particular use in the disclosure include those derived from DAP10, DAP12, TCRzeta, FcRgamma, FcRbeta, CD3zeta, CD3gamma, CD3delta, CD3epsilon, CD5, CD22, CD79a, CD79b and CD66d.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), OX40 (CD134), CD30, CD40, PD-1, ICOS (CD278), LFA-1, CD2, CD7, LIGHT, NKD2C, 2B4, CD137, DAP12, B7-H2 and a ligand that specifically binds CD83. Accordingly, while the present disclosure provides exemplary costimulatory domains derived from CD28, CD3-epsilon, 4-1BB, other costimulatory domains are contemplated for use with the CARs described herein. The inclusion of one or more co stimulatory signaling domains may enhance the efficacy and expansion of T cells and NK cells expressing CAR receptors. The intracellular signaling and costimulatory signaling domains may be linked in any order in tandem to the carboxyl terminus of the transmembrane domain.

Although CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from 4-1BB, CD28, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137: 3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence domain, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells or NK cells can be engineered to express, for example, chimeric antigen receptors (CAR) and/or T cell receptor (TCR). In some examples, CAR positive (+) T or NK cells are engineered to express an extracellular single chain variable fragment (scFv) with specificity for a particular tumor antigen linked to an intracellular signaling part comprising at least one costimulatory domain and at least one activating domain. In some examples, CAR positive (+) T or NK cells are engineered to express an extracellular domain of NKG2D, with specificity for NKG2D antigens, linked to an intracellular signaling part comprising at least one costimulatory domain and at least one activating domain. The costimulatory domain can be derived from a naturally-occurring costimulatory domain, or a variant thereof, e.g., a variant having a truncated hinge domain ("THD"), and the activating domain can be derived from, e.g., CD3-zeta and/or CD3-epsilon. In certain embodiments, the CAR is designed to have two, three, four, or more costimulatory domains.

In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, which are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g. without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man. In embodiments, a CAR is a fusion protein. In embodiments, a TCR is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or NK cell, which can either be obtained from a patient or a donor. In some embodiments, the cell that is modified is an induced pluripotent stem cell (iPSC) which can be differentiated to a lymphocyte, such as a T cell or NK cell. The cell can be modified to express an exogenous construct, such as, e.g., a chimeric antigen receptor (CAR) or a T cell receptor (TCR), which is incorporated into the cell's genome. Other gene edits can also be done, for example to reduce rejection and/or enhance cell fitness. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell or NK cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, α, β, γ, and δ, may rearrange leading to highly diverse TCR proteins. Examples of TCR based T cell therapies are disclosed in International Patent Application Nos. PCT/US2013/059608 and PCT/US2015/033129, which are hereby incorporated herein by reference in their entirety.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, NK cells and T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035. Examples of TCR based T cell therapies are disclosed in International Patent Application Nos. PCT/US2013/059608 and PCT/US2015/033129, which are hereby incorporated herein by reference in their entirety.

The T cells or NK cells of the immunotherapy can come from any source known in the art. For example, T cells and NK cells can be differentiated in vitro from a hematopoietic stem cell population (for example iPSCs) or can be obtained from a subject. T cells and NK cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell or an NK cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a CAR, TCR, and/or scFv, or ever one of more of those polypeptides together. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ domain (SEQ ID NO: 2), which results in cleavage between the 2A glycine and the 2B proline. Other linkers will be apparent to those of skill in the art and may be used in connection with this disclosure. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR or TCR. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide. In another example it may be used to connect to or more polypeptides to be expressed, such as a CAR and/or TCR.

Other linkers include non-cleavable linkers. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues.

The term "lymphocyte" includes natural killer (NK) cells, T cells, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element. In embodiments, a promotor is operably linked to nucleic acids.

A "patient" includes any human who is afflicted with a cancer (e.g., multiple myeloma). The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "proliferation" refers to an increase in cell division, either symmetric or asymmetric division of cells. In some embodiments, "proliferation" refers to the symmetric or asymmetric division of T cells. "Increased proliferation" occurs when there is an increase in the number of cells in a treated sample compared to cells in a non-treated sample.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+T lymphocytes. However, Treg cells within a tumor microenvironment (i.e. tumor-infiltrating Treg cells), Treg cells may make up as much as 20-30% of the total CD4+T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells or NK cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "transmembrane domain" is a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. A transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, Techniques for the Analysis of Complex Genomes, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as Advances in Immunology.

The present disclosure provides antigen receptors (CARs) comprising a portion of the extracellular domain of NKG2D that is capable of binding one or more NKG2D ligands, referred to herein as NKG2D CARs. Among other things, the present disclosure provides methods and compositions useful for treatment of cancer and/or for initiating or modulating immune responses. In some embodiments, the NKG2D CAR is expressed with a TCR specific for one or more tumor antigens and/or one or more additional CARs specific for one or more tumor antigens.

Various embodiments of the present disclosure provide a vector encoding a NKG2D CAR provided herein, e.g., a vector encoding a NKG2D CAR. Various embodiments of the present disclosure provide a vector encoding a TCR or one or more additional CARs (e.g. a CAR that binds a different target than the NKG2D CAR), e.g., a vector encoding a NKG2D CAR and TCR or one or more additional CARs. In some embodiments the NKG2D CAR is encoded in a separate vector from the vector encoding the TCR or one or more additional CARs. In some embodiments the NKG2D CAR is encoded in the same vector encoding the TCR or one or more additional CARs.

Various embodiments of the present disclosure provide a cell encoding or expressing a NKG2D CAR, e.g., induce pluripotent cells (iPSC) a T cell or NK cell engineered to encode or express NKG2D CAR. Various embodiments of the present disclosure provide a cell encoding or expressing a NKG2D CAR and a TCR or one or more additional CARs, e.g., a T cell or NK cell engineered to encode or express a NKG2D CAR and a TCR or one or more additional CARs. The present disclosure provides immune cells genetically modified with an integrated gene, e.g., a nucleotide sequence of interest (e.g., a constitutive expression construct and/or an inducible expression construct that comprises such nucleotide sequence. In embodiments, the immune cells are further engineered to express a TCR or one or more additional CARs. In some embodiments, the present disclosure provides methods of treating a subject having a tumor, comprising administering to the subject a NKG2D CAR therapy described herein. In some embodiments, methods further comprise administration of one or more additional therapies (e.g., a second binding agent (e.g., CAR T cell, CAR-NK cell, TCR-T cell, TIL cell, allogeneic NK cell, and autologous NK cell), an antibody-drug conjugate, an antibody, a bispecific antibody, a T cell-engaging bispecific antibody, an engineered antibody, and/or a polypeptide described herein).

Natural killer cells preferentially express several calcium-dependent (C-type) lectins, which have been implicated in the regulation of NK cell function. NKG2D (NCBI Gene ID: 22914 as updated Mar. 7, 2021, which is incorporated herein by reference) is a transmembrane protein belonging to the NKG2 family of C-type lectin-like receptors. The NKG2 gene family is located within the NK complex, a region that contains several C-type lectin genes preferentially expressed in NK cells. NKG2D is a recognition receptor for the detection and elimination of transformed and infected cells as its ligands are induced during cellular stress, either as a result of infection or genomic stress such as in cancer. NKG2D binds to a diverse family of ligands that include MHC class I chain-related A and B proteins and UL-16 binding proteins. The surface expression of these ligands is important for the recognition of stressed cells by the immune system, and thus this protein and its ligands are therapeutic targets for the treatment of immune diseases and cancers.

NKG2D ligands are induced-self proteins which are absent or present only at low levels on surface of normal cells but are overexpressed by infected, transformed, senescent and stressed cells. Their expression is regulated at different stages (transcription, mRNA and protein stabilization, cleavage from the cell surface) by various stress pathways. The NKG2D ligands are homologous to MHC class I molecules and are divided into two families: MIC and RAET1/ULBP. Human MIC genes are located within the MHC locus and are composed of seven members (MICA-G), of which only MICA and MICB produce functional transcripts. Among ten known human RAET1/ULBP genes, six encode functional proteins: RAET1E/ULBP4, RAET1G/ULBP5, RAET1H/ULBP2, RAET1/ULBP1, RAET1L/ULBP6, RAET1N/ULBP3.

Chimeric antigen receptors (CARs) are engineered receptors that may direct or redirect T cells or NK cells (e.g., patient or donor T or NK cells) to a selected target. A CAR may be engineered to recognize a target (such as an antigen and in the case of a disclosed NKG2D CAR a NKG2D ligand) and, when bound to that target, activate the immune cell to attack and destroy the cell bearing that target. When these targets exist on tumor cells, an immune cell that expresses the CAR may target and kill the tumor cell. CARs generally comprise an extracellular binding domain that mediates antigen binding (e.g., a NKG2D ecto domain), a transmembrane domain that spans, or is understood to span, the cell membrane when the CAR is present at a cell surface or cell membrane, and an intracellular (or cytoplasmic) signaling domain.

According to at least one non-limiting view, there have been at least three "generations" of CAR compositions. In a first generation of CARs, a binding domain (e.g., a single chain fragment variable, binding domain) is linked or connected to a signaling domain (e.g., CD3) via a transmembrane domain, optionally comprising a hinge domain and one or more spacers. In a second generation of CARs, a costimulatory domain (CM1, such as CD28, 4-1BB, or OX-40) is introduced with the signaling domain (e.g., CD3). In a third generation of CARs, a second costimulatory domain (CM2) is comprised.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TM and CD28 and CD3ζ signaling modules).

A NKG2D CAR of the present disclosure may comprise an extracellular NKG2D domain that binds NKG2D ligands. In some embodiments, an antigen binding system further comprises a costimulatory domain, and/or an extracellular domain (e.g., a "hinge" or "spacer" region), and/or a transmembrane domain, and/or an intracellular (signaling) domain, a CD3-zeta and/or CD3-epsilon activation domain.

In certain embodiments, a NKG2D CAR comprises a NKG2D ecto domain (extracellular domain) polypeptide refers to a polypeptide which has at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID 3. LFNQEVQIPLTESYCGPCPKNWICYKNN-CYQFFDESKNWYESQASCMSQNASLLKVYS KEDQDLLKLVKSYHWMGLVHIPTNGSWQWEDGSIL-SPNLLTIIEMQKGDCALYASSFK GYIENCSTPN-TYICMQRTV (SEQ ID NO: 3). In embodiments, a NKG2D ecto domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to TTATT-CAACCAAGAAGTCCAGATTCCCTTGACCGAAAGT-TACTGCGGCCCATGTCCG AAAAACTGGATATGT-TATAAAAATAACTGTTACCAGTTCTTCGATGAATCT AAAAA CTGGTATGAGAGCCAGG-CATCTTGTATGTCTCAAAATGCCAGCCTGCT-CAAAGTATA CAGCAAGGAGGACCAGGATTTACT-TAAACTGGTGAAGTCATATCACTGGATGGGAT TGGTACACATTCCCACAAATGGATCTTGGCAGTGG-GAAGACGGCTCCATTCTCTCAC CCAACC-TACTAACAATAATTGAAATGCAGAAGGGA-GACTGCGCACTCTATGCATCG AGCTTTAAAGGTTATATAGAAAACTGTTCAACTC-CAAATACATACATCTGCATGCAA AGGACTGTA (SEQ ID NO: 4). In embodiments, a NKG2D ecto domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to TTATTCAAC-CAAGAAGTCCAAATTCCCTTGACCGAAAGT-TACTGTGGCCCATGTCCT AAAAACTGGATATGTTA-CAAAAATAACTGTTACCAATTCTTCGATGAAAGTA AAAA CTGGTATGAGAGCCAGGCTTCTTGTATGTCT-CAAAATGCCAGCCTTCTGAAAGTATA CAGCAAGGAGGACCAGGATTTACTTAAACTGGT-GAAGTCATATCATTGGATGGGAC TAGTACACATTC-CAACAAATGGATCTTGGCAGTGGGAAGACGGCTC-CATTCTCTCAC CCAACCTACTAACAATAATTGAAATGCAGAAGGGA-GACTGTGCACTCTATGCATCG AGCTTTAAAGGC-TATATAGAAAACTGTTCAACTCCAAATACATA-CATCTGCATGCA AAGGACTGTG (SEQ ID NO: 5). In embodiments, a NKG2D ecto domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to

```
                                     (SEQ ID NO: 55)
TTATTCAACCAAGAAGTCCAAATTCCCTTGACCGAAAGTTACTGTGG

CCCATGTCCTAAGAACTGGATATGTTACAAAAATAACTGTTACCAAT

TCTTCGATGAATCTAAGAATTGGTATGAGAGCCAGGCTTCTTGTATG

TCTCAAAATGCCAGCCTTCTTAAAGTATACAGCAAAGAGGACCAGGA

TTTACTTAAACTGGTGAAGTCATATCATTGGATGGGACTAGTACACA

TTCCAACAAATGGATCTTGGCAGTGGGAAGACGGCTCCATTCTCTCA

CCCAACCTACTAACAATAATTGAAATGCAGAAGGGAGACTGTGCACT

CTATGCATCGAGCTTTAAAGGCTATATAGAAAACTGTTCAACTCCAA

ATACATATATTTGCATGCAAAG GACTGTG.
```

In some embodiments, a NKG2D CAR of the present disclosure may comprise an antigen binding system that comprises one or more, or all, of a leader peptide (P), NKG2D ecto domain (B), a hinge (E), a transmembrane domain (T), a costimulatory domain (C), a second costimulatory domain (C'), and an activation domain (A). In some instances, a NKG2D CAR is configured according to the following: B E T A. In certain instances, the activation domain comprises one or more activation domains. In certain aspects, the activation domain comprises CD3ζ, CD3ε, or both CD3ζ and CD3ε. In some instances, a NKG2D CAR is configured according to the following: PB ET A. In some instances, a NKG2D CAR is configured according to the following: B E T C A. In some instances a NKG2D CAR is configured according to the following: PB ET C A. In some instances, a NKG2D CAR is configured according to the following: B E T C C' A. In some instances, a NKG2D CAR is configured according to the following: P B E T C C' A.

In certain embodiments, the CARs contemplated herein may comprise linker residues between the various domains, domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers $(G_{1-5}S_{1-5})n$ (SEQ ID NO: 78), where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, Rev. Computational Chem. 11173-142 (1992)). Other linkers contemplated herein include Whitlow linkers (see Whitlow, Protein Eng. 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker (SEQ ID NO: 6). In another embodiment, any of the constructs described herein comprise a "GSG" linker. In an example a glycine-serine linker comprises or consists of the amino acid sequence GS (SEQ ID NO: 6), which may be encoded by the nucleic acid sequence according to ggatcc (SEQ ID NO: 7) or gggtcc (SEQ ID NO: 8). In an example a glycine-serine linker comprises or consists of the amino acid sequence GGGSGGGS (SEQ ID NO: 9), which may be encoded by the nucleic acid sequence according to ggcggtggaagcggaggaggttcc (SEQ ID NO: 10). In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 11 (GSTSGSGKPGSGEGSTKG (SEQ ID NO: 11). In an embodiment, a linker is encoded by a nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid sequence according to

```
                                     (SEQ ID NO: 12)
gggagcactagcggctctggcaaacctggatctggcgagggatctacc aagggc,
                                     (SEQ ID NO: 13)
gggagcacaagcggctctggcaaacctggatctggcgagggatctacc aagggc,
or
                                     (SEQ ID NO: 14)
gggagcacaagcggctctggcaaacctggatccggcgagggatctacc aagggc.
```

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

In some embodiments, the CARs contemplated herein re may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof. A hinge may be derived from a natural source or from a synthetic source. Hinge domains suitable for use in the CARs described herein include the hinge region derived from the extracellular regions of type 1 membrane proteins such as CD8a, CD4, CD28 and CD7, which may be wild-type hinge regions from these molecules or may be altered. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof.

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In embodiments, the hinge domain comprises a CD8a hinge region. In embodiments the CARs described herein comprise a hinge domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15 (TTTPAPRPPT-PAPTIASQPLSLRPEACRPAAGGAVHTRGLDFACD (SEQ ID NO: 15)). In embodiments, hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: ACCACGACGCCAGCGCCGCGACCAC-CAACACCGGCGCCCACCATCGCGTCGCAACC CCTGTCCCTGCGCCCAGAGGCGTGCCGGCCAGCG GCGGGGGGCGCAGTGCACACGA GGGGGCTGGACTTCGCCTGTGAT (SEQ ID NO: 16). In embodiments, a hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: ACAACGACGCCAGCGCCGCGACCAC-CAACACCGGCGCCCACCATCGCGTCGCAACC CCTGTCCCTGAGGCCT-GAAGCGTGCCGGCCAGCGGCGGGGGCGCAGTGC ACACGA GGGGGCTGGACTTCGCTTGTGAC (SEQ ID NO: 17). In embodiments, hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: ACCACGACGCCAGCGCCGCGACCAC-CAACACCGGCGCCCACCATCGCGTCGCAACC CCTGTCCCTGCGCCCCGAGGCGTGCCGGCCAGCG GCGGGGGGCGCAGTGCACACGA GGGGGCTGGACTTCGCCTGTGAT (SEQ ID NO: 18). In embodiments, hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 56)
ACCACGACGCCAGCGCCGCGACCACCAACACCGGCGCCCACCATCGCG

TCGCAACCCCTGTCCCTGAGGCCTGAAGCGTGCCGGCCAGCGGCGGGC

GGCGCAGTGCACACGAGAGGGCTGGACTTCGCCTGTGAT.

In embodiments, the hinge domain comprises a truncated CD28 hinge region (CD28T) hinge region, such as disclosed in International Patent Application No: PCT/US2017/025351, filed Mar. 31, 2017, which is incorporated herein by reference in its entirety. In embodiments the CARs described herein comprise a CD28T hinge domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 19 (LD-NEKSNGTIIHVKGKHLCPSPLFPGPSKP (SEQ ID NO: 19)). In embodiments, a CD28T hinge domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 20)
CTAGACAATGAGAAGAGCAATGGAACCATTATCCATGTGAAAGGGAAA

CACCTTTGTCCAAGTCCCCTATTTCCCGGACCTTCTAAGCCC.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding domain and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, 2B4, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRT AM, cytokine receptor, DAP-10, DAP-12, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

In embodiments a NKG2D CAR described herein comprise a TM domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 21 (FWVLVVVGGV-LACYSLLVTVAFIIFWV (SEQ ID NO: 21)). In embodiments, TM domain from CD28 is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: TTTTGGGTGCTGGTGGTGGTTGGTG-GAGTCCTGGCTTGCTATAGCTTGCTAGTAACA GTGGCCTTTATTATTTTCTGGGTG (SEQ ID NO: 22). In embodiments, TM domain from CD28 is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: TTTTGGGTAT-TGGTAGTAGTGGGCGGAGTCCTGGCTTGC-TATAGTCTGCTAGTAACA GTGGCTTTTATTATAT-TTTGGGTG (SEQ ID NO: 23). In embodiments, TM domain from CD28 is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 24)
TTTTGGGTGCTGGTGGTGGTTGGTGGAGTCCTGGCTTGCTATAGCTT

GCTAGTAACAGTGGCCTTTATTATTTTCTGGGTG.

In embodiments the CARs described herein comprise a TM domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 25(IYIWAPLAGTCGVLLLSLVITLYC (SEQ ID NO: 25)). In embodiments, TM domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: ATCTACATCTGGGCGCCCTTGGCCGGGACTTGTGGGGTCCTTCTCCTGTCACTGGTT ATCACCCTTTATTGC (SEQ ID NO: 26). In embodiments, TM domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 57)
ATCTACATCTGGGCGCCCTTGGCCGGGACTTGTGGGGTCCTTCTCCTGT

CACTGGTTATCACCCTTTACTGC.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation domain (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

Illustrative examples of ITAM containing primary signaling domains that are useful in the present disclosure include those derived from TCRζ, FcRγ, FcRβ, DAP12, CD3γ, CD3δ, CD3ε, CD3ζ, CD22, CD79a, CD79b, and CD66d. In some embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain. In one embodiment, the CARs have a CD3ζ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 27. LRVKFSRSADAPAYQQGQNQLYNELNLGR-REEYDVLDKRRGRDPEMGGKPRRKNPQE GLY-NELQKDKMAEAYSEIGMKGERRRGKGHDGLYQGL-STATKDTYDALHMQALPPR (SEQ ID NO: 27). In embodiments, a CD3ζ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: CTGAGAGTGAAGTTCAGCAG-GAGCGCA-GACGCCCCGCGTACCAGCAGGGGCAGA ACCAACTCTATAACGAGCTCAATCTAG-GAAGGAGAGAAGAGTACGATGTTCTAGAC AAGA-GACGTGGCCGGGACCCTGAGATGGGGGGAAAGC-CACGAAGGAAGAACCCTC AGGAAGGCCTGTACAACGAACTACAAAAAGA-TAAAATGGCGGAGGCCTACAGTGA GATTGGCAT-GAAAGGCGAGCGCCGGAGGGGCAAGGGGCAC-GATGGCCTTTACCAG GGCCTCAGTACAGCCACCAAGGACACC-TATGACGCCCTTCACATGCAAGCTCTGCC CCCTCGC (SEQ ID NO: 28). In embodiments, a CD3ζ domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 29)
CTGAGAGTGAAGTTCAGCAGGAGCGCAGACGCCCCGCGTACCAGCAGG

GCCAGAACCAGCTCTATAACGAGCTCAATCTAGGACGAAGAGAGGAGTA

CGATGTTTTGGACAAGAGACGTGGCCGGGACCCTGAGATGGGGGAAAG

CCGAGAAGGAAGAACCCTCAGGAAGGCCTGTACAACGAACTGCAGAAAG

ATAAGATGGCGGAGGCCTACAGTGAGATTGGCATGAAAGGCGAGCGCCG

GAGGGGCAAGGGGCACGACGGCCTTTACCAGGGTCTCAGTACAGCCACC

AAGGACACCTACGACGCCCTTCACATGCAGGCCCTGCCCCCTCGC.

In embodiments, a CD3 domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: CTGAGAGTGAAGTTCAGCAG-GAGCGCA-GACGCCCCGCGTACCAGCAGGGCCAGA ACCAGCTCTATAACGAGCT-CAATCTAGGACGAAGAGAGGAGTAC-GATGTTTTGGAC AAGAGGCGTGGCCGGGACCCT-GAGATGGGGGGAAAGCCGAGAAGGAAGAACCCTC AGGAAGGCCTGTACAATGAACTGCAGAAAGATAA-GATGGCGGAGGCCTACAGTGA GATTGGGAT-GAAAGGCGAGCGCCGGAGGGGCAAGGGGCAC-GATGGCCTTTACCAG GGCCTCAGTACAGCCACCAAGGACACC-TACGACGCCCTTCACATGCAGGCCCTGCC CCCTCGC (SEQ ID NO: 30). In embodiments, a CD3ζ domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: CTGAGAGT-GAAGTTCAGCAGGAGCGCA-GACGCCCCGCGTACCAGCAAGGGCAGA ACCAGCTCTATAACGAGCT-CAATCTAGGACGAAGAGAGGAGTAC-GATGTTTTGGAC AAGAGGCGTGGCCGGGACCCT-GAGATGGGGGGAAAGCCGAGAAGGAAGAACCCTC AGGAAGGCCTGTACAATGAACTGCAGAAAGATAA-GATGGCGGAGGCCTACAGTGA GATTGGGAT-GAAAGGCGAGCGCCGGAGGGGCAAGGGGCAC-GATGGCCTTTACCAG GGTCTCAGTACAGCCACCAAGGACACC-TACGACGCCCTTCACATGCAAGCTCTGCC CCCTCGCTGA (SEQ ID NO: 58). In embodiments, a CD3ζ domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: CTGAGAGTTAAGTTCAGCAG-GAGCGCCGACGCCCCTGCC-TACCAGCAAGGACAGAA TCAACTGTA-CAACGAGCTGAACCTGGGCAGACGGGAGGAATAC GATGTGCTGGACA AGAGGAGAGGCAGA-GACCCCGAGATGGGCGGCAAACCTAGAAGAAAG AACCCCCA GGAGGGCCTGTATAACGAGCTCCAGAAGGACAA-GATGGCCGAGGCCTACAGCGAG ATCGGCAT-GAAGGGCGAAAGAAGAAGAGGCAAGGGC-CACGACGGCCTCTACCAGG GCTTAAGCACAGCTACAAAGGACACC-TACGACGCCCTGCACATGCAGGCCCTGCCC CCTAGATGA (SEQ ID NO: 59). In embodiments, a CD3ζ domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 60)
CTGAGAGTGAAGTTCAGCAGGAGCGCAGACGCCCCCGCGTACCAGCAAG

GGCAGAACCAGCTCTATAACGAGCTCAATCTAGGACGAAGAGAGGAGTA

CGATGTTTTGGACAAGAGGCGTGGCCGGGACCCTGAGATGGGGGGAAAG

CCGAGAAGGAAGAACCCTCAGGAAGGCCTGTACAATGAACTGCAGAAAG

ATAAGATGGCGGAGGCCTACAGTGAGATTGGGATGAAAGGCGAGCGCCG

GAGGGGCAAGGGGCACGATGGCCTTTACCAGGGTCTCAGTACAGCCACC

AAGGACACCTACGACGCCCTTCACATGCAAGCTCTGCCCCCTCGCTGA.

In some embodiments, a CAR comprises a CD3ζ signaling domain, a CD3ε signaling domain and one or more costimulatory signaling domains. The intracellular primary signaling and costimulatory signaling domains may be linked in any order in tandem to the carboxyl terminus of the transmembrane domain. In embodiments, the CARs have a CD3ε domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 31. KNRKAKAKPVTRGAGAG-GRQRGQNKERPPPVPNPDYEPIRKGQRDLYSGL (SEQ ID NO: 31). In embodiments, the CARs have a CD3ε domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO:

(SEQ ID NO: 61)
KNRKAKAKPVTRGAGAGGRQRGQNKERPPPVPNPDYEPIRKGQRDLY

SGLNQRRI.

In embodiments, a CD3c domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: AAGAACCGAAAAGCAAAAGC-CAAGCCTGTTACAAGAGGAGCAGGGGCAG-GAGGCC GACAGAGAGGGCAAAACAAAGAAAGGCCCCCGCC CGTCCCAAACCCGGATTATGA GCCAATTAG-GAAGGGTCAGAGAGACCTGTATTCTGGCTC (SEQ ID NO: 32). In embodiments, a CD3c domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 62)
AAGAACCGCAAAGCAAAGGCAAAACCCGTCACACGAGGAGCGGGCGC

AGGGGGACGACAACGCGGTCAGAATAAGGAACGCCCGCCTCCAGTAC

CAAATCCAGATTATGAACCAATTCGGAAGGGACAACGCGATCTCTAC

TCCGGTCTCAATCAGAGGCGAATT.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include DAP-10, DAP-12, CD27, CD28, CD137(4-IBB), OX40 (CD134), CD30, CD40, PD-I, ICOS (CD278), CTLA4, LFA-1, CD2, CD7, LIGHT, TRIM, LCK3, SLAM, DAPIO, LAGS, HVEM, B7-H3, NKD2C, GITR, CD5, ICAM-1, CD11a, Lck, TNFR-I, TNFR-II, FasR, NKG2C, and B7-H3, and CD83.

In embodiments, the CARs comprise a 4-1BB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 33. KRGRKKLLY-IFKQPFMRPVQTTQEEDGCSCRFPEEEEGGCE (SEQ ID NO: 33). In embodiments, the CARs comprise a 4-1BB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: _. KRGRKKLLY-IFKQPFMRPVQTTQEEDGCSCRFPEEEEGGCEL (SEQ ID NO: 63). In embodiments, a 4-IBB costimulatory domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: AAACGAGGCAGAAAGAAACTCCTGTATATATT-CAAACAACCATTTATGAGACCAGT ACAAACAACTCAGGAGGAG-GATGGCTGTAGCTGCCGATTCCCG-GAAGAAGAAGAA GGTGGCTGTGAA (SEQ ID NO: 34). In embodiments, a 4-IBB costimulatory domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: AAACGGGGCAGAAAGAAACTCCTGTATATATT-CAAACAACCATTTATGAGACCAGT ACAAACTACT-CAAGAGGAAGATGGCTGTAGCTGCCGAT-TTCCAGAAGAAGAAGAA GGAGGATGTGAA (SEQ ID NO: 35). In embodiments, a 4-IBB costimulatory domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: AAACGGGGCAGAAAGAAACTCCTGTATATATT-CAAACAACCATTTATGAGACCAGT ACAAACTACT-CAAGAGGAAGATGGCTGTAGCTGCCGAT-TTCCAGAAGAAGAAGAA GGAGGATGTGAA (SEQ ID NO: 36). In embodiments, a 4-IBB costimulatory domain is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 64)
AAGAGAGGCCGGAAGAAGCTGCTGTACATCTTCAAGCAGCCCTTCAT

GAGACCTGTGCAGACCACACAGGAGGAAGACGGCTGCAGCTGTAGAT

TCCCCGAGGAAGAGGAGGGCGGCTGTGAGCTG.

In embodiments, the CARs comprise a CD28 costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 37. RSKRSRLLHSDYMNMT-PRRPGPTRKHYQPYAPPRDFAAYRS (SEQ ID NO: 37). In embodiments, a CD28 costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 38)
AGGAGTAAGAGGAGCAGGCTCCTGCACAGTGACTACATGAACATGACT

CCCCGCCGCCCCGGGCCCACCCGCAAGCATTACCAGCCCTATGCCCCA

CCACGCGACTTCGCAGCCTATCGCTCC.

The engineered NKG2D CARs described herein may also comprise an N-terminal signal peptide or tag at the N-terminus of the NKG2D ecto domain. In one embodiment, a heterologous signal peptide may be used. The antigen binding domain may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly, any known tag sequence known in the art may also be used.

In embodiments, a signal sequence is a CD8a signal sequence. In embodiments, the NKG2D CARs described herein comprise a CD8a signal sequence having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 39; MALPVTALLLPLALLLHAARP (SEQ ID NO: 39). In embodiments, a CD8a signal sequence is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to: ATGGCTCTTCCTGTGACTGCACTACTGCTGCCCCTGGCCTTACTTCTTCATGCTGCGCGTCCT (SEQ ID NO: 40). In embodiments, a CD8a signal sequence is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 65)
ATGGCTCTTCCTGTGACAGCTCTTCTGCTGCCCCTGGCCCTGCTTCT

GCATGCTGCTAGACCT.

In one embodiment a signal sequence is a CSF2RA signal sequence. In embodiments, the NKG2D CARs described herein comprise a CSF2RA signal sequence having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) to MLLLVTSLLLCELPHPAFLLIP (SEQ ID NO: 41), MEWTWVFLFLLSVTAGVHS (SEQ ID NO: 42), or MALPVTALLLPLALLLHAARP (SEQ ID NO: 43). In embodiments, a CSF2RA signal sequence is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 44)
ATGGCTCTTCCTGTGACAGCTCTTCTGCTGCCCCTGGCCCTGCTTCTG

CATGCTGCTAGACCT.

Components of a CAR may be exchanged or "swapped" using routine techniques of biotechnology for equivalent components. To provide just a few non-limiting and partial examples, a CAR of the present disclosure may comprise a binding domain as provided herein in combination with a hinge provided herein and a costimulatory domain provided herein. In certain examples, a CAR of the present disclosure may comprise a leader sequence as provided herein together with a binding domain as provided herein in combination with a hinge provided herein and a costimulatory domain provided herein.

In one embodiment described herein, a NKG2D CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 45. MALPVTALLLPLALLLHAARPLFNQEVQIPLTESYCGPCPKNWICYKNNCYQFFDESKN WYESQASCMSQNASLLKVYSKEDQDLLKLVKSYHWMGLVHIPTNGS WQWEDGSILSP NLLTIIEMQKGDCALYASSFKGYIENCSTPNTYICMQRTVTTTPAPRPPTPAPTIASQPLSL RPEACRPAAGGAVHTRGLDFACDFWVLVVVGGVLACYSLLVTVAFIIFWVKRGRKKL LYIFKQPFMRPVQTTQEEDGCSCRFPEEEEGGCELRV KFSRSADAPAYQQGQNQLYNEL NLGRREEYDVLDKRRGRDPEMGGKPRRKNPQEGLYNELQKDKMAEAYSEIGMKGERR RGKGHDGLYQGLSTATKDTYDALHMQALPPR (SEQ ID NO: 45). In embodiments a NKG2D CAR binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 46)
ATGGCTCTTCCTGTGACTGCACTACTGCTGCCCCTGGCCTTACTTCTTC

ATGCTGCGCGTCCTTTATTCAACCAAGAAGTCCAGATTCCCTTGACCGA

AAGTTACTGCGGCCCATGTCCGAAAAACTGGATATGTTATAAAAATAAC

TGTTACCAGTTCTTCGATGAATCTAAAAACTGGTATGAGAGCCAGGCAT

CTTGTATGTCTCAAAATGCCAGCCTGCTCAAAGTATACAGCAAGGAGGA

CCAGGATTTACTTAAACTGGTGAAGTCATATCACTGGATGGGATTGGTA

CACATTCCCACAAATGGATCTTGGCAGTGGGAAGACGGCTCCATTCTCT

CACCCAACCTACTAACAATAATTGAAATGCAGAAGGGAGACTGCGCACT

CTATGCATCGAGCTTTAAAGGTTATATAGAAACTGTTCAACTCCAAAT

ACATACATCTGCATGCAAAGGACTGTAACAACGACGCCAGCGCCGCGAC

CACCAACACCGGCGCCCACCATCGCGTCGCAACCCCTGTCCCTGAGGCC

TGAAGCGTGCCGGCCAGCGGCGGGGGCGCAGTGCACACGAGGGGCTG

GACTTCGCTTGTGACTTTTGGGTATTGGTAGTAGTGGGCGGAGTCCTGG

CTTGCTATAGTCTGCTAGTAACAGTGGCTTTTATTATATTTTGGGTGAA

ACGAGGCAGAAAGAAACTCCTGTATATATTCAAACAACCATTTATGAGA

CCAGTACAAACAACTCAGGAGGAGGATGGCTGTAGCTGCCGATTCCCGG

AAGAAGAAGAAGGTGGCTGTGAACTGAGAGTGAAGTTCAGCAGGAGCGC

AGACGCCCCGCGTACCAGCAGGGGCAGAACCAACTCTATAACGAGCTC

AATCTAGGAAGGAGAGAAGAGTACGATGTTCTAGACAAGAGACGTGGCC

GGGACCCTGAGATGGGGGGAAAGCCACGAAGGAAGAACCCTCAGGAAGG

CCTGTACAACGAACTACAAAAAGATAAAATGGCGGAGGCCTACAGTGAG

```
ATTGGCATGAAAGGCGAGCGCCGGAGGGGCAAGGGGCACGATGGCCTTT

ACCAGGGCCTCAGTACAGCCACCAAGGACACCTATGACGCCCTTCACAT

GCAAGCTCTGCCCCCTCGC.
```

In embodiments, a NKG2D CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 47. LFNQEVQIPLTESYCGPCPKNWICYKNNCYQFFDESKNWYESQASCMSQNASLLKVYSKEDQDLLKLVKSYHWMGLVHIPTNGSWQWEDGSILSPNLLTIIEMQKGDCALYASSFK GYIENCSTPNTYICMQRTVTTTPAPRPPTPAPTIASQPLSLRPEACRPAAGGAVHTRGLDF ACDFWVLVVVGGVLACYSLLVTVAFIIFWVKRGRKKLLYIFKQPFMRPVQTTQEEDGC SCRFPEEEEGGCELRVKFSRSADAPAYQQGQNQLYNELNLGRREEYDVLDKRRGRDPE MGGKPRRKNPQEGLYNELQKDKMAEAYSEIGMKGERRRGKGHDGLYQGLSTATKDT YDALHMQALPPR (SEQ ID NO: 47). In embodiments, a NKG2D CAR binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                        (SEQ ID NO: 48)
TTATTCAACCAAGAAGTCCAGATTCCCTTGACCGAAAGTTACTGCGGCC

CATGTCCGAAAAACTGGATATGTTATAAAAATAACTGTTACCAGTTCTT

CGATGAATCTAAAAACTGGTATGAGAGCCAGGCATCTTGTATGTCTCAA

AATGCCAGCCTGCTCAAAGTATACAGCAAGGAGGACCAGGATTTACTTA

AACTGGTGAAGTCATATCACTGGATGGGATTGGTACACATTCCCACAAA

TGGATCTTGGCAGTGGGAAGACGGCTCCATTCTCTCACCCAACCTACTA

ACAATAATTGAAATGCAGAAGGGAGACTGCGCACTCTATGCATCGAGCT

TTAAAGGTTATATAGAAAACTGTTCAACTCCAAATACATACATCTGCAT

GCAAAGGACTGTAACAACGACGCCAGCGCCGCGACCACCAACACCGGCG

CCCACCATCGCGTCGCAACCCCTGTCCCTGAGGCCTGAAGCGTGCCGGC

CAGCGGCGGGGGCGCAGTGCACACGAGGGGCTGGACTTCGCTTGTGA

CTTTTGGGTATTGGTAGTAGTGGGCGGAGTCCTGGCTTGCTATAGTCTG

CTAGTAACAGTGGCTTTTATTATATTTTGGGTGAAACGAGGCAGAAAGA

AACTCCTGTATATATTCAAACAACCATTTATGAGACCAGTACAAACAAC

TCAGGAGGAGGATGGCTGTAGCTGCCGATTCCCGGAAGAAGAAGAAGGT

GGCTGTGAACTGAGAGTGAAGTTCAGCAGGAGCGCAGACGCCCCGCGT

ACCAGCAGGGGCAGAACCAACTCTATAACGAGCTCAATCTAGGAAGGAG

AGAAGAGTACGATGTTCTAGACAAGAGACGTGGCCGGGACCCTGAGATG

GGGGGAAAGCCACGAAGGAAGAACCCTCAGGAAGGCCTGTACAACGAAC

TACAAAAAGATAAAATGGCGGAGGCCTACAGTGAGATTGGCATGAAAGG

CGAGCGCCGGAGGGGCAAGGGGCACGATGGCCTTTACCAGGGCCTCAGT

ACAGCCACCAAGGACACCTATGACGCCCTTCACATGCAAGCTCTGCCCC

CTCGC.
```

In embodiments, a NKG2D CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 49. MALPVTALLLPLALLLHAARPLFNQEVQIPLTESYCGPCPKNWICYKNNCYQFFDESKN WYESQASCMSQNASLLKVYSKEDQDLLKLVKSYHWMGLVHIPTNGS WQWEDGSILSP NLLTIIEMQKGDCALYASSFKGYIENCSTPNTYICMQRTVTTTPAPRPPTPAPTIASQPLSL RPEACRPAAGGAVHTRGLDFACDFWVLVVVGGVLACYSLLVTVAFIIFWVKRGRKKL LYIFKQPFMRPVQTTQEEDGCSCRFPEEEEGGCEKNRKAKAKPVTRGAGAGGRQRGQN KERPPPVPNPDYEPIRKGQRDLYSGLLRVKFSRSADAPAYQQGQNQLYNELNLGRREEY DVLDKRRGRDPEMGGKPRRKNPQEGLYNELQKDKMAEAYSEIGMKGERRRGKGHDG LYQGLSTATKDTYDALHMQALPPR (SEQ ID NO: 49). In embodiments, a NKG2D CAR binding CAR is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                        (SEQ ID NO: 50)
ATGGCTCTTCCTGTGACAGCTCTTCTGCTGCCCCTGGCCCTGCTTCTGC

ATGCTGCTAGACCTTTATTCAACCAAGAAGTCCAAATTCCCTTGACCGA

AAGTTACTGTGGCCCATGTCCTAAAAACTGGATATGTTACAAAAATAAC

TGTTACCAATTCTTCGATGAAAGTAAAAACTGGTATGAGAGCCAGGCTT

CTTGTATGTCTCAAAATGCCAGCCTTCTGAAAGTATACAGCAAGGAGGA

CCAGGATTTACTTAAACTGGTGAAGTCATATCATTGGATGGGACTAGTA

CACATTCCAACAAATGGATCTTGGCAGTGGGAAGACGGCTCCATTCTCT

CACCCAACCTACTAACAATAATTGAAATGCAGAAGGGAGACTGTGCACT

CTATGCATCGAGCTTTAAAGGCTATATAGAAAACTGTTCAACTCCAAAT

ACATACATCTGCATGCAAAGGACTGTGACCACGACGCCAGCGCCGCGAC

CACCAACACCGGCGCCCACCATCGCGTCGCAACCCCTGTCCCTGCGCCC

AGAGGCGTGCCGGCCAGCGGCGGGGGCGCAGTGCACACGAGGGGCTG

GACTTCGCCTGTGATTTTTGGGTGCTGGTGGTGGTTGGTGGAGTCCTGG

CTTGCTATAGCTTGCTAGTAACAGTGGCCTTTATTATTTTCTGGGTGAA

ACGGGGCAGAAAGAAACTCCTGTATATATTCAAACAACCATTTATGAGA

CCAGTACAAACTACTCAAGAGGAAGATGGCTGTAGCTGCCGATTTCCAG

AAGAAGAAGGAGGATGTGAAAAGAACCGAAAAGCAAAAGCCAAGCC

TGTTACAAGAGGAGCAGGGGCAGGAGGCCGACAGAGAGGGCAAAACAAA

GAAAGGCCCCGCCCGTCCCAAACCCGGATTATGAGCCAATTAGGAAGG

GTCAGAGAGACCTGTATTCTGGGCTCCTGAGAGTGAAGTTCAGCAGGAG
```

```
                                                              -continued
CGCAGACGCCCCCGCGTACCAGCAGGGCCAGAACCAGCTCTATAACGAG

CTCAATCTAGGACGAAGAGAGGAGTACGATGTTTTGGACAAGAGACGTG

GCCGGGACCCTGAGATGGGGGGAAAGCCGAGAAGGAAGAACCCTCAGGA

AGGCCTGTACAACGAACTGCAGAAAGATAAGATGGCGGAGGCCTACAGT

GAGATTGGCATGAAAGGCGAGCGCCGGAGGGGCAAGGGGCACGACGGCC

TTTACCAGGGTCTCAGTACAGCCACCAAGGACACCTACGACGCCCTTCA

CATGCAGGCCCTGCCCCCTCGC.
```

In embodiments, a NKG2D CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 51. LFNQEVQIPLTESYCGPCPKNWICYKNN-CYQFFDESKNWYESQASCMSQNASLLKVYS KEDQDLLKLVKSYHWMGLVHIPTNGSWQWEDGSIL-SPNLLTIIEMQKGDCALYASSFK GYIENCSTPN-TYICMQRTVTTTPAPRPPTPAPTIASQPLSLRPEACR-PAAGGAVHTRGLDF ACDFWVLVVVGGVLACYSLLVTVAFIIFWVKR-GRKKLLYIFKQPFMRPVQTTQEEDGC SCRFPEEEEGGCEKNRKAKAKPVTRGAGAG-GRQRGQNKERPPPVPNPDYEPIRKGQRD LYSGLLRVKFSRSADAPAYQQGQNQLYNELNLGR-REEYDVLDKRRGRDPEMGGKPRR KNPQEGLY-NELQKDKMAEAYSEIGMKGERRRGKGHDGLYQGL-STATKDTYDALHMQ ALPPR (SEQ ID NO: 51). In embodiments, a NKG2D CAR binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                                 (SEQ ID NO: 52)
TTATTCAACCAAGAAGTCCAAATTCCCTTGACCGAAAGTTACTGTGGCC

CATGTCCTAAAAACTGGATATGTTACAAAAATAACTGTTACCAATTCTT

CGATGAAAGTAAAAACTGGTATGAGAGCCAGGCTTCTTGTATGTCTCAA

AATGCCAGCCTTCTGAAAGTATACAGCAAGGAGGACCAGGATTTACTTA

AACTGGTGAAGTCATATCATTGGATGGGACTAGTACACATTCCAACAAA

TGGATCTTGGCAGTGGGAAGACGGCTCCATTCTCTCACCCAACCTACTA

ACAATAATTGAAATGCAGAAGGGAGACTGTGCACTCTATGCATCGAGCT

TTAAAGGCTATATAGAAAACTGTTCAACTCCAAATACATACATCTGCAT

GCAAAGGACTGTGACCACGACGCCAGCGCCGCGACCACCAACACCGGCG

CCCACCATCGCGTCGCAACCCCTGTCCCTGCGCCCAGAGGCGTGCCGGC

CAGCGGCGGGGGCGCAGTGCACACGAGGGGGCTGGACTTCGCCTGTGA

TTTTTGGGTGCTGGTGGTGGTTGGTGGAGTCCTGGCTTGCTATAGCTTG

CTAGTAACAGTGGCCTTTATTATTTTCTGGGTGAAACGGGGCAGAAAGA

AACTCCTGTATATATTCAAACAACCATTTATGAGACCAGTACAAACTAC

TCAAGAGGAAGATGGCTGTAGCTGCCGATTTCCAGAAGAAGAAGAAGGA

GGATGTGAAAAGAACCGAAAAGCAAAAGCCAAGCCTGTTACAAGAGGAG
```

```
                                                    -continued
CAGGGGCAGGAGGCCGACAGAGAGGGCAAAACAAAGAAAGGCCCCCGCC

CGTCCCAAACCCGGATTATGAGCCAATTAGGAAGGGTCAGAGAGACCTG

TATTCTGGGCTCCTGAGAGTGAAGTTCAGCAGGAGCGCAGACGCCCCCG

CGTACCAGCAGGGCCAGAACCAGCTCTATAACGAGCTCAATCTAGGACG

AAGAGAGGAGTACGATGTTTTGGACAAGAGACGTGGCCGGGACCCTGAG

ATGGGGGGAAAGCCGAGAAGGAAGAACCCTCAGGAAGGCCTGTACAACG

AACTGCAGAAAGATAAGATGGCGGAGGCCTACAGTGAGATTGGCATGAA

AGGCGAGCGCCGGAGGGGCAAGGGGCACGACGGCCTTTACCAGGGTCTC

AGTACAGCCACCAAGGACACCTACGACGCCCTTCACATGCAGGCCCTGC

CCCCTCGC.
```

The present disclosure contemplates the use of the NKG2D CARs described herein with engineered T cell receptors (TCRs) used in T cell immunotherapy. Libraries of TCRs may be screened for their selectivity to target antigens. In this manner, natural TCRs, which have a high avidity and reactivity toward target antigens may be selected, cloned, and subsequently introduced into a population of T cells used for adoptive immunotherapy. A T cell or NK cell with an engineered TCR that also expresses the NKG2D CAR described herein would not only be able to target specific antigens due to TCR specificity but also cells expressing NKG2D ligands. Thus, combining TCRs with the NKG2D CAR described herein may provide a way to maintain or enhance the therapeutic effect of adoptive T cell or NK cell immunotherapy. In embodiments, a NKG2D CAR described herein is co-expressed with a TCR.

In one embodiment described herein, T cells or NK-cells are modified by introducing a polynucleotide encoding subunit of a TCR that may form TCRs that confer specificity to T cells or NK cells for tumor cells expressing a target antigen and/or a NKG2D ligand. In some embodiments, the subunits have one or more amino acid substitutions, deletions, insertions, or modifications compared to the naturally occurring subunit, so long as the subunits retain the ability to form TCRs conferring upon transfected T cells and NK cells the ability to home to target cells, and participate in immunologically-relevant cytokine signaling. The engineered TCRs may also bind target cells displaying the relevant tumor-associated peptide with high avidity, and optionally mediate efficient killing of target cells presenting the relevant peptide in vivo.

The nucleic acids encoding engineered TCRs may be isolated from their natural context in a (naturally-occurring) chromosome of a T cell, and may be incorporated into suitable vectors as described elsewhere herein. Both the nucleic acids and the vectors comprising them may be transferred into a cell, which cell may be a T cell. The modified T cells are then able to express one or more chains of a TCR (and in some aspects two chains) encoded by the transduced nucleic acid or nucleic acids. In some embodiments, the engineered TCR is an exogenous TCR because it is introduced into T cells that do not normally express the introduced TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The protein encoded by the nucleic acids described herein may be expressed with additional polypeptides attached to the amino-terminal or carboxyl-terminal portion of the α-chain or the β-chain of a TCR so long as the attached additional polypeptide does not interfere with the ability of the α-chain or the β-chain to form a functional T cell receptor and the MHC dependent antigen recognition.

Antigens that are recognized by the engineered TCRs contemplated herein include, but are not limited to cancer antigens, including antigens on both hematological cancers and solid tumors and viral induced cancers. TCR therapy for the treatment of HPV induced cervical carcinoma is an area of interest that holds promise. The oncolytic proteins HPV-16 E6 and HPV-16 E7 may thus be potential target antigens for use with TCR (see for example International Patent Application No. PCT/US2015/033129). Other illustrative antigens include, but are not limited HPV oncoproteins, including HPV-16 E6 and HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, MAGA-A3, HLA-A1+NY-ES0-1, HLA-A2+NY-ES0-1, HLA-A3+NY-ES0-1, IL-11Rα, IL-13Rα2, Lambda, Lewis-Y, Kappa, Mesothelin, Muc1, Muc16, NCAM, NKG2D Ligands, NY-ES0-1, PRAME, PSCA, PSMA, RORI, SSX, Survivin, TAG72, TACI, TEMs, and VEGFRII.

Combining any TCR construct as described herein with the NKG2D CARs of the present disclosure may restore, maintain or enhance the therapeutic effect of TCR therapy. Thus, in one embodiment described herein, the NKG2D CARs are co-expressed in a T cell or NK cell with a TCR directed against HPV. In another embodiment, the NKG2D CARs are co-expressed in a T cell or NK cell with a TCR directed against the HPV-16 E6 protein. In another embodiment described herein, the NKG2D CARs are co-expressed in a T cell or NK cells with a TCR directed against the HPV-16 E7 protein.

T cells or NK cells may also be genetically engineered with vectors designed to express a second CAR (in addition to a NKG2D CAR) that redirect cytotoxicity toward tumor cells. In some embodiments, CARs combine antibody based specificity for a target antigen (e.g., tumor antigen) with an activating intracellular domain to generate a chimeric protein that exhibits a specific anti-tumor cellular immune activity. The present disclosure contemplates the use of the NKG2D CARs described herein with one or more additional CARs. Like with the use of TCRs, co-expression of the NKG2D CARs with one or more additional CARs may promote expansion enhance, protect, and in some cases restore, CAR therapies. In embodiments, a NKG2D CAR is co-expressed with one or more additional CARs.

The one or more additional CARs contemplated herein comprise an extracellular domain that binds to a specific target antigen (also referred to as a binding domain or antigen-specific binding domain), a transmembrane domain and an intracellular signaling domain. The main characteristic of one or more additional CARs are their ability to redirect immune effector cell specificity, thereby triggering proliferation, cytokine production, phagocytosis or production of molecules that may mediate cell death of the target antigen expressing cell in a major histocompatibility (MHC) independent manner, exploiting the cell specific targeting abilities of monoclonal antibodies, soluble ligands or cell specific co-receptors.

In some embodiments, the one or more additional CAR comprises an extracellular binding domain including but not limited to an antibody or antigen binding fragment thereof, a tethered ligand, or the extracellular domain of a co-receptor, that specifically binds a target antigen. By way of non-limiting examples, target antigens may include: HPV oncoproteins, including HPV-16 E6 and HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, HLA-A1+NY-ES0-1, HLA-A2+NY-ES0-1, HLA-A3+NY-ES0-1, IL-11Rα, IL-13Rα2, Lambda, Lewis-Y, Kappa, Mesothelin, Muc1, Muc16, NCAM, NKG2D Ligands, NYE-S0-1, PRAME, PSCA, PSMA, RORI, SSX, Survivin, TACI, TAG72, TEMs, and VEGFRII; In embodiments described herein, the CAR binds to a tumor antigen comprising BCMA, CLL-1, CD19, CD20, CD22, CD28, CD137 (4-1BB), Glypican-3 (GPC3), PSCA, PSMA, or TACI.

In some embodiments, the one or more additional CARs contemplated herein comprise an extracellular binding domain that specifically binds to a target polypeptide, e.g., target antigen, expressed on tumor cell. As used herein, the terms, "binding domain," "extracellular domain," "extracellular binding domain," "antigen-specific binding domain," "antigen binding domain" and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In some embodiments, the extracellular binding domain of the one or more additional CAR comprises an antibody or antigen binding fragment thereof. An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments thereof. The term also includes genetically engineered forms such as chimeric antibodies (for example, humanized murine antibodies), hetero-conjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

In some embodiments, the target antigen is an epitope of an HPV oncoproteins, including HPV-16 E6 and HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA- A1+MAGEI, HLA-A2+MAGE1, HLAA3+MAGE1, HLA-A1+NY-ES0-1, HLA-A2+NY-ES0-1, HLA-A3+NY-ES0-1, IL-11Rα, IL-13Rα2, Lambda, Lewis-Y, Kappa, Mesothelin, Muc1, Muc16, NCAM, NKG2D Ligands, NYE-S0-1, PRAME, PSCA, PSMA, RORl, SSX, Survivin, TAG72, TEMs, TACI, and VEGFRII polypeptide. In one embodiment described herein, the CAR binds to a tumor antigen epitope comprising BCMA, CLL-1, CD19, CD20, CD22, CD28, CD137 (4-1BB), Glypican-3 (GPC3), PSCA, PSMA, or TACI.

In certain embodiments, the one or more additional CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers (G1-5S1-5)n (SEQ ID NO: 78), where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, Rev. Computational Chem. 11173-142 (1992)). Other linkers contemplated herein include Whitlow linkers (see Whitlow, Protein Eng. 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker (SEQ ID NO: 6). In another embodiment, any of the constructs described herein comprise a "GSG" linker. In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 11.

```
                                    (SEQ ID NO: 11)
GSTSGSGKPGSGEGSTKG.
```

In other embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In other embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

Where expression of two or more polypeptides is desired, the polynucleotide sequences encoding them may be separated by an IRES sequence. In another embodiment, two or more polypeptides may be expressed as a fusion protein that comprises one or more self-cleaving polypeptide sequences, such as a T2A polypeptide. In other embodiments, they are expressed from different promotors and can be in two or more vectors. In some embodiments, a NKG2D CAR is encoded in the same vector as a TCR and/or one or more non-NKG2D CARs and is operably linked to the same promotor where the sequences are separated by an IRES sequence. In some embodiments, a NKG2D CAR is encoded in the same vector as a TCR and/or one or more non-NKG2D CARs and is operably linked to the same promotor where the sequences are separated by a cleavable linker. In some embodiments, a NKG2D CAR is encoded in the same vector as a TCR and/or one or more non-NKG2D CARs and the NKG2D CAR is operably linked to a different promotor than the TCR and/or one or more non-NKG2D CARs. In some embodiments, a NKG2D CAR is encoded in a different vector than a TCR and/or one or more non-NKG2D CARs.

"Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in some embodiments, it may be desirable to improve the binding affinity and/or other biological properties of the engineered NKG2D CARs by introducing one or more substitutions, deletions, additions and/or insertions. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multi-meric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support. As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol*, 154: 367-382), U.S. Pat. No. 4,873, 192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Polypeptides of the present disclosure include fusion polypeptides. In some embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they may also be linked C-terminus to C-terminus, N-terminus to N-terminus, or N-terminus to C-terminus. The polypeptides of the fusion protein may be in any order or a specified order. Fusion polypeptides or fusion proteins may also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other common techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site may be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26). Suitable protease cleavages sites and self-cleaving peptides are known to the skilled person (see, e.g., in Ryan et al., 1997. *J Gener. Viral.* 78, 699-722; Scymczak et al. (2004) *Nature Biotech.* 5, 589-594). Exemplary protease cleavage sites include, but are not limited to the cleavage sites of potyvirus Nia proteases (e.g., tobacco etch virus protease), potyvirus HC proteases, potyvirus P1 (P35) proteases, byovirus Nia proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites may be used. In other embodiments, self-cleaving peptides may include those polypeptide sequences obtained from potyvirus and cardiovirus 2A peptides, FMDV (foot-and-mouth disease virus), equine rhinitis A virus, Thosea asigna virus and porcine teschovirus. In other embodiments, the self-cleaving polypeptide site comprises a 2A or 2A-like site, sequence or domain (Donnelly et al., 2001. J Gen. Viral. 82:1027-1041).

Generally, it is understood that any appropriate viral vector or vectors may be used for transduction of the engineered constructs described herein. In one embodiment described herein, a cell (e.g., T cell, NK cell or iPSC) is transduced with a retroviral vector, e.g., a lentiviral vector. As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (FIV); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, Rand U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J of Virology, Vol. 69, No. 4; pp. 2101-2109. Several retroviral vectors use the minimal packaging signal (also referred to as the psi ['P] sequence) needed for encapsidation of the viral genome. Thus, as used herein, the terms "packaging sequence," "packaging signal," "psi" and the symbol "'P," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly(A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, Cell, 101: 173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J Virol. 65: 1053; and Cullen et al., 1991. Cell 58: 423), and the hepatitis B virus post-transcriptional regulatory element (HPRE). Generally, the RNA export element is placed within the 3' UTR of a gene, and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, J Virol., 73:2886); the post-transcriptional regulatory element present in hepatitis B virus (HPRE) (Huang et al., Mol. Cell. Biol., 5:3864); and the like (Liu et al., 1995, Genes Dev., 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide, can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein.

The codon-optimized nucleotide sequences can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability domain, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, IOAI envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, or any encephaliltis causing virus.

The terms "pseudotype" or "pseudotyping" as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRCS cells, A549 cells, HTI080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) Nucl. Acids Res. 23:628-633, and N. R. Landau et al. (1992) J Virol. 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell or NK cell, is "transduced" if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome.

Disclosed are host cells expressing one or more of the constructs of the disclosure. The host cells may be transduced with one or more viral vectors comprising nucleic acid sequences encoding one or more polypeptides expressing an engineered TCR and/or a CAR. Other methods relating to the use of viral vectors in gene therapy, which may be utilized according to certain embodiments of the present disclosure, may be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al., (1999) Liver 19:265-74; Oka, K. et al., (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J Hepatol. 23:746-58; Brody, S. L. and Crystal, R. G. (1994) Ann. NY Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al., (2000) Nature 408:483-8.

The compositions described herein may comprise one or more polynucleotides, polypeptides, vectors comprising same, and T cell composition and NK compositions, as contemplated herein. One embodiment described herein is a composition comprising a modified T cell that expresses a NKG2D CAR. Another embodiment described herein is a composition comprising a modified NK cell that expresses a NKG2D CAR. Compositions include, but are not limited to, pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells or NK cells contemplated herein. It may generally be stated that a pharmaceutical composition comprising the T cells or NK cells contemplated herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells or NK cells modified to express an engineered NKG2D CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells or NK cells contemplated herein are used in the treatment of cancers. The modified T cells or NK cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells or NK cells, in combination with one or more pharmaceutically or physiologically acceptable carriers, diluents or excipients.

Pharmaceutical compositions comprising modified T cells or NK cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intra-arterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell or NK cell composition, alone or in combination with one or more therapeutic agents. Thus, the T cell or NK cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells or NK cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2" trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR or TCR modified T cells or NK cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-15, a tumor necrosis factor such as TNF-α or TNF-β; and other polypeptide factors including LIF and kit ligand (KL). As used herein, the term cytokine includes proteins from natural sources or from recombinant cell culture, and biologically active equivalents of the native sequence cytokines.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof. Unlike antibody therapies or stand-alone NKG2D CAR modified T cells, T cells (or any cells as described above).

Another embodiment described herein is a method of treating a cancer in a subject in need thereof comprising administering an effective amount, e.g., therapeutically effective amount of a composition comprising T cells or NK cells expressing TCR or CAR as described herein. The quantity and frequency of administration will be determined by such factors as the condition of the patient, and the type and severity of the patient's disease, although appropriate dosages may be determined by clinical trials.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to affect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10 cc to 400 cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In embodiments described herein is a method of treating a subject diagnosed with a cancer, comprising removing T cells from the subject, genetically modifying said T cells with a vector comprising a nucleic acid encoding a NKG2D CAR as contemplated herein, thereby producing a population of modified T cells, and administering the population of modified T cells to the same subject.

In certain embodiments, the present disclosure also provides methods for stimulating an effector cell mediated immune modulator response to a target cell population in a subject comprising the steps of administering to the subject an immune effector cell population expressing a nucleic acid construct encoding a NKG2D CAR molecule.

The methods for administering the cell compositions described herein includes any method which is effective to result in reintroduction of ex vivo genetically modified immune effector cells that either directly express an engineered NKG2D CAR in the subject or on reintroduction of the genetically modified progenitors of immune effector cells that on introduction into a subject differentiate into mature immune effector cells that express the d NKG2D CAR molecule. One method comprises transducing peripheral blood T cells ex vivo with a nucleic acid construct in accordance with the present disclosure and returning the transduced cells into the subject.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield essentially similar results.

EXAMPLES

Example 1

NKG2D CAR Construct Design

As used in the following Examples engineered NKG2D chimeric antigen receptor constructs were designed and synthesized in a retroviral vector. A first construct, termed NKG2D CAR1 includes from N to C-terminus a signal peptide, a NKG2D extracellular domain, a CD8alpha hinge, a CD28 transmembrane domain, a 4-1BB intercellular domain, and a signaling domain comprising a CD3ζ signaling domain. The amino acid sequence of this chimeric antigen receptor is shown below:

(SEQ ID NO: 53)
MALPVTALLLPLALLLHAARPLFNQEVQIPLTESYCGPCPKNWICYKNN

CYQFFDESKNWYESQASCMSQNASLLKVYSKEDQDLLKLVKSYHWMGLV

HIPTNGSWQWEDGSILSPNLLTIIEMQKGDCALYASSFKGYIENCSTPN

-continued

TYICMQRTVTTTPAPRPPTPAPTIASQPLSLRPEACRPAAGGAVHTRGL

DFACDFWVLVVVGGVLACYSLLVTVAFIIFWVKRGRKKLLYIFKQPFMR

PVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSE

IGMKGERRRGKGHDGLYQGLSTATKDTYDALHMQALPPR.

A second construct, termed NKG2D CAR2 includes from N to C-terminus a signal peptide, a NKG2D extracellular domain, a CD8alpha hinge, a CD28 transmembrane domain, a 4-1BB intercellular domain, and a signaling domain comprising a CD3c signaling domain and a CD3 signaling domain. The amino acid sequence of this chimeric antigen receptor is shown below:

(SEQ ID NO: 54)
MALPVTALLLPLALLLHAARPLFNQEVQIPLTESYCGPCPKNWICYKNN

CYQFFDESKNWYESQASCMSQNASLLKVYSKEDQDLLKLVKSYHWMGLV

HIPTNGSWQWEDGSILSPNLLTIIEMQKGDCALYASSFKGYIENCSTPN

TYICMQRTVTTTPAPRPPTPAPTIASQPLSLRPEACRPAAGGAVHTRGL

DFACDFWVLVVVGGVLACYSLLVTVAFIIFWVKRGRKKLLYIFKQPFMR

-continued

PVQTTQEEDGCSCRFPEEEEGGCEKNRKAKAKPVTRGAGAGGRQRGQNK

ERPPPVPNPDYEPIRKGQRDLYSGLLRVKFSRSADAPAYQQGQNQLYNE

LNLGRREEYDVLDKRRGRDPEMGGKPRRKNPQEGLYNELQKDKMAEAYS

EIGMKGERRRGKGHDGLYQGLSTATKDTYDALHMQALPPR.

A third construct, termed NKG2D CAR3 comprises from N to C-terminus a NKG2D extracellular domain, a CD8 hinge, a CD8 transmembrane domain, a 4-1BB intercellular domain, and a signaling domain comprising a CD3ζ signaling domain. The amino acid sequence of this chimeric antigen receptor comprises the following amino acid sequence: LFNQEVQIPLTESYCGPCPKNWICYKNNCYQFFDESKNWYESQASCMSQNASLLKVYS KEDQDLLKLVKSYHWMGLVHIPTNGSWQWEDGSILSPNLLTIIEMQKGDCALYASSFK GYIENCSTPNTYICMQRTVTTTPAPRPPTPAPTIASQPLSLRPEACRPAAGGAVHTRGLDF ACDIYIWAPLAGTCGVLLLSLVITLYCKRGRKKLLYIFKQPFMRPVQTTQEEDGCSCRFP EEEEGGCELRVKFSRSADAPAYQQGQNQLYNELNLGRREEYDVLDKRRGRDPEMGGK PRRKNPQEGLYNELQKDKMAEAYSEIGMKGERRRGKGHDGLYQGLSTATKDTYDALH MQALPPR (SEQ ID NO: 66). In one aspect, CAR3 is encoded by the following nucleotide sequence:

(SEQ ID NO: 67)
```
   1 cgtgaggctc cggtgcccgt cagtgggcag agcgcacatc gcccacagtc cccgagaagt
  61 tggggggagg ggtcggcaat tgaaccggtg cctagagaag gtggcgcggg gtaaactggg
 121 aaagtgatgt cgtgtactgg ctccgccttt ttcccgaggg tgggggagaa ccgtatataa
 181 gtgcagtagt cgccgtgaac gttctttttc gcaacgggtt tgccgccaga acacaggtaa
 241 gtgccgtgtg tggttcccgc gggcctggcc tctttacggg ttatggccct tgcgtgcctt
 301 gaattacttc cacgccctg gctgcagtac gtgattcttg atcccgagct tcggttgga
 361 agtgggtggg agagttcgag gccttgcgct taaggagccc cttcgcctcg tgcttgagtt
 421 gaggcctggc ttgggcgctg gggccgccgc gtgcgaatct ggtggcacct tcgcgcctgt
 481 ctcgctgctt tcgataagtc tctagccatt taaaattttt gatgacctgc tgcgacgctt
 541 tttttctggc aagatagtct tgtaaatgcg ggccaagatc tgcacactgg tatttcggtt
 601 tttggggccg cgggcggcga cggggcccgt gcgtcccagc gcacatgttc ggcgaggcgg
 661 ggcctgcgag cgcggccacc gagaatcgga cggggtagt ctcaagctgg ccggcctgct
 721 ctggtgcctg gcctcgcgcc gccgtgtatc gccccgccct gggcggcaag gctggcccgg
 781 tcggcaccag ttgcgtgagc ggaaagatgg ccgcttcccg gccctgctgc agggagctca
 841 aaatggagga cgcggcgctc gggagagcgg gcgggtgagt cacccacaca aggaaaagg
 901 gccttccgt cctcagccgt cgcttcatgt gactccacgg agtaccgggc gccgtccagg
 961 cacctcgatt agttctcgag cttttggagt acgtcgtctt taggttgggg ggaggggttt
1021 tatgcgatgg agtttcccca cactgagtgg gtggagactg aagttaggcc agcttggcac
1081 ttgatgtaat tctccttgga atttgccctt tttgagtttg gatcttggtt cattctcaag
1141 cctcagacag tggttcaaag ttttttttctt ccatttcagg tgtcgtgaaa actaccccta
1201 aaagccaaag cgccgccacc atggctcttc ctgtgacagc tcttctgctg cccctggccc
1261 tgcttctgca tgctgctaga cctgagcaaa agttgatttc tgaggaagac ctcgccggca
1321 gtttattcaa ccaagaagtc caaattccct tgaccgaaag ttactgtggc ccatgtccta
```

```
1381  agaactggat atgttacaaa aataactgtt accaattctt cgatgaatct aagaattggt
1441  atgagagcca ggcttcttgt atgtctcaaa atgccagcct tcttaaagta tacagcaaag
1501  aggaccagga tttacttaaa ctggtgaagt catatcattg gatgggacta gtacacattc
1561  caacaaatgg atcttggcag tgggaagacg gctccattct ctcacccaac ctactaacaa
1621  taattgaaat gcagaaggga gactgtgcac tctatgcatc gagctttaaa ggctatatag
1681  aaaactgttc aactccaaat acatatattt gcatgcaaag gactgtgacc acgacgccag
1741  cgccgcgacc accaacaccg gcgcccacca tcgcgtcgca acccctgtcc ctgaggcctg
1801  aagcgtgccg gccagcgcg gcggcgca tgcacacgag agggctggac ttcgcctgtg
1861  atatctacat ctgggcgccc ttggccggga cttgtggggt ccttctcctg tcactggtta
1921  tcacccttta ctgcaaacgg ggcagaaaaa aactcctgta tatattcaaa caaccattta
1981  tgagaccagt acaaactact caagaggaag atggctgtag ctgccgattt ccagaagaag
2041  aagaaggagg atgtgaactg agagtgaagt tcagcaggag cgcagacgcc ccgcgtacc
2101  agcaagggca gaaccagctc tataacgagc tcaatctagg acgaagagag gagtacgatg
2161  ttttggacaa gaggcgtggc cgggaccctg agatgggggg aaagccgaga aggaagaacc
2221  ctcaggaagg cctgtacaat gaactgcaga aagataagat ggcggaggcc tacagtgaga
2281  ttgggatgaa aggcgagcgc cggaggggca aggggcacga tggcctttac cagggtctca
2341  gtacagccac caaggacacc tacgacgccc ttcacatgca agctctgccc cctcgctga.
```

CAR3 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 67). In certain aspects, the nucleic acid sequence of (SEQ ID NO: 67) may be modified to remove sequences encoding the Myc (human c-Myc proto-oncogene) epitope tag and linker between the Myc tag and the NKG2D extracellular domain. The nucleic acid sequence of (SEQ ID NO: 67) encodes for a CD8a signal peptide at positions 1221-1283, which signal peptide may be substituted for a different signal peptide.

A fourth construct, termed NKG2D CAR4 comprises from N to C-terminus a NKG2D extracellular domain, a CD8alpha hinge, a CD28 transmembrane domain, a 4-1BB intercellular domain, and a signaling domain comprising a CD3ζ signaling domain. The amino acid sequence of this chimeric antigen receptor comprises the following amino acid sequence: LFNQEVQIPLTESYCGPCPKNWICYKNNCYQFFDESKNWYESQASCMSQNASLLKVYSKEDQDLLKLVKSYHWMGLVHIPTNGSWQWEDGSILSPNLLTIIEMQKGDCALYASSFK GYIENCSTPNTYICMQRTVTTTPAPRPPTPAPTIASQPLSLRPEACRPAAGGAVHTRGLDF ACDFWVLVVVGGVLACYSLLVTVAFIIFWVKR-GRKKLLYIFKQPFMRPVQTTQEEDGC SCRFPEEEEGGCELRVKFSRSADAPAYQQGQNQLY-NELNLGRREEYDVLDKRRGRDPE MGGKPRRKNPQEGLYNELQKDKMAEAYSEI-GMKGERRRGKGHDGLYQGLSTATKDT YDALHMQALPPR (SEQ ID NO: 68). In one aspect, CAR4 is encoded by the following nucleotide sequence:

```
                                                      (SEQ ID NO: 69)
1    cgtgaggctc cggtgcccgt cagtgggcag agcgcacatc gcccacagtc cccgagaagt
61   tggggggagg ggtcggcaat tgaaccggtg cctagagaag gtggcgcggg gtaaactggg
121  aaagtgatgt cgtgtactgg ctccgccttt ttcccgaggg tgggggagaa ccgtatataa
181  gtgcagtagt cgccgtgaac gttcttttc gcaacgggtt tgccgccaga acacaggtaa
241  gtgccgtgtg tggttcccgc gggcctggcc tctttacggg ttatggccct tgcgtgcctt
301  gaattacttc cacgcccctg gctgcagtac gtgattcttg atcccgagct tcgggttgga
361  agtgggtggg agagttcgag gccttgcgct taaggagccc cttcgcctcg tgcttgagtt
421  gaggcctggc ttgggcgctg gggccgccgc gtgcgaatct ggtggcacct tcgcgcctgt
481  ctcgctgctt tcgataagtc tctagccatt taaaattttt gatgacctgc tgcgacgctt
541  tttttctggc aagatagtct tgtaaatgcg ggccaagatc tgcacactgg tatttcggtt
601  tttggggccg cgggcggcga cggggcccgt gcgtcccagc gcacatgttc ggcgaggcgg
```

```
 661  ggcctgcgag cgcggccacc gagaatcgga cggggtagt ctcaagctgg ccggcctgct 721  ctggtgcctg gcctcgcgcc gccgtgtatc gccccgccct gggcggcaag gctggcccgg 781  tcggcaccag ttgcgtgagc ggaaagatgg ccgcttcccg gccctgctgc agggagctca 841  aaatggagga cgcggcgctc gggagagcgg gcgggtgagt cacccacaca aaggaaaagg 901  gcctttccgt cctcagccgt cgcttcatgt gactccacgg agtaccgggc gccgtccagg 961  cacctcgatt agttctcgag cttttggagt acgtcgtctt taggttgggg ggaggggttt 1021  tatgcgatgg agtttcccca cactgagtgg gtggagactg aagttaggcc agcttggcac 1081  ttgatgtaat tctccttgga atttgccctt tttgagtttg gatcttggtt cattctcaag 1141  cctcagacag tggttcaaag ttttttttctt ccatttcagg tgtcgtgaaa actacccta 1201  aaagccaaag cgccgccacc atggctcttc ctgtgacagc tcttctgctg cccctggccc 1261  tgcttctgca tgctgctaga cctgagcaaa agttgatttc tgaggaagac ctcgccggca 1321  gtttattcaa ccaagaagtc caaattccct tgaccgaaag ttactgtggc ccatgtccta 1381  agaactggat atgttacaaa ataactgtt accaattctt cgatgaatct aagaattggt 1441  atgagagcca ggcttcttgt atgtctcaaa atgccagcct tcttaaagta tacagcaaag 1501  aggaccagga tttacttaaa ctggtgaagt catatcattg gatgggacta gtacacattc 1561  caacaaatgg atcttggcag tgggaagacg gctccattct ctcacccaac ctactaacaa 1621  taattgaaat gcagaaggga gactgtgcac tctatgcatc gagctttaaa ggctatatag 1681  aaaactgttc aactccaaat acatatattt gcatgcaaag gactgtgacc acgacgccag 1741  cgccgcgacc accaacaccg gcgcccacca tcgcgtcgca acccctgtcc ctgaggcctg 1801  aagcgtgccg gccagcggcg ggcggcgcag tgcacacgag agggctggac ttcgcctgtg 1861  atttttgggt gctggtggtg gttggtggag tcctggcttg ctatagcttg ctagtaacag 1921  tggcctttat tattttctgg gtcaaacggg gcagaaagaa actcctgtat atattcaaac 1981  aaccatttat gagaccagta caaactactc aagaggaaga tggctgtagc tgccgatttc 2041  cagaagaaga agaaggagga tgtgaactga gagtgaagtt cagcaggagc gcagacgccc 2101  ccgcgtacca gcaagggcag aaccagctct ataacgagct caatctagga cgaagagagg 2161  agtacgatgt tttggacaag aggcgtggcc gggaccctga gatgggggga aagccgagaa 2221  ggaagaaccc tcaggaaggc ctgtacaatg aactgcagaa agataagatg cggaggcct 2281  acagtgagat tgggatgaaa ggcgagcgcc ggaggggcaa ggggcacgat ggcctttacc 2341  agggtctcag tacagccacc aaggacacct acgacgccct tcacatgcaa gctctgcccc 2401  ctcgctga
```

CAR4 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 69). In certain aspects, the nucleic acid sequence of (SEQ ID NO: 69) may be modified to remove sequences encoding the Myc (human c-Myc proto-oncogene) epitope tag and linker between the Myc tag and the NKG2D extracellular domain. The nucleic acid sequence of (SEQ ID NO: 69) encodes for a CD8a signal peptide at positions 1221-1283, which signal peptide may be substituted for a different signal peptide.

A fifth construct, termed NKG2D CAR5 comprises from N to C-terminus a NKG2D extracellular domain, a CD8 hinge, a CD8 transmembrane domain, a 4-1BB intercellular domain, and a signaling domain comprising a CDR signaling domain and a CD3 signaling domain. The amino acid sequence of this chimeric antigen receptor comprises the following amino acid sequence: LFNQEVQIPLTESYCGPCPKNWICYKNN-CYQFFDESKNWYESQASCMSQNASLLKVYS KEDQDLLKLVKSYHWMGLVHIPTNGSWQWEDGSIL-SPNLLTIIEMQKGDCALYASSFK GYIENCSTPN-TYICMQRTVTTTPAPRPPTPAPTIASQPLSLRPEACR-PAAGGAVHTRGLDF AIYIWAPLAGTCGVLLLSLVITLYCKRGRKKLLY-IFKQPFMRPVQTTQEEDGCSCRFPEE EEGGCELKNRKAKAKPVTRGAGAGGRQRGQNKER-PPPVPNPDYEPIRKGQRDLYSGLN QRRILRVKFSRS-ADAPAYQQGQNQLYNELNLGRREEYDVLDKRR-GRDPEMGGKPRRK NPQEGLYNELQKDKMAEAYSEI-GMKGERRRGKGHDGLYQGLSTATKDTYDALHMQA LPPR (SEQ ID NO: 70). In one aspect, CAR5 is encoded by the following nucleotide sequence:

(SEQ ID NO: 71)

```
   1 cgcggaatga aagaccccac ctgtaggttt ggcaagctag cttaagtaac gccattttgc
  61 aaggcatgga aaatacataa ctgagaatag agaagttcag atcaaggtta ggaacagaga
 121 gacagcagaa tatgggccaa acaggatatc tgtggtaagc agttcctgcc ccggctcagg
 181 gccaagaaca gatggtcccc agatgcggtc ccgccctcag cagtttctag agaaccatca
 241 gatgtttcca gggtgcccca aggacctgaa atgaccctgt gccttatttg aactaaccaa
 301 tcagttcgct tctcgcttct gttcgcgcgc ttctgctccc cgagctcaat aaaagagccc
 361 acaacccctc actcggcgcg ccagtccttc gaagtagatc tttgtcgatc ctaccatcca
 421 ctcgacacac ccgccagcgg ccgctgccaa gcttccgagc tctcgaatta attcacgccg
 481 ccaccatggc tcttcctgtg acagctcttc tgctgcccct ggccctgctt ctgcatgctg
 541 ctagacctga gcaaaagttg atttctgagg aagacctcgc cggcagttta ttcaaccaag
 601 aagtccaaat tcccttgacc gaaagttact gtggcccatg tcctaagaac tggatatgtt
 661 acaaaaataa ctgttaccaa ttcttcgatg aatctaagaa ttggtatgag agccaggctt
 721 cttgtatgtc tcaaaatgcc agccttctta agtatacag caaagaggac caggatttac
 781 ttaaactggt gaagtcatat cattggatgg gactagtaca cattccaaca aatggatctt
 841 ggcagtggga agacggctcc attctctcac ccaacctact aacaataatt gaaatgcaga
 901 agggagactg tgcactctat gcatcgagct ttaaaggcta tatagaaaac tgttcaactc
 961 caaatacata tatttgcatg caaaggactg tgaccaccac tcctgctcca agacctccta
1021 cccccgctcc tacaatcgcc agccaacctc tgagcctgag accggaggca tgcagacctg
1081 cggcagggg agcagttcac acaagaggct tggacttcgc ttgcgacatc tacatctggg
1141 cccctctggc cggcacatgc ggagttcttc ttcttagcct ggtgatcacc ctgtactgca
1201 agagaggccg gaagaagctg ctgtacatct tcaagcagcc cttcatgaga cctgtgcaga
1261 ccacacagga ggaagacggc tgcagctgta gattcccga ggaagaggag ggcggctgtg
1321 agctgaagaa ccgcaaagca aaggcaaaac ccgtcacacg aggagcgggc cagggggac
1381 gacaacgcgg tcagaataag aacgcccgc ctccagtacc aaatccagat tatgaaccaa
1441 ttcggaaggg acaacgcgat ctctactccg gtctcaatca gaggcgaatt ctgagagtta
1501 agttcagcag gagcgccgac gcccctgcct accagcaagg acagaatcaa ctgtacaacg
1561 agctgaacct gggcagacgg gaggaatacg atgtgctgga caagaggaga ggcagagacc
1621 ccgagatggg cggcaaacct agaagaaaga ccccaggga gggcctgtat aacgagctcc
1681 agaaggacaa gatggccgag gcctacagcg agatcggcat gaagggcgaa agaagaagag
1741 gcaagggcca cgacggcctc taccagggct taagcacagc tacaaaggac acctacgacg
1801 ccctgcacat gcaggccctg cccctagat ga
```

CAR5 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 71). In certain aspects, the nucleic acid sequence of (SEQ ID NO: 71) may be modified to remove sequences encoding the Myc (human c-Myc proto-oncogene) epitope tag and linker between the Myc tag and the NKG2D extracellular domain. The nucleic acid sequence of (SEQ ID NO: 71) encodes for a CD8a signal peptide at positions 486-548, which signal peptide may be substituted for a different signal peptide.

A sixth construct, termed NKG2D CAR6 comprises from N to C-terminus a NKG2D extracellular domain, a CD8alpha hinge, a CD8 transmembrane domain, a 4-1BB intercellular domain, and a signaling domain comprising a CDR signaling domain and a CD3ζ signaling domain. The amino acid sequence of this chimeric antigen receptor comprises the following amino acid sequence: LFNQEVQIPLTESYCGPCPKNWICYKNN- CYQFFDESKNWYESQASCMSQNASLLKVYS
KEDQDLLKLVKSYHWMGLVHIPTNGSWQWEDGSIL-
SPNLLTIIEMQKGDCALYASSFK GYIENCSTPN-
TYICMQRTVTTTPAPRPPTPAPTIASQPLSLRPEACR-
PAAGGAVHTRGLDF
ACDIYIWAPLAGTCGVLLLSLVITLYCKRGRKKLLY-
IFKQPFMRPVQTTQEEDGCSCRFP
EEEEGGCEKNRKAKAKPVTRGAGAG-
GRQRGQNKERPPPVPNPDYEPIRKGQRDLYSGL
LRVKFSRSADAPAYQQGQNQLYNELNLGRREEY-
DVLDKRRGRDPEMGGKPRRKNPQE GLYNELQKDK-
MAEAYSEIGMKGERRRGKGHDGLYQGLSTATKDTY-
DALHMQALPPR (SEQ ID NO: 72). In one aspect, CAR6 is encoded by the following nucleotide sequence:

CAR6 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 73). In certain aspects, the nucleic acid sequence of (SEQ ID NO: 73) may be modified to remove sequences encoding the Myc (human c-Myc proto-oncogene) epitope tag and linker between the Myc tag and the NKG2D extracellular domain. The nucleic acid sequence of (SEQ ID NO: 73) encodes for a CD8a signal peptide at positions 486-548, which signal peptide may be substituted for a different signal peptide.

A seventh construct, termed NKG2D CAR7 comprises from N to C-terminus a NKG2D extracellular domain, a CD8alpha hinge, a CD28 transmembrane domain, a 4-1BB

```
                                                                (SEQ ID NO: 73)
   1 cgcggaatga aagacccccac ctgtaggttt ggcaagctag cttaagtaac gccatttttgc 61 aaggcatgga aaatacataa ctgagaatag agaagttcag atcaaggtta ggaacagaga 121 gacagcagaa tatgggccaa acaggatatc tgtggtaagc agttcctgcc ccggctcagg 181 gccaagaaca gatggtcccc agatgcggtc ccgccctcag cagtttctag agaaccatca 241 gatgtttcca gggtgcccca aggacctgaa atgaccctgt gccttatttg aactaaccaa 301 tcagttcgct tctcgcttct gttcgcgcgc ttctgctccc cgagctcaat aaaagagccc 361 acaacccctc actcggcgcg ccagtccttc gaagtagatc tttgtcgatc ctaccatcca 421 ctcgacacac ccgccagcgc ccgctgccaa gcttccgagc tctcgaatta attcacgccg 481 ccaccatggc tcttcctgtg acagctcttc tgctgccccct ggccctgctt ctgcatgctg 541 ctagacctga gcaaaagttg atttctgagg aagacctcgc ggcagttta ttcaaccaag 601 aagtccaaat tcccttgacc gaaagttact gtggcccatg tcctaagaac tggatatgtt 661 acaaaaataa ctgttaccaa ttcttcgatg aatctaagaa ttggtatgag agccaggctt 721 cttgtatgtc tcaaaatgcc agccttctta agtatacag caaagaggac caggatttac 781 ttaaactggt gaagtcatat cattggatgg gactagtaca cattccaaca aatggatctt 841 ggcagtggga agacggctcc attctctcac ccaacctact aacaataatt gaaatgcaga 901 agggagactg tgcactctat gcatcgagct ttaaaggcta tatagaaaac tgttcaactc 961 caaatacata tatttgcatg caaaggactg tgaccacgac gccagcgccg cgaccaccaa 1021 caccggcgcc caccatcgcg tcgcaacccc tgtccctgag gcctgaagcg tgccggccag 1081 cggcgggcgg cgcagtgcac acgagagggc tggacttcgc ctgtgatatc tacatctggg 1141 cgcccttggc cgggacttgt ggggtccttc tcctgtcact ggttatcacc ctttactgca 1201 aacggggcag aaagaaactc ctgtatatat tcaaacaacc atttatgaga ccagtacaaa 1261 ctactcaaga ggaagatggc tgtagctgcc gatttccaga agaagaagaa ggaggatgtg 1321 aaaagaaccg aaaagcaaaa gccaagcctg ttacaagagg agcaggggca ggaggccgac 1381 agagagggca aaacaaagaa aggcccccgc ccgtcccaaa cccggattat gagccaatta 1441 ggaagggtca gagagacctg tattctgggc tcctgagagt gaagttcagc aggagcgcag 1501 acgccccgc gtaccagcaa gggcagaacc agctctataa cgagctcaat ctaggacgaa 1561 gagaggagta cgatgttttg gacaagaggc gtggccggga ccctgagatg gggggaaagc 1621 cgagaaggaa gaaccctcag gaaggcctgt acaatgaact gcagaaagat aagatggcgg 1681 aggcctacag tgagattggg atgaaaggcg agcgccggag gggcaagggg cacgatggcc 1741 tttaccaggg tctcagtaca gccaccaagg acacctacga cgcccttcac atgcaagctc 1801 tgccccctcg ctga
``` intercellular domain, and a signaling domain comprising a CD3c signaling domain and a CD3ζ signaling domain. The amino acid sequence of this chimeric antigen receptor comprises the following amino acid sequence: LFNQEVQIPLTESYCGPCPKNWICYKNN-CYQFFDESKNWYESQASCMSQNASLLKVYS KEDQDLLKLVKSYHWMGLVHIPTNGSWQWEDGSIL-SPNLLTIIEMQKGDCALYASSFK GYIENCSTPN-TYICMQRTVTTTPAPRPPTPAPTIASQPLSLRPEACR-PAAGGAVHTRGLDF ACDFWVLVVVGGVLACYSLLVTVAFIIFWVKR-GRKKLLYIFKQPFMRPVQTTQEEDGC SCRFPEEEEGGCEKNRKAKAKPVTRGAGAG-GRQRGQNKERPPPVPNPDYEPIRKGQRD LYSGLLRVKFSRSADAPAYQQGQNQLYNELNLGR-REEYDVLDKRRGRDPEMGGKPRR KNPQEGLY-NELQKDKMAEAYSEIGMKGERRRGKGHDGLYQGL-STATKDTYDALHMQ ALPPR (SEQ ID NO: 74). In one aspect, CAR7 is encoded by the following nucleotide sequence:

```
                                                         (SEQ ID NO: 75)
   1   cgcggaatga aagaccccac ctgtaggttt ggcaagctag cttaagtaac gccatttgc 61   aaggcatgga aaatacataa ctgagaatag agaagttcag atcaaggtta ggaacagaga 121   gacagcagaa tatgggccaa acaggatatc tgtggtaagc agttcctgcc ccggctcagg 181   gccaagaaca gatggtcccc agatgcggtc ccgccctcag cagtttctag agaaccatca 241   gatgtttcca gggtgcccca aggacctgaa atgaccctgt gccttatttg aactaaccaa 301   tcagttcgct tctcgcttct gttcgcgcgc ttctgctccc cgagctcaat aaaagagccc 361   acaacccctc actcggcgcg ccagtccttc gaagtagatc tttgtcgatc ctaccatcca 421   ctcgacacac cgccagcgg  ccgctgccaa gcttccgagc tctcgaatta attcacgccg 481   ccaccatggc tcttcctgtg acagctcttc tgctgcccct ggccctgctt ctgcatgctg 541   ctagacctga gcaaaagttg atttctgagg aagacctcgc cggcagttta ttcaaccaag 601   aagtccaaat tcccttgacc gaaagttact gtggcccatg tcctaagaac tggatatgtt 661   acaaaaataa ctgttaccaa ttcttcgatg aatctaagaa ttggtatgag agccaggctt 721   cttgtatgtc tcaaaatgcc agccttctta agtatacag  caaagaggac caggatttac 781   ttaaactggt gaagtcatat cattggatgg gactagtaca cattccaaca aatggatctt 841   ggcagtggga agacggctcc attctctcac ccaacctact aacaataatt gaaatgcaga 901   agggagactg tgcactctat gcatcgagct ttaaaggcta tatagaaaac tgttcaactc 961   caaatacata tatttgcatg caaaggactg tgaccacgac gccagcgccg cgaccaccaa 1021   caccggcgcc caccatcgcg tcgcaacccc tgtccctgag gcctgaagcg tgccggccag 1081   cggcgggcgg cgcagtgcac acgagagggc tggacttcgc ctgtgatttt tgggtgctgg 1141   tggtggttgg tggagtcctg gcttgctata gcttgctagt aacagtggcc tttattattt 1201   tctgggtcaa acggggcaga aagaaactcc tgtatatatt caaacaacca tttatgagac 1261   cagtacaaac tactcaagag gaagatggct gtagctgccg atttccagaa gaagaagaag 1321   gaggatgtga aaagaaccga aaagcaaaag ccaagcctgt tacaagagga gcaggggcag 1381   gaggccgaca gagagggcaa aacaaagaaa ggccccgcc  cgtcccaaac ccggattatg 1441   agccaattag gaagggtcag agagacctgt attctgggct cctgagagtg aagttcagca 1501   ggagcgcaga cgccccgcg  taccagcaag ggcagaacca gctctataac gagctcaatc 1561   taggacgaag agaggagtac gatgttttgg acaagaggcg tggccgggac cctgagatgg 1621   ggggaaagcc gagaaggaag aaccctcagg aaggcctgta caatgaactg cagaaagata 1681   agatggcgga ggcctacagt gagattggga tgaaaggcga gcgccggagg ggcaaggggc 1741   acgatggcct ttaccagggt ctcagtacag ccaccaagga cacctacgac gcccttcaca 1801   tgcaagctct gccccctcgc tga
```

CAR7 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 75). In certain aspects, the nucleic acid sequence of (SEQ ID NO: 75) may be modified to remove sequences encoding the Myc (human c-Myc proto-oncogene) epitope tag and linker between the Myc tag and the NKG2D extracellular domain. The nucleic acid sequence of (SEQ ID NO: 75) encodes for a CD8a signal peptide at positions 486-548, which signal peptide may be substituted for a different signal peptide.

An eight construct, termed NKG2D CAR8 comprises from N to C-terminus a NKG2D extracellular domain, a CD8alpha hinge, a CD28 transmembrane domain, a 4-1BB intercellular domain, and a signaling domain comprising a CDR signaling domain and a CD3ζ signaling domain. The amino acid sequence of this chimeric antigen receptor comprises the following amino acid sequence: LFNQEVQIPLTESYCGPCPKNWICYKNN-CYQFFDESKNWYESQASCMSQNASLLKVYS KEDQDLLKLVKSYHWMGLVHIPTNGSWQWEDGSIL-SPNLLTIIEMQKGDCALYASSFK GYIENCSTPN-TYICMQRTVTTTPAPRPPTPAPTIASQPLSLRPEACR-PAAGGAVHTRGLDF ACDFWVLVVVGGVLACYSLLVTVAFIIFWVKR-GRKKLLYIFKQPFMRPVQTTQEEDGC SCRFPEEEEGGCEKNRKAKAKPVTRGAGAG-GRQRGQNKERPPPVPNPDYEPIRKGQRD LYSGLNQRRILRVKFSRSADAPAYQQGQNQLY-NELNLGRREEYDVLDKRRGRDPEMG GKPRRKNPQEGLYNELQKDKMAEAYSEI-GMKGERRRGKGHDGLYQGLSTATKDTYD ALHMQALPPR (SEQ ID NO: 76). In one aspect, CAR8 is encoded by the following nucleotide sequence:

```
                                                     (SEQ ID NO: 77)
   1  cgcggaatga aagaccccac ctgtaggttt ggcaagctag cttaagtaac gccattttgc 61  aaggcatgga aaatacataa ctgagaatag agaagttcag atcaaggtta ggaacagaga 121  gacagcagaa tatgggccaa acaggatatc tgtggtaagc agttcctgcc ccggctcagg 181  gccaagaaca gatggtcccc agatgcggtc ccgccctcag cagtttctag agaaccatca 241  gatgtttcca gggtgcccca aggacctgaa atgaccctgt gccttatttg aactaaccaa 301  tcagttcgct tctcgcttct gttcgcgcgc ttctgctccc cgagctcaat aaaagagccc 361  acaacccctc actcggcgcg ccagtccttc gaagtagatc tttgtcgatc ctaccatcca 421  ctcgacacac ccgccagcgg ccgctgccaa gcttccgagc tctcgaatta attcacgccg 481  ccaccatggc tcttcctgtg acagctcttc tgctgccct ggccctgctt ctgcatgctg 541  ctagacctga gcaaaagttg atttctgagg aagacctcgc cggcagttta ttcaaccaag 601  aagtccaaat tccttgacc gaaagttact gtggcccatg tcctaagaac tggatatgtt 661  acaaaaataa ctgttaccaa ttcttcgatg aatctaagaa ttggtatgag gccaggctt 721  cttgtatgtc tcaaaatgcc agccttctta agtatacag caaagaggac caggatttac 781  ttaaactggt gaagtcatat cattggatgg gactagtaca cattccaaca aatggatctt 841  ggcagtggga agacggctcc attctctcac ccaacctact aacaataatt gaaatgcaga 901  agggagactg tgcactctat gcatcgagct ttaaaggcta tatagaaaac tgttcaactc 961  caaatacata tatttgcatg caaaggactg tgaccacgac gccagcgccg cgaccaccaa 1021  caccggcgcc caccatcgcg tcgcaacccc tgtccctgag gcctgaagcg tgccggccag 1081  cggcgggcgg cgcagtgcac acgagagggc tggacttcgc ctgtgatttt tgggtgctgg 1141  tggtggttgg tggagtcctg gcttgctata gcttgctagt aacagtggcc tttattattt 1201  tctgggtcaa acggggcaga aagaaactcc tgtatatatt caaacaacca tttatgagac 1261  cagtacaaac tactcaagag gaagatggct gtagctgccg atttccagaa gaagaagaag 1321  gaggatgtga aaagaaccgc aaagcaaagg caaaacccgt cacacgagga gcgggcgcag 1381  ggggacgaca acgcggtcag aataaggaac gcccgcctcc agtaccaaat ccagattatg 1441  aaccaattcg aagggacaa cgcgatctct actccggtct caatcagagg cgaattctga 1501  gagtgaagtt cagcaggagc gcagacgccc ccgcgtacca gcaagggcag aaccagctct 1561  ataacgagct caatctagga cgaagagagg agtacgatgt tttggacaag aggcgtggcc 1621  gggaccctga gatgggggga aagccgagaa ggaagaaccc tcaggaaggc ctgtacaatg 1681  aactgcagaa agataagatg gcggaggcct acagtgagat tgggatgaaa ggcgagcgcc 1741  ggaggggcaa ggggcacgat ggcctttacc agggtctcag tacagccacc aaggacacct 1801  acgacgccct tcacatgcaa gctctgcccc ctcgctga
```

CAR8 can be encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to (SEQ ID NO: 77). In certain aspects, the nucleic acid sequence of (SEQ ID NO: 77) may be modified to remove sequences encoding the Myc (human c-Myc proto-oncogene) epitope tag and linker between the Myc tag and the NKG2D extracellular domain. The nucleic acid sequence of (SEQ ID NO: 77) encodes for a CD8a signal peptide at positions 486-548, which signal peptide may be substituted for a different signal peptide.

Example 2

Transduction Efficiency

Retroviral vectors were used for all T-cell transductions. An engineered TCR targeting the HPV16+E7$_{11-19}$ epitope and was used for singular or co-transduction with the NKG2D CAR constructs (Jin B. Y. et al., 2018 JCI Insight). Previously cryopreserved PBMCs obtained from healthy donors were thawed and activated with anti-CD3 for 48 hours in Optimizer T cell media supplemented with 300 IU of IL-2. The PBMCs were transduced with retrovirus containing the engineered TCR targeting the HPV16+ E7$_{11-19}$ epitope (referred to in this Example, and the Examples below, as HPV-TCR), the NKG2D CAR, or both constructs. Transduced T cells were expanded for 10 days in Optimizer T cell media supplemented with IL-7 (10 ng/mL), IL-15 (10 ng/mL), and Akt VIII inhibitor (AKTi, 1 µM). Transduction efficiency was measured by flow cytometry at day 8 and day 15 post T cell activation. Antibodies to detect TCR transduction efficiency include anti-mouse TCRβ clone H57-597 (BioLegend) and antibodies to detect NKG2D transduction efficiency include anti-human CD314 clone 1D11 (BioLegend). All flow cytometry data was collected on LSR-Fortessa (BD LSR Fortessa™) with BD FACSDiva™ software and data was analyzed using FlowJo (all from BD Sciences). All antibody staining was performed at 4° C. in PBS containing 1% BSA.

Table 4 shows the expression level (measured as mean fluorescence intensity (MFI) and % positive cells) of transduced and non-transduced T cells after day 8 and 15 of culture by flow cytometry. High transduction efficiency was observed in all constructs. A small NKG2D+ only population is present in the HPV-TCR+NKG2D CAR1 and HPV-TCR+NKG2D CAR2 groups.

Table 19 shows the expression level (as mean fluorescence intensity (MFI) and % positive cells) of transduced and non-transduced T cells after day 7/8 of culture based on Myc staining and expression measurement by flow cytometry. High transduction efficiency was observed in all constructs.

TABLE 19

Expression level and percentage of transgene in transduced and non-transduced T-cells from two donors

|  | Donor 1 % Myc | Donor 2 % Myc |
|---|---|---|
| CAR3 | 98.6 | 96.9 |
| CAR6 | 99.7 | 99.6 |
| CAR5 | 80.1 | 62.1 |
| CAR4 | 99.2 | 98.7 |
| CAR7 | 98.8 | 98.4 |
| CAR8 | 98.9 | 98.6 |
| NTD | 0.15 | 0.2 |

Example 3

Expansion and Viability

Cell expansion was measured by the Vi-Cell XR Cell Counter (Beckman Coulter) and cell viability was measured by staining cells with Live/Dead Blue (ThermoFisher) in PBS for 20 minutes on ice and analyzed by flow cytometry at day 8 and day 15 post T cell activation (Table 5). Transformed T cell was activated as described in Example 2. Table 5 shows the expansion and cell viability of transduced and non-transduced T cells cultured with Optimizer media supplemented with IL-7, IL-15, and AKTi. NKG2D CAR1 only, NKG2D CAR2 only, HPV-TCR+NKG2D CAR1 and HPV-TCR+NKG2D CAR2 displayed greater levels of proliferation than HPV-TCR only or non-transduced T cells.

TABLE 5

Fold expansion and viability of transduced and non-transduced PBMCs gated on CD3+ T cells

| Experimental Group | Viability | | Fold expansion |
|---|---|---|---|
|  | Day 8 | Day 15 | Day 8 |
| Non-transduced T cells | 98.2% | 96.5% | 51× |
| HPV-TCR only | 94.2% | 88.9% | 42× |
| NKG2D CAR1 only | 85.1% | 74.3% | 81× |
| NKG2D CAR2 only | 89.4% | 88.8% | 74× |

TABLE 4

Expression level and percentage of transgene in transduced and non-transduced PBMCs gated on live CD3+ T cells

| Experimental Group | mTCRβ MFI | | % positive | | NKG2D MFI | | % positive | |
|---|---|---|---|---|---|---|---|---|
|  | Day 8 | Day 15 | Day 8 | Day 15 | Day 8 | Day 15 | Day 8 | Day 15 |
| Non-transduced T cells | 21 | 18 | 0.1% | 0.1% | 1026 | 1145 | 23.5% | 20.1% |
| HPV-TCR only | 55481 | 59065 | 82.5% | 84.5% | 1284 | 1354 | 21.6% | 21.1% |
| NKG2D CAR1 only | 14 | 33 | 0.4% | 0.6% | 25733 | 22040 | 96.6% | 97.4% |
| NKG2D CAR2 only | 10 | 25 | 0.5% | 0.3% | 16637 | 15327 | 91.7% | 86.8% |
| HPV-TCR + NKG2D CAR 1 | 48476 | 50264 | 70.1% | 71.4% | 22635 | 20930 | 97.5% | 94.7% |
| HPV-TCR + NKG2D CAR 2 | 46045 | 48190 | 68.8% | 69.5% | 17188 | 16418 | 92.9% | 86.3% |

TABLE 5-continued

Fold expansion and viability of transduced and non-transduced PBMCs gated on CD3+ T cells

| Experimental Group | Viability | | Fold expansion |
|---|---|---|---|
| | Day 8 | Day 15 | Day 8 |
| HPV-TCR + NKG2D CAR1 | 90.4% | 78.5% | 75× |
| HPV-TCR + NKG2D CAR2 | 88.6% | 83.0% | 68× |

Example 4

Product Attribute Determination

Memory phenotype and CD4/CD8 ratio was measured by flow cytometry at day 8 post T cell activation (Table 6). Antibodies used to assess memory phenotype include anti-human CD45RA clone HI100 (BioLegend), anti-human CD45RO clone UCHL1 (BioLegend), anti-human CCR7 clone G043H7 (BioLegend), anti-human CD62L clone DREG-56 (BioLegend). Antibodies used to assess CD4/CD8 ratio include anti-human CD3 clone SK7 (BioLegend), anti-human CD4 clone RPA-T4 (BioLegend), and anti-human CD8 clone SK1 (BioLegend). Transformed T cells were activated as described in Example 2. Memory phenotype was assessed as follows: naïve T cells (CD45RA+ CD45RO− CCR7+ CD62L+); central memory T cells (CD45RA− CD45RO+ CCR7+ CD62L+); effector memory T cells (CD45RA− CD45RO+ CCR7− CD62L−); terminal effector T cells (CD45RA+ CD45RO− CCR7− CD62L−). All flow cytometry data was collected on LSR-Fortessa (BD LSR Fortessa™) with BD FACSDiva™ software and data was analyzed using FlowJo (all from BD Sciences). All antibody staining was performed at 4° C. in PBS containing 1% BSA.

Shown in Table 6 is the CD4/CD8 ratio and memory phenotype of transduced and non-transduced CD3+ T cells cultured with TC Media with supplemental IL-2 after day 8. There were no significant changes in the CD4/CD8 ratio between transduced T cells and non-transduced T cells. Non-transduced and HPV-TCR only transduced T cells exhibited a larger naïve T cell compartment than T cells transduced with NKG2D CAR1 only, NKG2D CAR2 only, HPV-TCR+NKG2D CAR1, or HPV-TCR+NKG2D CAR2. In addition, Non-transduced and HPV-TCR only transduced T cells exhibited a smaller memory T cell compartment than T cells transduced with NKG2D CAR1 only, NKG2D CAR2 only, HPV-TCR+NKG2D CAR1, or HPV-TCR+NKG2D CAR2.

Example 5

Cytotoxicity

HPV-TCR transduced T cells have been previously shown to effectively eliminate HPV16+ tumor cell lines and produce high levels of IFNγ. Sequencing of patient tumors from a Phase I clinical trial with the HPV-TCR (Nagarsheth N. B. et al., 2021 Nat Med) suggest that tumors are highly heterogeneous and can exhibit mutations in MHC-I antigen processing and presentation pathways, thereby rendering them resistant to HPV-TCR engineered adoptive TCR-T therapy. To model the patient tumor data, a HPV16+ tumor cell line (CaSki) was engineered to lack A*02:01 by knocking out β2M (β2MKO) using a CRISPR-Cas9 system (Vakulskas C A et al., 2018 Nature). Additionally, the SiHa HPV16+ tumor cell line, which normally lacks HLA-A*02:01, was engineered to overexpress A*02:01 using a retroviral vector. The CaSki and SiHa tumor cell lines were chosen due to high and low E7 expression, respectively. Killing of these tumor cell lines with or without HLA-A*02:01 intact with non-transduced and transduced PBMCs was assessed using the xCELLigence RTCA MP (Agilent Technologies) platform the various effector-to-target (E:T) ratios shown in Table 7 and 8.

Table 7 shows the results of transduced T cells (see Example 2) that were sorted at day 8 and then co-cultured at various E:T ratios with WT or β2MKO CaSki cells at day 10 in a 96 well xCELLigence plate. Impedance values (IV) were measured 72 hours later. Control IV represents impedance value of non-transduced T cells, and Experimental IV represents impedance value of either HPV-TCR only, NKG2D CAR1 only, NKG2D CAR2 only, HPV-TCR+ NKG2D CAR1, or HPV-TCR+NKG2D CAR2. Percent cytotoxicity was calculated by the following equation:

$$\% \text{ Cytotoxicity} = 1 - (\text{Control } IV - \text{Experimental } IV) * 100$$

TABLE 6

CD4/CD8 ratio and memory phenotype of transduced and non-transduced PBMCs gated on live CD3+ T cells

| Experimental Group | CD4/CD8 ratio | | Memory phenotype | | | |
|---|---|---|---|---|---|---|
| | CD4 | CD8 | Naïve | TCM | TEM | TE |
| Non-transduced | 51.8% | 48.2% | 22.7% | 46.0% | 14.0% | 5.3% |
| HPV-TCR only | 45.7% | 54.3% | 24.3% | 45.0% | 15.0% | 5.8% |
| NKG2D CAR1 only | 46.8% | 53.2% | 3.5% | 63.0% | 28.1% | 9.4% |
| NKG2D CAR2 only | 44.7% | 55.3% | 8.5% | 56.4% | 25.7% | 5.4% |
| HPV-TCR + NKG2D CAR1 | 48.1% | 51.9% | 3.1% | 61.6% | 28.2% | 7.1% |
| HPV-TCR + NKG2D CAR2 | 47.2% | 52.8% | 7.2% | 57.4% | 28.5% | 6.9% |

TABLE 7

Killing of WT and β2MKO CaSki cells by transduced
and non-transduced PBMCs at different E:T ratios

|  | WT CaSki | | | β2MKO CaSki | | |
| --- | --- | --- | --- | --- | --- | --- |
| Experimental Group | 3:1 ratio | 1:1 ratio | 1:3 ratio | 3:1 ratio | 1:1 ratio | 1:3 ratio |
| Non-transduced | 0.0% | 0.0% | 0.0% | 0.0% | 0.0% | 0.0% |
| HPV-TCR only | 102.5% | 101.5% | 96.1% | 13.6% | 11.2% | 7.5% |
| NKG2D CAR1 only | 103.0% | 101.4% | 96.7% | 102.6% | 101.6% | 97.0% |
| NKG2D CAR2 only | 103.2% | 104.0% | 101.3% | 104.4% | 98.1% | 93.5% |
| HPV-TCR + NKG2D CAR1 | 105.1% | 102.3% | 98.4% | 102.4% | 103.8% | 96.5% |
| HPV-TCR + NKG2D CAR2 | 101.8% | 99.3% | 89.2% | 101.6% | 100.3% | 89.8% |

Table 8 shows the results of transduced T cells (see Example 2) that were sorted at day 8 and then co-cultured at various E:T ratios with WT or A*02:01 expressing SiHa cells at day 10 in a 96-well xCELLigence E-plate. Impedance values (IV) were measured 72 hours later and percent cytotoxicity was calculated is described above.

TABLE 8

Killing of SiHa cells by transduced and non-transduced PBMCs

|  | WT SiHa | | | A*02 SiHa | | |
| --- | --- | --- | --- | --- | --- | --- |
| Experimental Group | 3:1 ratio | 1:1 ratio | 1:3 ratio | 3:1 ratio | 1:1 ratio | 1:3 ratio |
| Non-transduced | 0.0% | 0.0% | 0.0% | 0.0% | 0.0% | 0.0% |
| HPV-TCR only | 13.7% | 8.9% | 2.1% | 99.5% | 78.3% | 57.1% |
| NKG2D CAR1 only | 102.5% | 99.5% | 94.1% | 102.1% | 101.1% | 84.1% |
| NKG2D CAR2 only | 103.6% | 97.4% | 91.1% | 99.8% | 93.5% | 75.3% |
| HPV-TCR + NKG2D CAR1 | 101.5% | 99.8% | 88.6% | 104.2% | 100.8% | 87.0% |
| HPV-TCR + NKG2D CAR2 | 102.3% | 93.6% | 77.5% | 102.2% | 98.5% | 79.4% |

HPV-TCR transduced T cells successfully eliminated WT CaSki and A*02 SiHa cell lines, but were unable to eliminate β2M KO CaSki or WT SiHa cell lines. Importantly, NKG2D CAR transduced T cells and NKG2D CAR co-transduced with HPV-TCR T cells were able to successfully kill CaSki and SiHa cell lines, independent of their HLA-A*02:01 status.

Example 6

Cytokine Production

Cytokine production was measured by retrieving supernatants from the xCELLigence 96-well plates used in example 5 after 24 hours of culture. The cytokine levels were measured using a Meso Sector S 600 platform (Institute for Biopharmaceutical Research, Inc.). IFNγ production from HPV-TCR+NKG2D CAR T cells was similar to HPV-TCR transduced cells when co-cultured with WT or A*02 SiHa cells. However, IFNγ production from HPV-TCR+NKG2D CAR T cells increased compared to HPV-TCR transduced T cells when co-cultured with β2MKO CaSki or WT SiHa cells, which correlated with cytotoxicity data (see Table 9 and Table 10). These data showed that NKG2D CAR T cells secrete nominal levels of IFNγ when HPV-TCR transduced T cells eliminate target cells, but produce sufficient IFNγ when HPV-TCR transduced T cells did not eliminate target cells. Interestingly, NKG2D CAR1 and HPV-TCR+NKG2D CAR1 transduced T cells produce greater levels of IFNγ than NKG2D CAR2 or HPV-TCR+NKG2D CAR2 transduced T cells.

Table 9 shows the results of transduced T cells that were sorted at day 8 and then co-cultured at various E:T ratios with WT or β2MKO CaSki cells at day 10 in a 96-well xCELLigence E-plate. At 24 hours, media supernatants were extracted and processed for determining IFNγ concentration (pg/mL) using the Meso Sector S 600 platform according to the manufacturer's directions.

TABLE 9

IFNγ production of transduced and non-
transduced PBMCs co-cultured with CaSki cells

|  | WT CaSki | | | β2MKO CaSki | | |
| --- | --- | --- | --- | --- | --- | --- |
| Experimental Group | 3:1 ratio | 1:1 ratio | 1:3 ratio | 3:1 ratio | 1:1 ratio | 1:3 ratio |
| HPV-TCR only | 1721 | 641 | 273 | 130 | 90 | 40 |
| NKG2D CAR1 only | 4486 | 2931 | 1053 | 5024 | 2820 | 1306 |
| NKG2D CAR2 only | 2836 | 1063 | 403 | 1989 | 777 | 262 |
| HPV-TCR + NKG2D CAR1 | 3721 | 1369 | 523 | 4191 | 2067 | 895 |
| HPV-TCR + NKG2D CAR2 | 1467 | 561 | 212 | 1567 | 622 | 192 |

Table 10 shows the results of transduced T cells that were sorted at day 8 and then co-cultured at various E:T ratios with WT or A*02 SiHa cells at day 10 in a 96-well xCELLigence E-plate. At 24 hours, media supernatants were extracted and processed for determining IFNγ concentration (pg/mL) using the Meso Sector S 600 platform according to the manufacturer's directions.

TABLE 10

IFNγ production of transduced and non-transduced PBMCs co-cultured with SiHa cells

| | WT SiHa | | | A*02 SiHa | | |
|---|---|---|---|---|---|---|
| Experimental Group | 3:1 ratio | 1:1 ratio | 1:3 ratio | 3:1 ratio | 1:1 ratio | 1:3 ratio |
| HPV-TCR only | 30 | 12 | 3 | 155 | 75 | 45 |
| NKG2D CAR1 only | 7538 | 3968 | 1970 | 7271 | 4145 | 1380 |
| NKG2D CAR2 only | 4638 | 1300 | 342 | 4034 | 1554 | 560 |
| HPV-TCR + NKG2D CAR1 | 5563 | 2522 | 1149 | 6518 | 3223 | 1296 |
| HPV-TCR + NKG2D CAR2 | 3240 | 901 | 232 | 3223 | 938 | 284 |

Example 7

Long Term Expansion and Exhaustion of Transduced T Cells

Repeated antigen stimulation in a long-term killing assay functionally exhausts the T cells and is believed to correlate with in vivo efficacy. To complete a serial antigen stimulation assay, target cells (WT CaSki, β2MKO CaSki, WT SiHa, or A*02 SiHa) were added to transduced T cells (see Example 2) every 2-3 days. At the fifth stimulation, cytotoxicity of either WT CaSki, β2MKO CaSki, WT SiHa, or A*02 SiHa was assessed at the various E:T ratios shown in Tables 11 and 12 using the xCELLigence RTCA MP platform. Despite the addition of the NKG2D CAR, HPV-TCR+ NKG2D CAR transduced T cells successfully eliminated its targets after serial stimulation and exhibited high levels of expansion compared to HPV-TCR only transduced T cells (see Table 11, Table 12).

Table 11 shows the results of transduced T cells that were sorted at day 8 and then co-cultured at a 3:1 E:T ratio with WT CaSki cells at day 10. WT CaSki cells were then added every 2-3 days. At the fifth stimulation, T cells were co-cultured at various E:T ratios with WT or β2MKO CaSki cells in a 96 well xCELLigence plate. Impedance values (IV) were measured 72 hours later and cytotoxicity was calculated as described above.

TABLE 11

Killing of CaSki cells by transduced and non-transduced PBMCs after 5 rounds of antigen stimulation

| | WT CaSki | | | β2MKO CaSki | | |
|---|---|---|---|---|---|---|
| Experimental Group | 3:1 ratio | 1:1 ratio | 1:3 ratio | 3:1 ratio | 1:1 ratio | 1:3 ratio |
| HPV-TCR only | 86.8% | 44.2% | 12.5% | 11.2% | 4.1% | −3.3% |
| NKG2D CAR1 only | 100.4% | 99.6% | 75.6% | 102.4% | 90.1% | 57.1% |
| NKG2D CAR2 only | 101.1% | 92.5% | 44.9% | 98.2% | 81.3% | 36.1% |
| HPV-TCR + NKG2D CAR1 | N.D | N.D. | N.D. | N.D. | N.D. | N.D. |
| HPV-TCR + NKG2D CAR2 | 102.4% | 97.1% | 62.4% | 95.0% | 73.2% | 26.7% |

Table 12 shows the results of transduced T cells that were sorted at day 8 and then co-cultured at a 3:1 E:T ratio with WT CaSki cells at day 10. WT CaSki cells were then added every 2-3 days. At the fifth stimulation, T cells were co-cultured at various E:T ratios with WT or A*02 SiHa cells in a 96 well xCELLigence plate. Impedance values (IV) were measured 72 hours later and cytotoxicity was calculated cytotoxicity was calculated as described above.

TABLE 12

Killing of SiHa cells by transduced and non-transduced PBMCs after 5 rounds of antigen stimulation

| | WT SiHa | | | A*02 SiHa | | |
|---|---|---|---|---|---|---|
| Experimental Group | 3:1 ratio | 1:1 ratio | 1:3 ratio | 3:1 ratio | 1:1 ratio | 1:3 ratio |
| HPV-TCR only | 4.7% | −2.1% | −6.2% | 9.1% | −2.2% | −5.4% |
| NKG2D CAR1 only | 99.7% | 82.5% | 40.9% | 98.8% | 87.1% | 39.2% |
| NKG2D CAR2 only | 92.5% | 80.4% | 23.6% | 94.1% | 65.2% | 21.7% |
| HPV-TCR + NKG2D CAR1 | N.D. | N.D. | N.D. | N.D. | N.D. | N.D. |
| HPV-TCR + NKG2D CAR2 | 91.8% | 78.1% | 29.0% | 90.5% | 70.1% | 19.6% |

Example 8

Cytotoxicity and Cytokine Production of NKG2D CAR and NKG2D CAR Co-Expressed with HPV-TCR Co-Cultured with HPV16+ Tumor Cell Lines To address safety of the NKG2D based CARs, NKG2D CAR1 only, NKG2D CAR2 only, HPV-TCR+NKG2D CAR1, and HPV-TCR+NKG2D CAR2 transduced T cells, were co-cultured with either the C33A cell line, which is largely NKG2D ligand negative, and primary normal cervical epithelial cells at various E:T ratios as shown in Table 13 and Table 14. Primary normal cervical epithelial cells were chosen due to higher NKG2D ligand expression. Cytotoxicity data from the xCELLigence RTCA MP platform and IFNγ production from the Meso Sector S 600 platform indicated low reactivity to both C33A and primary normal cervical epithelial cells. These data are suggestive that NKG2D CAR2 has a strong safety profile and is unlikely to exhibit off-target effects.

Table 13 shows the results of transduced T cells that were sorted at day 8 and then co-cultured at various E:T ratios with C33A or primary normal cervical epithelial cells at day 10 in a 96-well xCELLigence E-plate. At 24 hours, media supernatants were extracted and processed for determining IFNγ concentration (pg/mL) using the Meso Sector S 600 platform.

TABLE 13

Killing of C33A and primary normal cervical epithelial cells by transduced and non-transduced PBMCs

| Experimental Group | C33A | | | Primary normal cervical | | |
|---|---|---|---|---|---|---|
| | 3:1 ratio | 1:1 ratio | 1:3 ratio | 3:1 ratio | 1:1 ratio | 1:3 ratio |
| Non-transduced T cells | 0.0% | 0.0% | 0.0% | 0.0% | 0.0% | 0.0% |
| HPV-TCR only | 7.6% | 4.5% | −4.3% | 3.3% | 3.0% | −8.1% |
| NKG2D CAR1 only | 30.1% | 1.6% | −4.5% | 17.2% | 1.8% | −5.4% |
| NKG2D CAR2 only | 9.5% | 2.5% | −6.2% | 7.5% | 2.7% | −2.9% |
| HPV-TCR + NKG2D CAR1 | 21.0% | 8.5% | −6.4% | 12.2% | 4.5% | −5.6% |
| HPV-TCR + NKG2D CAR2 | 9.7% | 5.9% | −5.4% | 6.0% | 1.1% | −4.3% |

Table 14 shows the results of transduced T cells that were sorted at day 8 and then co-cultured at various E:T ratios with C33A cell line or primary normal cervical epithelial cells at day 10 in a 96-well xCELLigence E-plate. At 24 hours, media supernatants were extracted and processed for determining IFNγ concentration (pg/mL) using the Meso Sector S 600 platform.

TABLE 14

IFNγ production of transduced and non-transduced PBMCs co-cultured with either C33A cell line or primary normal cervical epithelial cells

| Experimental Group | C33A | | | Primary normal cervical | | |
|---|---|---|---|---|---|---|
| | 3:1 ratio | 1:1 ratio | 1:3 ratio | 3:1 ratio | 1:1 ratio | 1:3 ratio |
| Non-transduced T cells | 50 | 48 | 47 | 53 | 49 | 37 |
| HPV-TCR only | 67 | 54 | 61 | 60 | 53 | 49 |
| NKG2D CAR1 only | 549 | 251 | 109 | 378 | 204 | 74 |
| NKG2D CAR2 only | 134 | 85 | 62 | 104 | 74 | 52 |
| HPV-TCR + NKG2D CAR1 | 309 | 159 | 65 | 268 | 73 | 37 |
| HPV-TCR + NKG2D CAR2 | 121 | 84 | 67 | 142 | 73 | 48 |

Example 9

In Vivo Efficacy of NKG2D CAR Against HPV16+ Tumors in a Mouse Xenograft Model To determine the in vivo efficacy of HPV-TCR only, NKG2D CAR only, and HPV-TCR+NKG2D CAR in eliminating both WT and β2MKO HPV16+ solid tumors, 5E6 WT CaSki and 5E6 β2MKO CaSki cells were implanted subcutaneously on the left and right flanks, respectively, of 6-8-week-old female NSG mice (NOD.Cg− Prkdcscid Il2rgtm1Wjl/SzJ). Five study groups were included: vehicle control (PBS), non-transduced T cells (NTD), HPV-TCR only, NKG2D CAR2 only, and HPV-TCR+NKG2D CAR2. $20 \times 10^6$ T cells per mouse were adoptively transferred at day 6, when the tumor volume of WT CaSki cells had reached approximately 70 mm$^3$ and the β2MKO CaSki cells had reached approximately 30 mm$^3$. No IL-2 supplementation was added. Tumors were measured every 3-4 days using digital calipers and mouse weight was recorded. Peripheral blood was collected 24-hours post T cell adoptive transfer, and then every week afterward. Persistence of T cells in the peripheral blood was characterized through flow cytometry. Antibodies to assess T cell persistence in the peripheral blood include anti-mouse CD45 clone 30-F11 (BioLegend), anti-human CD45 clone HI30 (BioLegend), anti-human CD4 clone RPA-T4, (BioLegend), anti-human CD8 clone SK1 (BioLegend), anti-human CD279 clone EH12.2H7 (BioLegend), anti-human HLA-DR clone L243 (BioLegend), anti-mouse TCRβ clone H57-597 (BioLegend), anti-human CD314 clone 1D11 (Biolegend), and L/D Blue (ThermoFisher). All flow cytometry data was collected on LSR-Fortessa (BD LSR Fortessa™) with BD FACSDiva™ software and data was analyzed using FlowJo (all from BD Sciences). All antibody staining was performed at 4° C. in PBS containing 1% BSA. The study duration was 62 days. Overall, the HPV-TCR was able to control tumor growth of WT CaSki cells on the left flank, but did not show any sign of tumor control of the β2MKO CaSki cells implanted on the right flank. In contrast, NKG2D CAR2 only and HPV-TCR+ NKG2D CAR2 successfully controlled tumor growth of both WT and β2MKO CaSki cells (see Table 15, Table 16). Furthermore, weight of tumor-bearing mice did not fluctuate significantly for the first several weeks post adoptive T cell transfer, until the mice had to come off the study due to tumor size. (see Table 17). Despite no observable tumors in all mice receiving NKG2D CAR2 only or HPV-TCR+ NKG2D CAR2 T cells, most of the mice demonstrated relapse in tumor growth, suggesting a lack of persistence of the transduced T cells. This is further supported by the absence of transduced T cells in the peripheral blood three weeks after adoptive T cell transfer (see Table 18).

TABLE 15

Tumor volume of WT CaSki cells over time

| | Days post tumor inoculation | | | | | | | | | | | | |
|---|---|---|---|---|---|---|---|---|---|---|---|---|---|
| | 6 | 8 | 11 | 13 | 15 | 18 | 20 | 22 | 25 | 27 | 29 | 32 | 34 |
| Vehicle | 77 | 78 | 97 | 107 | 126 | 251 | 316 | 343 | 394 | 526 | 607 | 625 | 665 |
| | 85 | 87 | 96 | 111 | 180 | 301 | 402 | 440 | 501 | 541 | 652 | 704 | 793 |
| | 72 | 75 | 76 | 86 | 158 | 166 | 232 | 331 | 406 | 463 | 531 | 633 | 663 |
| | 63 | 70 | 80 | 89 | 168 | 191 | 208 | 239 | 253 | 326 | 398 | 496 | 503 |
| | 63 | 67 | 71 | 93 | 148 | 236 | 327 | 342 | 452 | 500 | 537 | 549 | 676 |
| | 90 | 97 | 100 | 108 | 111 | 134 | 210 | 271 | 350 | 392 | 463 | 536 | 551 |
| | 64 | 67 | 72 | 78 | 121 | 169 | 217 | 302 | 328 | 368 | 488 | 500 | 613 |
| | 66 | 72 | 73 | 75 | 111 | 199 | 248 | 384 | 420 | 506 | 536 | 646 | 683 |
| NTD | 88 | 98 | 106 | 112 | 148 | 288 | 345 | 460 | 591 | 695 | 708 | 758 | 760 |
| | 68 | 72 | 76 | 84 | 105 | 256 | 340 | 468 | 555 | 660 | 705 | 759 | 880 |
| | 70 | 74 | 74 | 80 | 90 | 241 | 250 | 281 | 305 | 363 | 398 | 564 | 747 |
| | 67 | 73 | 79 | 91 | 129 | 255 | 312 | 543 | 573 | 599 | 616 | 647 | 684 |
| | 64 | 74 | 76 | 78 | 79 | 120 | 148 | 162 | 200 | 291 | 429 | 459 | 264 |
| | 79 | 87 | 91 | 104 | 116 | 309 | 331 | 443 | 529 | 581 | 716 | 737 | 878 |
| | 72 | 77 | 86 | 88 | 114 | 295 | 319 | 356 | 435 | 527 | 567 | 623 | 635 |
| | 63 | 65 | 79 | 85 | 90 | 242 | 253 | 330 | 434 | 489 | 490 | 492 | 499 |
| HPV-TCR only | 73 | 76 | 79 | 33 | 32 | 16 | 11 | 12 | 34 | 64 | 112 | 232 | 324 |
| | 63 | 77 | 79 | 43 | 35 | 23 | 16 | 30 | 57 | 77 | 125 | 280 | 384 |
| | 68 | 72 | 81 | 56 | 33 | 29 | 25 | 26 | 70 | 91 | 102 | 125 | 144 |
| | 64 | 73 | 74 | 45 | 41 | 21 | 15 | 17 | 22 | 83 | 151 | 182 | 265 |
| | 89 | 94 | 99 | 57 | 47 | 15 | 23 | 46 | 69 | 156 | 264 | 382 | 430 |
| | 67 | 72 | 73 | 42 | 29 | 20 | 19 | 34 | 48 | 71 | 88 | 162 | 248 |
| | 65 | 71 | 75 | 30 | 26 | 15 | 13 | 28 | 33 | 66 | 84 | 236 | 254 |
| | 66 | 74 | 76 | 27 | 14 | 10 | 9 | 13 | 34 | 48 | 47 | 132 | 207 |
| | 69 | 75 | 84 | 54 | 50 | 39 | 34 | 51 | 93 | 117 | 191 | 229 | 489 |
| | 67 | 70 | 73 | 19 | 17 | 13 | 20 | 32 | 75 | 106 | 146 | 342 | 371 |
| NKG2D CAR2 only | 74 | 79 | 92 | 69 | 65 | 53 | 66 | 81 | 126 | 350 | 355 | 541 | 953 |
| | 70 | 77 | 79 | 44 | 25 | 20 | 25 | 57 | 129 | 157 | 245 | 276 | 444 |
| | 75 | 82 | 86 | 40 | 19 | 16 | 24 | 31 | 67 | 95 | 147 | 205 | 224 |
| | 63 | 72 | 76 | 19 | 13 | 11 | 14 | 25 | 39 | 90 | 98 | 104 | 275 |
| | 78 | 83 | 90 | 57 | 27 | 23 | 30 | 68 | 182 | 239 | 237 | 332 | 616 |
| | 63 | 75 | 79 | 44 | 40 | 15 | 40 | 77 | 135 | 215 | 269 | 351 | 362 |
| | 64 | 73 | 77 | 33 | 29 | 15 | 28 | 57 | 80 | 111 | 118 | 240 | 307 |
| | 69 | 78 | 82 | 48 | 24 | 17 | 21 | 28 | 63 | 118 | 137 | 216 | 420 |
| | 63 | 67 | 70 | 27 | 18 | 11 | 12 | 39 | 53 | 154 | 162 | 296 | 381 |
| | 64 | 70 | 75 | 33 | 26 | 11 | 36 | 39 | | | | | |
| HPV-TCR + NKG2D CAR2 | 67 | 70 | 72 | 35 | 19 | 17 | 17 | 42 | 90 | 155 | 215 | 276 | 350 |
| | 66 | 74 | 77 | 29 | 20 | 15 | 19 | 32 | 68 | 107 | 227 | 240 | 390 |
| | 66 | 75 | 79 | 32 | 27 | 24 | 20 | 23 | 53 | 58 | 79 | 198 | 304 |
| | 77 | 81 | 86 | 26 | 25 | 13 | 9 | 28 | 41 | 116 | 186 | 297 | 358 |
| | 72 | 78 | 81 | 33 | 23 | 16 | 17 | 43 | 102 | 161 | 213 | 260 | 483 |
| | 81 | 89 | 94 | 28 | 23 | 14 | 17 | 22 | 28 | 55 | 110 | 291 | 345 |
| | 67 | 71 | 75 | 34 | 17 | 13 | 21 | 36 | 87 | 158 | 286 | 365 | 448 |
| | 64 | 70 | 72 | 26 | 22 | 12 | 14 | 19 | 33 | 57 | 79 | 166 | 198 |
| | 66 | 70 | 74 | 38 | 21 | 11 | 25 | 32 | 75 | 94 | 187 | 287 | 392 |
| | 65 | 67 | 69 | 25 | 20 | 8 | 15 | 27 | 55 | 68 | 80 | 168 | 320 |

| | Days post tumor inoculation | | | | | | | | | | |
|---|---|---|---|---|---|---|---|---|---|---|---|
| | 36 | 39 | 41 | 43 | 46 | 48 | 50 | 53 | 55 | 57 | 60 | 62 |
| Vehicle | 717 | 796 | 884 | 923 | | | | | | | | |
| | 926 | 1217 | 1306 | | | | | | | | | |
| | 742 | 831 | 1034 | 1149 | | | | | | | | |
| | 610 | 780 | 985 | | | | | | | | | |
| | 739 | 757 | 923 | | | | | | | | | |
| | 582 | 693 | 981 | 1039 | 1090 | | | | | | | |
| | 685 | 857 | 982 | | | | | | | | | |
| | 833 | 881 | 1152 | | | | | | | | | |
| NTD | 704 | | | | | | | | | | | |
| | 913 | 798 | 535 | | | | | | | | | |
| | 863 | 425 | 394 | 438 | 384 | | | | | | | |

TABLE 15-continued

Tumor volume of WT CaSki cells over time

|  | | | | | | | | | | | | |
|---|---|---|---|---|---|---|---|---|---|---|---|---|
|  | 802 | 711 | 569 | 347 | 279 | 211 | 166 | 165 | | | | |
|  | 238 | 153 | 123 | 111 | 101 | 84 | 60 | | | | | |
|  | 715 | | | | | | | | | | | |
|  | 624 | 464 | 296 | | | | | | | | | |
|  | 261 | | | | | | | | | | | |
| HPV-TCR only | 390 | 426 | 632 | 328 | 211 | 163 | 127 | 176 | 176 | 177 | 160 | 97 |
|  | 435 | 440 | 549 | 826 | 827 | 883 | | | | | | |
|  | 221 | 210 | 376 | 472 | 513 | 533 | 600 | 372 | 158 | 165 | 164 | |
|  | 590 | 547 | 633 | 601 | 391 | 380 | 384 | 407 | 409 | 268 | 289 | 213 |
|  | 579 | 621 | 779 | 962 | | | | | | | | |
|  | 375 | 412 | 497 | 635 | 649 | 744 | 651 | 504 | 479 | 489 | 424 | 185 |
|  | 340 | 355 | 451 | 628 | 607 | 635 | 802 | 834 | | | | |
|  | 291 | 365 | 474 | 558 | 733 | 647 | 868 | 413 | 280 | 282 | 277 | 181 |
|  | 523 | 517 | 754 | 855 | | | | | | | | |
|  | 402 | 565 | 721 | 938 | 877 | 755 | 691 | 668 | 669 | 799 | | |
| NKG2D CAR2 only | 466 | 760 | 1139 | 1569 | 1992 | | | | | | | |
|  | 471 | 524 | 755 | 983 | 1013 | 1119 | 1083 | 933 | 1098 | 1189 | | |
|  | 278 | 416 | 736 | 868 | 1024 | 1110 | 1262 | 1068 | 1095 | 1160 | 915 | 944 |
|  | 363 | 481 | 581 | 827 | 1038 | 970 | 901 | 846 | 846 | 913 | 994 | |
|  | 935 | 1044 | 1332 | 1724 | 2306 | | | | | | | |
|  | 450 | 808 | 1103 | 1278 | 1316 | 1329 | 1638 | 1698 | | | | |
|  | 430 | 610 | 726 | 785 | 847 | 890 | 1045 | 1087 | 1109 | 1121 | 1194 | |
|  | 496 | 564 | 762 | 870 | 1185 | 1048 | 1077 | 1138 | 1339 | | | |
|  | 461 | 572 | 714 | 756 | 771 | 853 | 934 | 1118 | 1154 | 1235 | | |
| HPV-TCR + NKG2D CAR2 | 419 | 513 | 783 | 847 | 1158 | 1174 | 1209 | 1542 | | | | |
|  | 495 | 632 | 917 | 1114 | 1320 | 1102 | 1262 | 1176 | | | | |
|  | 457 | 484 | 458 | 569 | 631 | 670 | 807 | 1475 | | | | |
|  | 425 | 594 | 816 | 1028 | 1020 | 1068 | 1082 | 1162 | | | | |
|  | 647 | 805 | 676 | 865 | 978 | 994 | 1017 | 887 | 890 | 924 | 1096 | |
|  | 450 | 517 | 552 | 572 | 807 | 916 | 939 | 1008 | 965 | 1016 | 1079 | 607 |
|  | 550 | 814 | 1165 | 1376 | 1494 | 2014 | | | | | | |
|  | 374 | 415 | 605 | 823 | 941 | 1034 | 1312 | 1932 | | | | |
|  | 611 | 773 | 1163 | 1347 | 1585 | | | | | | | |
|  | 496 | 693 | 559 | 678 | 795 | 912 | 1165 | 1411 | 1339 | | | |

TABLE 16

Tumor volume of β2MKO CaSki cells over time

| | Days post tumor inoculation | | | | | | | | | | | | |
|---|---|---|---|---|---|---|---|---|---|---|---|---|---|
| | 6 | 8 | 11 | 13 | 15 | 18 | 20 | 22 | 25 | 27 | 29 | 32 | 34 |
| Vehicle | 34 | 36 | 51 | 58 | 105 | 197 | 281 | 354 | 400 | 487 | 561 | 669 | 689 |
|  | 28 | 29 | 39 | 44 | 98 | 128 | 206 | 234 | 344 | 371 | 382 | 484 | 501 |
|  | 23 | 30 | 41 | 51 | 79 | 182 | 238 | 300 | 323 | 385 | 409 | 417 | 454 |
|  | 22 | 31 | 38 | 44 | 79 | 114 | 198 | 223 | 242 | 297 | 341 | 511 | 613 |
|  | 31 | 36 | 48 | 54 | 89 | 196 | 273 | 369 | 400 | 459 | 532 | 676 | 762 |
|  | 63 | 73 | 79 | 99 | 155 | 215 | 310 | 357 | 364 | 441 | 511 | 504 | 586 |
|  | 44 | 47 | 52 | 58 | 101 | 247 | 254 | 342 | 423 | 522 | 539 | 690 | 748 |
|  | 64 | 66 | 71 | 115 | 131 | 313 | 432 | 551 | 574 | 681 | 676 | 822 | 880 |
| NTD | 35 | 43 | 48 | 55 | 75 | 161 | 169 | 209 | 259 | 312 | 343 | 487 | 494 |
|  | 35 | 38 | 57 | 63 | 92 | 169 | 213 | 323 | 413 | 455 | 492 | 584 | 667 |
|  | 19 | 25 | 33 | 40 | 76 | 78 | 83 | 123 | 130 | 192 | 201 | 330 | 375 |
|  | 31 | 40 | 48 | 54 | 77 | 110 | 134 | 173 | 242 | 322 | 349 | 371 | 381 |
|  | 45 | 48 | 53 | 65 | 85 | 240 | 242 | 250 | 349 | 399 | 419 | 449 | 270 |
|  | 46 | 47 | 55 | 59 | 107 | 217 | 231 | 284 | 373 | 460 | 472 | 401 | 408 |
|  | 20 | 27 | 31 | 33 | 45 | 136 | 158 | 165 | 279 | 319 | 334 | 356 | 377 |
|  | 50 | 58 | 62 | 67 | 114 | 290 | 298 | 404 | 407 | 473 | 539 | 517 | 327 |
| HPV-TCR only | 41 | 49 | 66 | 72 | 143 | 350 | 367 | 414 | 450 | 530 | 609 | 633 | 680 |
|  | 37 | 40 | 49 | 63 | 120 | 266 | 374 | 470 | 520 | 554 | 586 | 707 | 816 |
|  | 14 | 21 | 32 | 44 | 71 | 224 | 230 | 308 | 335 | 413 | 506 | 738 | 758 |
|  | 25 | 30 | 37 | 51 | 102 | 211 | 243 | 293 | 336 | 372 | 454 | 563 | 629 |
|  | 59 | 63 | 69 | 81 | 137 | 239 | 299 | 483 | 542 | 556 | 581 | 657 | 638 |
|  | 21 | 29 | 30 | 45 | 90 | 225 | 298 | 401 | 537 | 624 | 688 | 855 | 904 |
|  | 24 | 28 | 38 | 60 | 113 | 207 | 281 | 390 | 515 | 570 | 612 | 771 | 863 |
|  | 27 | 31 | 53 | 72 | 82 | 210 | 274 | 315 | 351 | 413 | 521 | 579 | 661 |
|  | 17 | 22 | 35 | 53 | 67 | 216 | 248 | 337 | 347 | 431 | 425 | 501 | 688 |
|  | 32 | 40 | 44 | 112 | 208 | 216 | 366 | 498 | 727 | 772 | 795 | 945 | 965 |
| NKG2D CAR2 only | 58 | 64 | 68 | 30 | 0 | 0 | 0 | 0 | 0 | 0 | 0 | 0 | 0 |
|  | 36 | 47 | 50 | 25 | 0 | 0 | 0 | 0 | 0 | 0 | 0 | 0 | 0 |
|  | 26 | 36 | 38 | 22 | 0 | 0 | 0 | 0 | 0 | 0 | 0 | 0 | 0 |
|  | 49 | 54 | 57 | 27 | 0 | 0 | 0 | 0 | 0 | 0 | 0 | 0 | 0 |
|  | 44 | 49 | 51 | 29 | 0 | 0 | 0 | 0 | 0 | 0 | 0 | 0 | 0 |
|  | 35 | 40 | 43 | 26 | 12 | 0 | 0 | 0 | 0 | 0 | 0 | 0 | 0 |

TABLE 16-continued

Tumor volume of β2MKO CaSki cells over time

|  | | | | | | | | | | | | |
|---|---|---|---|---|---|---|---|---|---|---|---|---|
|  | 21 | 30 | 34 | 24 | 0 | 0 | 0 | 0 | 0 | 0 | 0 | 0 |
|  | 40 | 42 | 45 | 26 | 0 | 0 | 0 | 0 | 0 | 18 | 25 | 29 | 56 |
|  | 29 | 33 | 43 | 26 | 0 | 0 | 0 | 0 | 0 | 0 | 0 | 0 |
|  | 38 | 43 | 46 | 30 | 19 | 0 | 0 | 0 |
| HPV-TCR + | 32 | 41 | 42 | 29 | 0 | 0 | 0 | 0 | 0 | 0 | 0 | 0 |
| NKG2D | 33 | 40 | 43 | 27 | 0 | 0 | 0 | 0 | 0 | 17 | 15 | 49 | 56 |
| CAR2 | 15 | 23 | 30 | 18 | 0 | 0 | 0 | 0 | 0 | 0 | 0 | 0 |
|  | 68 | 74 | 77 | 32 | 15 | 4 | 4 | 4 | 11 | 23 | 22 | 58 | 114 |
|  | 28 | 37 | 39 | 17 | 0 | 0 | 0 | 0 | 0 | 0 | 25 | 84 |
|  | 25 | 31 | 32 | 23 | 0 | 0 | 0 | 0 | 0 | 0 | 0 | 0 |
|  | 35 | 39 | 46 | 25 | 7 | 0 | 0 | 0 | 0 | 0 | 18 | 31 | 96 |
|  | 32 | 35 | 38 | 24 | 0 | 0 | 0 | 0 | 0 | 0 | 12 | 39 | 62 |
|  | 22 | 26 | 40 | 23 | 0 | 0 | 0 | 0 | 0 | 18 | 18 | 72 | 86 |
|  | 37 | 42 | 46 | 27 | 0 | 0 | 0 | 0 | 0 | 0 | 0 | 0 |

| | Days post tumor inoculation | | | | | | | | | | | |
|---|---|---|---|---|---|---|---|---|---|---|---|---|
|  | 36 | 39 | 41 | 43 | 46 | 48 | 50 | 53 | 55 | 57 | 60 | 62 |
| Vehicle | 774 | 836 | 1083 | 1187 | | | | | | | | |
|  | 624 | 767 | 1007 | | | | | | | | | |
|  | 607 | 668 | 805 | 1035 | | | | | | | | |
|  | 759 | 937 | 1037 | | | | | | | | | |
|  | 933 | 1020 | 1300 | | | | | | | | | |
|  | 624 | 703 | 806 | 953 | 1080 | | | | | | | |
|  | 776 | 902 | 1019 | | | | | | | | | |
|  | 942 | 968 | 1141 | | | | | | | | | |
| NTD | 488 | | | | | | | | | | | |
|  | 685 | 618 | 522 | | | | | | | | | |
|  | 436 | 404 | 256 | 236 | 151 | | | | | | | |
|  | 383 | 295 | 272 | 282 | 155 | 154 | 166 | 100 | | | | |
|  | 259 | 125 | 85 | 77 | 74 | 59 | 60 | | | | | |
|  | 297 | | | | | | | | | | | |
|  | 397 | 346 | 423 | | | | | | | | | |
|  | 145 | | | | | | | | | | | |
| HPV-TCR | 832 | 837 | 980 | 879 | 533 | 409 | 416 | 392 | 249 | 297 | 186 | 117 |
| only | 813 | 862 | 915 | 1017 | 1152 | 1222 | | | | | | |
|  | 805 | 643 | 865 | 1020 | 949 | 981 | 768 | 668 | 427 | 357 | 282 | |
|  | 763 | 758 | 762 | 829 | 793 | 671 | 680 | 552 | 558 | 578 | 201 | 154 |
|  | 734 | 869 | 1029 | 1204 | | | | | | | | |
|  | 756 | 781 | 839 | 944 | 1000 | 944 | 952 | 962 | 589 | 534 | 444 | 296 |
|  | 939 | 883 | 1035 | 1209 | 1121 | 1164 | 1183 | 1312 | | | | |
|  | 758 | 868 | 878 | 882 | 903 | 218 | 519 | 721 | 792 | 565 | 697 | 590 |
|  | 866 | 869 | 994 | 1163 | | | | | | | | |
|  | 699 | 565 | 774 | 1036 | 1039 | 1083 | 1094 | 1246 | 1319 | 1376 | | |
| NKG2D CAR2 | 0 | 89 | 167 | 179 | 304 | | | | | | | |
| only | 0 | 90 | 174 | 195 | 236 | 280 | 457 | 632 | 856 | 1045 | | |
|  | 0 | 55 | 126 | 139 | 147 | 160 | 213 | 299 | 388 | 442 | 598 | 648 |
|  | 0 | 55 | 73 | 91 | 179 | 212 | 334 | 523 | 711 | 885 | 1178 | |
|  | 0 | 54 | 88 | 122 | 189 | | | | | | | |
|  | 90 | 94 | 115 | 160 | 180 | 211 | 354 | 418 | | | | |
|  | 0 | 33 | 98 | 151 | 171 | 224 | 308 | 525 | 657 | 860 | 1167 | |
|  | 138 | 172 | 234 | 279 | 387 | 398 | 538 | 753 | 1025 | | | |
|  | 0 | 84 | 159 | 231 | 275 | 321 | 530 | 717 | 827 | 1094 | | |
| HPV-TCR + | 123 | 134 | 177 | 181 | 248 | 264 | 356 | 488 | | | | |
| NKG2D | 172 | 172 | 224 | 233 | 317 | 428 | 604 | 892 | | | | |
| CAR2 | 54 | 112 | 162 | 188 | 227 | 283 | 450 | 598 | | | | |
|  | 140 | 217 | 351 | 403 | 479 | 526 | 630 | 961 | | | | |
|  | 189 | 195 | 272 | 365 | 407 | 480 | 609 | 687 | 758 | 895 | 1015 | |
|  | 0 | 60 | 74 | 148 | 157 | 172 | 222 | 459 | 669 | 750 | 753 | 750 |
|  | 129 | 153 | 206 | 238 | 258 | 311 | | | | | | |
|  | 168 | 171 | 172 | 195 | 264 | 364 | 541 | 792 | | | | |
|  | 189 | 234 | 250 | 295 | 430 | | | | | | | |
|  | 0 | 100 | 150 | 194 | 221 | 294 | 442 | 508 | 712 | | | |

TABLE 17

Weight of tumor-bearing mice over time

| | Days post tumor inoculation | | | | | | | | | | | | |
|---|---|---|---|---|---|---|---|---|---|---|---|---|---|
|  | 6 | 8 | 11 | 13 | 15 | 18 | 20 | 22 | 25 | 27 | 29 | 32 | 34 |
| Vehicle | 0.0 | −3.9 | −1.7 | −5.6 | −3.9 | −0.9 | −3.9 | −0.4 | 0.4 | 1.3 | 4.3 | 4.8 | 3.9 |
|  | 0.0 | 3.1 | 3.6 | 3.1 | 7.1 | 12.5 | 12.1 | 9.4 | 10.3 | 9.4 | 11.6 | 12.5 | 10.7 |

TABLE 17-continued

Weight of tumor-bearing mice over time

|  | | | | | | | | | | | | |
|---|---|---|---|---|---|---|---|---|---|---|---|---|
|  | 0.0 | −0.9 | 0.0 | −1.8 | 0.9 | 2.7 | 0.4 | 4.0 | 4.9 | 4.5 | 6.7 | 4.9 | 3.1 |
|  | 0.0 | 0.8 | −1.5 | −3.1 | 0.8 | 5.0 | 0.4 | −0.4 | −0.8 | 0.8 | 1.2 | 2.7 | −0.4 |
|  | 0.0 | −0.8 | 3.3 | 1.6 | 4.1 | 9.8 | 9.4 | 11.9 | 9.8 | 8.2 | 10.7 | 11.1 | 9.0 |
|  | 0.0 | −6.8 | −6.0 | −12.0 | −8.8 | −5.2 | −6.8 | −5.6 | ## | −12.9 | ## | −5.6 | −8.8 |
|  | 0.0 | −2.7 | −0.4 | −4.0 | −1.8 | 5.4 | 0.4 | 2.7 | 5.4 | 4.9 | 5.4 | 7.1 | 1.8 |
|  | 0.0 | −0.4 | 2.3 | 2.7 | 2.3 | 6.8 | 5.7 | 7.2 | 7.6 | 8.4 | 8.7 | 8.7 | 7.6 |
| NTD | 0.0 | −0.8 | 2.3 | −1.1 | 4.2 | 6.8 | 3.8 | 6.8 | 8.3 | 3.8 | 6.0 | 3.4 | −8.3 |
|  | 0.0 | −0.8 | −2.1 | −3.7 | 0.8 | −0.8 | −4.5 | −2.5 | −1.2 | −4.1 | −2.5 | 3.3 | −1.2 |
|  | 0.0 | 1.4 | 5.2 | 0.9 | 4.2 | 10.3 | 6.6 | 8.0 | 8.9 | 8.5 | 8.9 | 10.8 | −2.3 |
|  | 0.0 | −3.8 | 1.7 | −1.7 | 0.0 | 3.8 | 1.3 | −2.5 | −0.8 | −3.8 | −1.7 | 3.8 | −1.7 |
|  | 0.0 | −0.4 | 0.4 | −6.1 | −2.7 | 1.1 | 0.4 | 0.4 | −3.8 | −6.8 | −6.4 | −5.3 | −8.7 |
|  | 0.0 | −5.0 | −2.1 | −6.2 | −3.7 | 1.2 | −3.3 | 0.4 | 0.4 | 0.8 | −1.2 | −10.8 | −16.2 |
|  | 0.0 | −3.2 | −2.4 | −3.2 | −1.2 | 3.6 | 2.8 | 4.7 | 3.2 | 2.4 | 2.0 | −2.0 | −8.3 |
|  | 0.0 | −2.8 | −4.0 | −4.8 | −2.0 | −1.2 | −3.2 | −3.2 | −2.0 | −3.6 | −2.4 | −7.2 | −13.7 |
| HPV-TCR | 0.0 | 4.0 | 4.9 | 1.3 | 3.1 | 6.7 | −2.7 | −1.8 | 1.3 | 3.1 | 4.5 | 5.4 | 3.1 |
| only | 0.0 | −1.6 | 0.4 | −3.1 | −0.8 | 2.0 | −2.7 | −1.2 | −0.8 | −3.9 | −2.7 | −1.2 | −3.5 |
|  | 0.0 | −2.5 | −2.1 | −5.4 | −5.0 | 3.3 | −2.5 | 0.0 | 0.8 | −0.8 | 2.5 | 5.0 | 0.4 |
|  | 0.0 | 0.4 | 3.5 | 0.9 | 6.5 | 10.4 | 5.6 | 6.1 | 5.6 | 3.5 | 8.2 | 11.3 | 7.4 |
|  | 0.0 | −3.2 | 0.7 | −2.8 | −1.4 | 1.1 | −2.1 | 0.7 | −0.7 | −1.1 | 1.8 | 2.1 | −1.1 |
|  | 0.0 | 3.0 | 5.1 | 1.7 | 4.7 | 10.3 | 6.0 | 10.3 | 10.3 | 8.1 | 9.8 | 7.7 | 3.8 |
|  | 0.0 | 0.0 | 2.1 | −0.4 | 4.2 | 5.4 | 2.9 | 5.4 | 6.3 | 1.7 | 5.0 | 9.6 | 5.9 |
|  | 0.0 | 2.0 | 2.0 | 0.0 | 0.0 | 2.4 | 0.4 | 0.8 | 3.2 | 3.6 | 1.6 | 5.2 | 2.4 |
|  | 0.0 | 3.4 | 3.1 | 5.3 | 3.1 | 5.0 | 0.4 | 2.7 | 4.6 | 2.3 | 4.2 | 6.5 | 0.4 |
|  | 0.0 | −3.4 | −4.5 | −7.2 | −4.5 | −2.6 | −2.3 | −3.4 | −2.3 | −6.4 | −4.2 | 0.4 | −3.4 |
| NKG2D CAR2 | 0.0 | −3.2 | −1.6 | −6.0 | −0.4 | 0.4 | −3.2 | −5.2 | −3.2 | −1.2 | 3.2 | 6.4 | 2.0 |
| only | 0.0 | 2.7 | 6.4 | 4.5 | 9.5 | 9.1 | 9.5 | 12.7 | 14.1 | 17.3 | 15.5 | 16.8 | 13.2 |
|  | 0.0 | 0.5 | 3.3 | −2.8 | 3.3 | 5.2 | 0.5 | 3.3 | −0.9 | −0.9 | 1.9 | 3.3 | −0.5 |
|  | 0.0 | −4.5 | −4.5 | −7.0 | −2.9 | −2.9 | −6.1 | −1.2 | −2.5 | −5.3 | −4.5 | −3.3 | −3.7 |
|  | 0.0 | −0.4 | 2.2 | 1.8 | 4.0 | 4.0 | −0.4 | 0.9 | 0.4 | −1.3 | 2.7 | 5.4 | 3.1 |
|  | 0.0 | 1.6 | 3.6 | 2.0 | 1.6 | 5.6 | 1.6 | 4.0 | 2.8 | 2.4 | 1.6 | 6.0 | 2.4 |
|  | 0.0 | −3.7 | 1.2 | 0.0 | 6.6 | 6.2 | 1.2 | 1.7 | 3.3 | −0.4 | 2.1 | 3.7 | 0.4 |
|  | 0.0 | −3.7 | −4.1 | −4.8 | 1.5 | −3.0 | −5.9 | −5.9 | −9.3 | −9.6 | −8.1 | −8.9 | −8.9 |
|  | 0.0 | 2.9 | 4.1 | 5.4 | 10.4 | 10.0 | 5.8 | 6.2 | 6.2 | 2.5 | 6.6 | 5.0 | 3.3 |
|  | 0.0 | −0.8 | 0.4 | −1.6 | 1.6 | 3.3 | 0.8 | −0.4 | | | | | |
| HPV-TCR + | 0.0 | 0.8 | 2.5 | 1.6 | 2.9 | 7.0 | 4.9 | 6.6 | 5.3 | 5.7 | 5.7 | 7.0 | 3.7 |
| NKG2D | 0.0 | 0.4 | 0.9 | −3.4 | 0.4 | 0.9 | −2.2 | −2.6 | 1.7 | −1.7 | −0.9 | −0.4 | −4.7 |
| CAR2 | 0.0 | −9.0 | −9.0 | −12.1 | −10.2 | −7.4 | −11.3 | −10.2 | −9.8 | −11.7 | −11.3 | −9.0 | −9.8 |
|  | 0.0 | −4.0 | −0.9 | −7.1 | −1.8 | 4.0 | 1.3 | 4.5 | 2.2 | 1.8 | 3.6 | 4.9 | 3.6 |
|  | 0.0 | 0.8 | 3.8 | 0.0 | 4.6 | 8.0 | 5.9 | 8.4 | 7.2 | 7.2 | 6.8 | 4.6 | 4.6 |
|  | 0.0 | −2.8 | 2.8 | −0.9 | 1.4 | 2.3 | −0.5 | 0.5 | −1.4 | −0.5 | 2.3 | −1.9 | −3.8 |
|  | 0.0 | 2.7 | −2.2 | 0.0 | −0.4 | 0.0 | 1.8 | 2.7 | 2.2 | 0.4 | 4.9 | −0.9 | −1.3 |
|  | 0.0 | 0.4 | 1.9 | 0.4 | 1.5 | 3.8 | −3.4 | −6.1 | −8.0 | −11.1 | −8.0 | −6.9 | −8.0 |
|  | 0.0 | −1.9 | 1.9 | 1.1 | 1.1 | 5.3 | 1.1 | 0.0 | −1.9 | −1.1 | 3.4 | 1.1 | −2.7 |
|  | 0.0 | −1.6 | −2.4 | −3.6 | −1.6 | 2.0 | −3.6 | −4.0 | −4.4 | −7.5 | −4.0 | −5.6 | −6.7 |

| | Days post tumor inoculation | | | | | | | | | | | |
|---|---|---|---|---|---|---|---|---|---|---|---|---|
| | 36 | 39 | 41 | 43 | 46 | 48 | 50 | 53 | 55 | 57 | 60 | 62 |
| Vehicle | 3.5 | 3.5 | 3.5 | 5.6 | | | | | | | | |
|  | 7.6 | 14.3 | 12.5 | | | | | | | | | |
|  | 7.6 | 8.9 | 8.9 | 10.7 | | | | | | | | |
|  | 0.8 | 8.5 | 4.2 | | | | | | | | | |
|  | 7.0 | 11.1 | 12.7 | | | | | | | | | |
|  | −6.0 | −2.4 | −3.6 | −0.8 | 1.6 | | | | | | | |
|  | 0.4 | −0.4 | 0.4 | | | | | | | | | |
|  | 3.0 | 3.4 | 2.3 | | | | | | | | | |
| NTD | −15.8 | | | | | | | | | | | |
|  | −4.5 | −14.0 | −23.6 | | | | | | | | | |
|  | 0.9 | 0.0 | −3.3 | −2.8 | −18.3 | | | | | | | |
|  | −2.1 | −2.5 | −5.9 | −9.7 | −15.7 | −16.1 | −18.6 | −21.2 | | | | |
|  | −14.4 | −11.7 | −13.6 | −14.4 | −17.4 | −17.0 | −21.6 | | | | | |
|  | ### | | | | | | | | | | | |
|  | −13.4 | −15.0 | −21.7 | | | | | | | | | |
|  | −20.1 | | | | | | | | | | | |
| HPV-TCR | 5.4 | 13.0 | 8.1 | 5.8 | 4.0 | 6.7 | 5.8 | 1.3 | 2.2 | 1.8 | 0.4 | −4.5 |
| only | −3.5 | 1.6 | 1.6 | 2.3 | −2.3 | −2.0 | | | | | | |
|  | −1.3 | 1.7 | 3.3 | 1.3 | −0.4 | −0.8 | −0.8 | −7.5 | −10.5 | −15.1 | −21.3 | |
|  | 7.4 | 12.1 | 12.1 | 10.8 | 10.0 | 5.6 | 3.9 | −1.3 | −3.5 | −7.4 | −8.7 | −12.1 |
|  | −2.1 | 1.4 | 1.4 | 3.9 | | | | | | | | |
|  | 2.1 | 3.4 | 0.4 | 0.0 | 3.0 | 2.1 | −5.1 | −2.6 | −1.7 | −6.0 | −3.8 | −2.6 |
|  | 5.0 | 9.2 | 9.6 | 5.9 | 9.6 | 7.9 | 9.2 | 9.2 | | | | |
|  | −0.8 | 4.8 | 2.0 | 5.6 | 0.8 | 3.2 | 6.4 | −1.6 | 4.0 | 2.4 | 3.2 | 2.0 |
|  | 0.0 | 3.1 | −2.3 | −3.1 | | | | | | | | |
|  | −4.9 | 0.8 | −1.5 | 1.1 | 1.9 | −2.6 | 0.8 | −1.5 | 0.8 | 2.3 | | |
| NKG2D CAR2 | −2.4 | 2.8 | 3.2 | 5.6 | 8.8 | | | | | | | |
| only | 12.3 | 14.1 | 20.5 | 20.9 | 17.7 | 19.1 | 20.0 | 18.2 | 22.7 | 24.1 | | |
|  | 2.3 | 8.0 | 6.1 | 7.5 | 10.3 | 12.7 | 12.7 | 9.4 | 12.7 | 15.0 | 18.3 | 16.4 |

TABLE 17-continued

Weight of tumor-bearing mice over time

| | | | | | | | | | | | | |
|---|---|---|---|---|---|---|---|---|---|---|---|---|
| | −1.2 | 0.8 | −1.6 | −1.2 | 1.2 | −0.8 | 1.6 | −0.4 | 0.0 | 2.9 | 5.7 | |
| | −0.1 | 6.3 | 4.0 | 9.9 | 12.6 | | | | | | | |
| | −0.4 | 5.2 | 2.4 | 6.8 | 4.0 | 6.0 | 8.0 | 7.6 | | | | |
| | 0.0 | 2.1 | 2.5 | 3.3 | 4.1 | 5.0 | 5.8 | 7.0 | 7.9 | 11.2 | 14.9 | |
| | −8.9 | −4.8 | −5.2 | −3.7 | −3.0 | −4.4 | −2.6 | −2.2 | 2.2 | | | |
| | 2.9 | 8.7 | 8.3 | 9.5 | 4.6 | 3.7 | 10.0 | 11.2 | 12.4 | 14.1 | | |
| HPV-TCR + | 4.9 | 6.6 | 8.6 | 11.1 | 13.1 | 13.9 | 13.1 | 12.3 | | | | |
| NKG2D | −4.3 | 3.4 | 3.9 | 9.9 | 8.2 | 5.2 | 5.6 | 4.7 | | | | |
| CAR2 | −8.6 | −6.3 | −9.0 | −7.8 | −5.9 | −1.2 | −0.4 | 1.6 | | | | |
| | 5.4 | 5.8 | 6.7 | 9.4 | 8.0 | 11.2 | 10.7 | 10.7 | | | | |
| | 2.1 | 4.2 | 2.5 | 6.3 | 4.6 | 8.0 | 8.9 | 6.3 | 8.4 | 8.4 | 11.0 | |
| | −2.3 | 0.0 | −0.5 | −1.4 | 1.9 | 3.3 | 5.2 | 1.9 | 7.0 | 4.7 | 8.9 | 4.2 |
| | 0.0 | 4.9 | 3.1 | 4.9 | 8.5 | 9.4 | | | | | | |
| | −7.6 | −5.7 | −6.9 | −3.4 | −2.7 | 1.5 | 3.1 | 3.1 | | | | |
| | −4.2 | −1.1 | 0.4 | 1.1 | 3.8 | | | | | | | |
| | −6.0 | −1.6 | −4.8 | −1.6 | −0.4 | 1.2 | 4.4 | 5.6 | 4.8 | | | |

TABLE 18

Percentage of adoptively transferred T cells in peripheral blood
Percent hCD45 in peripheral lymphocytes

| | Days post tumor inoculation | | | | | |
|---|---|---|---|---|---|---|
| | 1 | 7 | 14 | 21 | 28 | 35 |
| Vehicle | 0.00 | 0.01 | 0.03 | 0.02 | 0.02 | 0.01 |
| | 0.00 | 0.04 | 0.04 | 0.02 | 0.02 | 0.02 |
| | 0.06 | 0.00 | 0.02 | 0.02 | 0.01 | 0.01 |
| | 0.01 | 0.00 | 0.02 | 0.02 | 0.01 | 0.01 |
| | 0.10 | 0.00 | 0.03 | 0.02 | 0.00 | 0.01 |
| | 0.02 | 0.01 | 0.03 | 0.02 | 0.00 | 0.00 |
| | 0.01 | 0.09 | 0.03 | 0.02 | 0.01 | 0.00 |
| | 0.19 | 0.00 | 0.02 | 0.01 | 0.00 | 5.03 |
| NTD | 8.03 | 8.63 | 2.56 | 9.25 | 41.80 | 78.20 |
| | 7.47 | 0.36 | 2.24 | 4.62 | 19.80 | 43.20 |
| | 9.44 | 8.83 | 1.95 | 4.58 | 16.70 | 29.90 |
| | 5.45 | 6.13 | 2.09 | 4.55 | 11.50 | 28.10 |
| | 6.90 | 6.54 | 0.73 | 8.59 | 25.30 | 27.20 |
| | 4.61 | 5.04 | 1.48 | 5.09 | 53.60 | 38.00 |
| | 7.35 | 6.04 | 1.26 | 6.15 | 29.80 | 26.60 |
| | 4.77 | 3.45 | 1.94 | 14.80 | 40.00 | 0.00 |
| HPV-TCR only | 4.14 | 1.77 | 0.16 | 0.09 | 1.33 | 0.45 |
| | 3.26 | 1.24 | 0.17 | 0.15 | 0.16 | 0.43 |
| | 4.21 | 2.11 | 0.33 | 0.51 | 0.00 | 18.60 |
| | 3.32 | 4.59 | 0.43 | 0.62 | 0.00 | 2.02 |
| | 3.62 | 2.92 | 0.16 | 0.29 | 0.00 | 1.53 |
| | 3.26 | 1.97 | 0.15 | 0.11 | 0.69 | 1.99 |
| | 3.24 | 2.41 | 0.16 | 0.58 | 1.80 | 0.58 |
| | 4.23 | 2.46 | 0.17 | 0.62 | 0.49 | 5.95 |
| | 4.36 | 4.46 | 0.20 | 2.52 | 0.38 | 0.47 |
| | 3.18 | 2.72 | 0.12 | 0.22 | 0.24 | 0.02 |
| NKG2D CAR2 only | 0.43 | 1.35 | 0.04 | 0.07 | 0.01 | 0.50 |
| | 0.60 | 1.92 | 0.09 | 1.28 | 1.39 | 0.01 |
| | 0.67 | 3.19 | 0.07 | 0.06 | 0.02 | 4.89 |
| | 0.65 | 3.15 | 0.09 | 0.16 | 0.65 | 0.01 |
| | 1.06 | 1.43 | 0.13 | 0.06 | 0.04 | 0.10 |
| | 0.75 | 2.70 | 0.05 | 0.12 | 0.03 | 0.02 |
| | 0.73 | 3.39 | 0.10 | 0.09 | 0.02 | 0.01 |
| | 0.86 | 2.98 | 0.10 | 0.07 | 0.02 | 0.02 |
| | 0.00 | 1.21 | 0.05 | 0.05 | 0.02 | 0.02 |
| | 0.65 | 1.75 | 0.09 | 0.07 | 0.03 | 0.00 |
| HPV-TCR + NKG2D CAR2 | 0.42 | 1.91 | 0.06 | 0.02 | 0.03 | 0.01 |
| | 0.32 | 1.99 | 0.06 | 0.03 | 0.00 | 0.03 |
| | 0.40 | 1.84 | 0.10 | 0.06 | 0.02 | 0.81 |
| | 0.37 | 1.81 | 0.13 | 0.37 | 0.40 | 0.02 |
| | 0.32 | 2.10 | 0.06 | 0.02 | 0.01 | 0.10 |
| | 0.25 | 1.62 | 0.05 | 0.01 | 0.01 | 0.01 |
| | 0.24 | 1.32 | 0.09 | 0.05 | 0.01 | 0.22 |
| | 0.26 | 2.71 | 0.10 | 0.02 | 0.01 | 0.33 |
| | 0.30 | 2.76 | 0.05 | 0.26 | 0.08 | 0.02 |
| | 0.30 | 3.12 | 0.07 | 0.05 | 0.02 | 10.90 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A chimeric antigen receptor (CAR), comprising:
   a NKG2D ecto domain;
   a transmembrane domain;
   a 4-1BB costimulatory domain; and
   a signaling domain consisting only of:
   a CD3-epsilon signaling domain, wherein the CD3-epsilon signaling domain consisting only of an amino acid sequence having at least 95% sequence identity to SEQ ID NO: 31.

2. The CAR of claim 1, further comprising:
   a CD8-alpha hinge domain.

3. The CAR of claim 2, wherein the CD8-alpha hinge domain comprises an amino acid sequence according to SEQ ID NO: 15.

4. The CAR of claim 1, wherein the NKG2D ecto domain comprises an amino acid sequence according to SEQ ID NO: 3.

5. The CAR of claim 1, wherein the transmembrane domain further comprises a CD28 transmembrane domain.

6. The CAR of claim 5, wherein the CD28 transmembrane domain comprises an amino acid sequence according to SEQ ID NO: 21.

7. The CAR of claim 1, wherein the 4-1BB costimulatory domain comprises an amino acid sequence according to SEQ ID NO: 33 or SEQ ID NO: 63.

* * * * *

SEQUENCE LISTING

<160> NUMBER OF SEQ ID NOS: 78

<210> SEQ ID NO 1

<400> SEQUENCE: 1

000

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic

```
                peptide
<220> FEATURE:
<221> NAME/KEY: MOD_RES
<222> LOCATION: (2)..(2)
<223> OTHER INFORMATION: V or I
<220> FEATURE:
<221> NAME/KEY: MOD_RES
<222> LOCATION: (4)..(4)
<223> OTHER INFORMATION: Any amino acid

<400> SEQUENCE: 2

Asp Xaa Glu Xaa Asn Pro Gly Pro
1               5

<210> SEQ ID NO 3
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val
    130                 135

<210> SEQ ID NO 4
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ttattcaacc aagaagtcca gattcccttg accgaaagtt actgcggccc atgtccgaaa      60
aactggatat gttataaaaa taactgttac cagttcttcg atgaatctaa aaactggtat     120
gagagccagg catcttgtat gtctcaaaat gccagcctgc tcaaagtata cagcaaggag     180
gaccaggatt tacttaaact ggtgaagtca tatcactgga tgggattggt acacattccc     240
acaaatggat cttggcagtg gaagacggc tccattctct cacccaacct actaacaata     300
attgaaatgc agaagggaga ctgcgcactc tatgcatcga gctttaaagg ttatatagaa     360
aactgttcaa ctccaaatac atacatctgc atgcaaagga ctgta                    405
```

```
<210> SEQ ID NO 5
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ttattcaacc aagaagtcca aattcccttg accgaaagtt actgtggccc atgtcctaaa    60
aactggatat gttacaaaaa taactgttac caattcttcg atgaaagtaa aaactggtat   120
gagagccagg cttcttgtat gtctcaaaat gccagccttc tgaaagtata cagcaaggag   180
gaccaggatt tacttaaact ggtgaagtca tatcattgga tgggactagt acacattcca   240
acaaatggat cttggcagtg ggaagacggc tccattctct cacccaacct actaacaata   300
attgaaatgc agaagggaga ctgtgcactc tatgcatcga gctttaaagg ctatatagaa   360
aactgttcaa ctccaaatac atacatctgc atgcaaagga ctgtg                  405

<210> SEQ ID NO 6
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser
1

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 ggatcc                                                               6

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 gggtcc                                                               6

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Ser Gly Gly Gly Ser
1               5
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcggtggaa gcggaggagg ttcc                                           24

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Thr Ser Gly Ser Gly Lys Pro Gly Ser Gly Glu Gly Ser Thr
1               5                   10                  15

Lys Gly

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggagcacta gcggctctgg caaacctgga tctggcgagg gatctaccaa gggc          54

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggagcacaa gcggctctgg caaacctgga tctggcgagg gatctaccaa gggc          54

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggagcacaa gcggctctgg caaacctgga tccggcgagg gatctaccaa gggc          54

<210> SEQ ID NO 15
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Thr Thr Pro Ala Pro Arg Pro Pro Thr Pro Ala Pro Thr Ile Ala

```
1               5                   10                  15
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 16
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
accacgacgc cagcgccgcg accaccaaca ccggcgccca ccatcgcgtc gcaacccctg      60
tccctgcgcc cagaggcgtg ccggccagcg gcggggggcg cagtgcacac gaggggggctg    120 gacttcgcct gtgat                                                     135

<210> SEQ ID NO 17
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
acaacgacgc cagcgccgcg accaccaaca ccggcgccca ccatcgcgtc gcaacccctg      60
tccctgaggc ctgaagcgtg ccggccagcg gcggggggcg cagtgcacac gaggggggctg   120 gacttcgctt gtgac                                                     135

<210> SEQ ID NO 18
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
accacgacgc cagcgccgcg accaccaaca ccggcgccca ccatcgcgtc gcaacccctg      60
tccctgcgcc ccgaggcgtg ccggccagcg gcggggggcg cagtgcacac gaggggggctg   120 gacttcgcct gtgat                                                     135

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 20
<211> LENGTH: 90
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctagacaatg agaagagcaa tggaaccatt atccatgtga aagggaaaca cctttgtcca    60
agtcccctat ttcccggacc ttctaagccc                                    90

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 22
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttttgggtgc tggtggtggt tgtggagtc ctggcttgct atagcttgct agtaacagtg     60
gcctttatta ttttctgggt g                                             81

<210> SEQ ID NO 23
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttttgggtat tggtagtagt gggcggagtc ctggcttgct atagtctgct agtaacagtg    60
gcttttatta tattttgggt g                                             81

<210> SEQ ID NO 24
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttttgggtgc tggtggtggt tgtggagtc ctggcttgct atagcttgct agtaacagtg     60
gcctttatta ttttctgggt g                                             81

<210> SEQ ID NO 25
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 26
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atctacatct gggcgccctt ggccgggact tgtggggtcc ttctcctgtc actggttatc      60
acccttattt gc                                                         72

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 28
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ctgagagtga agttcagcag gagcgcagac gcccccgcgt accagcaggg gcagaaccaa      60
ctctataacg agctcaatct aggaaggaga gaagagtacg atgttctaga caagagacgt     120
ggccgggacc ctgagatggg gggaaagcca cgaaggaaga accctcagga aggcctgtac     180
aacgaactac aaaaagataa aatggcggag gcctacagtg agattggcat gaaaggcgag     240
```

```
cgccggaggg gcaaggggca cgatggcctt taccagggcc tcagtacagc caccaaggac    300
acctatgacg cccttcacat gcaagctctg cccccctcgc                          339
```

<210> SEQ ID NO 29
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
ctgagagtga agttcagcag gagcgcagac gcccccgcgt accagcaggg ccagaaccag    60
ctctataacg agctcaatct aggacgaaga gaggagtacg atgttttgga caagagacgt   120
ggccgggacc ctgagatggg gggaaagccg agaaggaaga accctcagga aggcctgtac   180
aacgaactgc agaaagataa gatggcggag gcctacagtg agattggcat gaaaggcgag   240
cgccggaggg gcaaggggca cgacggcctt taccagggtc tcagtacagc caccaaggac   300
acctacgacg cccttcacat gcaggccctg cccccctcgc                         339
```

<210> SEQ ID NO 30
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ctgagagtga agttcagcag gagcgcagac gcccccgcgt accagcaggg ccagaaccag    60
ctctataacg agctcaatct aggacgaaga gaggagtacg atgttttgga caagaggcgt   120
ggccgggacc ctgagatggg gggaaagccg agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg cccccctcgc                         339
```

<210> SEQ ID NO 31
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Val Pro
            20                  25                  30

Asn Pro Asp Tyr Glu Pro Ile Arg Lys Gly Gln Arg Asp Leu Tyr Ser
        35                  40                  45

Gly Leu
    50
```

<210> SEQ ID NO 32
<211> LENGTH: 150
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 32
aagaaccgaa aagcaaaagc caagcctgtt acaagaggag caggggcagg aggccgacag      60
agagggcaaa acaaagaaag gcccccgccc gtcccaaacc cggattatga gccaattagg     120
aagggtcaga gagacctgta ttctgggctc                                      150

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
        35                  40

<210> SEQ ID NO 34
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
aaacgaggca gaaagaaact cctgtatata ttcaaacaac catttatgag accagtacaa      60
acaactcagg aggaggatgg ctgtagctgc cgattcccgg aagaagaaga aggtggctgt     120
gaa                                                                   123

<210> SEQ ID NO 35
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
aaacggggca gaaagaaact cctgtatata ttcaaacaac catttatgag accagtacaa      60
actactcaag aggaagatgg ctgtagctgc cgatttccag aagaagaaga aggaggatgt     120
gaa                                                                   123

<210> SEQ ID NO 36
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
aaacggggca gaaagaaact cctgtatata ttcaaacaac catttatgag accagtacaa      60
```

```
actactcaag aggaagatgg ctgtagctgc cgatttccag aagaagaaga aggaggatgt    120
gaa                                                                 123
```

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 38
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 40
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
atggctcttc ctgtgactgc actactgctg cccctggcct tacttcttca tgctgcgcgt    60
cct                                                                 63
```

<210> SEQ ID NO 41
<211> LENGTH: 22
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 41

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Glu Trp Thr Trp Val Phe Leu Phe Leu Leu Ser Val Thr Ala Gly
1               5                   10                  15

Val His Ser

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Ala Leu Pro Val Thr Ala Leu Leu Leu Pro Leu Ala Leu Leu Leu
1               5                   10                  15

His Ala Ala Arg Pro
            20

<210> SEQ ID NO 44
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atggctcttc ctgtgacagc tcttctgctg cccctggccc tgcttctgca tgctgctaga      60
cct                                                                   63

<210> SEQ ID NO 45
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45
```

```
Asn Cys Tyr Gln Phe Phe Asp Glu Ser Lys Asn Trp Tyr Glu Ser Gln
 50                  55                  60
Ala Ser Cys Met Ser Gln Asn Ala Ser Leu Leu Lys Val Tyr Ser Lys
 65                  70                  75                  80
Glu Asp Gln Asp Leu Leu Lys Leu Val Lys Ser Tyr His Trp Met Gly
                 85                  90                  95
Leu Val His Ile Pro Thr Asn Gly Ser Trp Gln Trp Glu Asp Gly Ser
                100                 105                 110
Ile Leu Ser Pro Asn Leu Leu Thr Ile Ile Glu Met Gln Lys Gly Asp
                115                 120                 125
Cys Ala Leu Tyr Ala Ser Ser Phe Lys Gly Tyr Ile Glu Asn Cys Ser
130                 135                 140
Thr Pro Asn Thr Tyr Ile Cys Met Gln Arg Thr Val Thr Thr Thr Pro
145                 150                 155                 160
Ala Pro Arg Pro Pro Thr Pro Ala Pro Thr Ile Ala Ser Gln Pro Leu
                165                 170                 175
Ser Leu Arg Pro Glu Ala Cys Arg Pro Ala Ala Gly Gly Ala Val His
                180                 185                 190
Thr Arg Gly Leu Asp Phe Ala Cys Asp Phe Trp Val Leu Val Val Val
                195                 200                 205
Gly Gly Val Leu Ala Cys Tyr Ser Leu Leu Val Thr Val Ala Phe Ile
210                 215                 220
Ile Phe Trp Val Lys Arg Gly Arg Lys Lys Leu Leu Tyr Ile Phe Lys
225                 230                 235                 240
Gln Pro Phe Met Arg Pro Val Gln Thr Thr Gln Glu Glu Asp Gly Cys
                245                 250                 255
Ser Cys Arg Phe Pro Glu Glu Glu Glu Gly Gly Cys Glu Leu Arg Val
                260                 265                 270
Lys Phe Ser Arg Ser Ala Asp Ala Pro Ala Tyr Gln Gln Gly Gln Asn
                275                 280                 285
Gln Leu Tyr Asn Glu Leu Asn Leu Gly Arg Arg Glu Glu Tyr Asp Val
                290                 295                 300
Leu Asp Lys Arg Arg Gly Arg Asp Pro Glu Met Gly Gly Lys Pro Arg
305                 310                 315                 320
Arg Lys Asn Pro Gln Glu Gly Leu Tyr Asn Glu Leu Gln Lys Asp Lys
                325                 330                 335
Met Ala Glu Ala Tyr Ser Glu Ile Gly Met Lys Gly Glu Arg Arg Arg
                340                 345                 350
Gly Lys Gly His Asp Gly Leu Tyr Gln Gly Leu Ser Thr Ala Thr Lys
                355                 360                 365
Asp Thr Tyr Asp Ala Leu His Met Gln Ala Leu Pro Pro Arg
370                 375                 380

<210> SEQ ID NO 46
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggctcttc ctgtgactgc actactgctg cccctggcct tacttcttca tgctgcgcgt      60 ccttttattca accaagaagt ccagattccc ttgaccgaaa gttactgcgg cccatgtccg     120
aaaaactgga tatgttataa aaataactgt taccagttct tcgatgaatc taaaaactgg     180
```

```
tatgagagcc aggcatcttg tatgtctcaa aatgccagcc tgctcaaagt atacagcaag    240
gaggaccagg atttacttaa actggtgaag tcatatcact ggatgggatt ggtacacatt    300
cccacaaatg gatcttggca gtgggaagac ggctccattc tctcacccaa cctactaaca    360
ataattgaaa tgcagaaggg agactgcgca ctctatgcat cgagctttaa aggttatata    420
gaaaactgtt caactccaaa tacatacatc tgcatgcaaa ggactgtaac aacgacgcca    480
gcgccgcgac caccaacacc ggcgcccacc atcgcgtcgc aacccctgtc cctgaggcct    540
gaagcgtgcc ggccagcggc ggggggcgca gtgcacacga ggggctgga cttcgcttgt    600 gacttttggg tattggtagt agtgggcgga gtcctggctt gctatagtct gctagtaaca    660
gtggctttta ttatattttg ggtgaaacga ggcagaaaga aactcctgta tatattcaaa    720
caaccattta tgagaccagt acaaacaact caggaggagg atggctgtag ctgccgattc    780
ccggaagaag aagaaggtgg ctgtgaactg agagtgaagt tcagcaggag cgcagacgcc    840
cccgcgtacc agcaggggca gaaccaactc tataacgagc tcaatctagg aaggagagaa    900
gagtacgatg ttctagacaa gagacgtggc cgggaccctg agatgggggg aaagccacga    960
aggaagaacc ctcaggaagg cctgtacaac gaactacaaa aagataaaat ggcggaggcc   1020
tacagtgaga ttggcatgaa aggcgagcgc cggaggggca aggggcacga tggcctttac   1080
cagggcctca gtacagccac caaggacacc tatgacgccc ttcacatgca agctctgccc   1140
cctcgc                                                             1146
```

<210> SEQ ID NO 47
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Phe Trp Val Leu Val Val Gly Val Leu Ala
            180                 185                 190

Cys Tyr Ser Leu Leu Val Thr Val Ala Phe Ile Ile Phe Trp Val Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360

<210> SEQ ID NO 48
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ttattcaacc aagaagtcca gattcccttg accgaaagtt actgcggccc atgtccgaaa      60
aactggatat gttataaaaa taactgttac cagttcttcg atgaatctaa aaactggtat     120
gagagccagg catcttgtat gtctcaaaat gccagcctgc tcaaagtata cagcaaggag     180
gaccaggatt tacttaaact ggtgaagtca tatcactgga tgggattggt acacattccc     240
acaaatggat cttggcagtg gaagacggc tccattctct cacccaacct actaacaata     300
attgaaatgc agaagggaga ctgcgcactc tatgcatcga gctttaaagg ttatatagaa     360
aactgttcaa ctccaaatac atacatctgc atgcaaagga ctgtaacaac gacgccagcg     420
ccgcgaccac caacaccggc gcccaccatc gcgtcgcaac ccctgtccct gaggcctgaa     480
gcgtgccggc cagcggcggg gggcgcagtg cacacgaggg ggctggactt cgcttgtgac     540
ttttgggtat tggtagtagt gggcggagtc ctggcttgct atagtctgct agtaacagtg     600
gcttttatta tattttgggt gaaacgaggc agaagaaac tcctgtatat attcaaacaa     660
ccatttatga gaccagtaca aacaactcag gaggaggatg gctgtagctg ccgattcccg     720
gaagaagaag aaggtggctg tgaactgaga gtgaagttca gcaggagcgc agacgccccc     780
gcgtaccagc aggggcagaa ccaactctat aacgagctca atctaggaag gagagaagag     840
tacgatgttc tagacaagag acgtggccgg gaccctgaga tgggggaaaa gccacgaagg     900
aagaaccctc aggaaggcct gtacaacgaa ctacaaaaag ataaaatggc ggaggcctac     960

```
agtgagattg gcatgaaagg cgagcgccgg aggggcaagg ggcacgatgg cctttaccag   1020
ggcctcagta cagccaccaa ggacacctat gacgcccttc acatgcaagc tctgcccccct  1080 cgc                                                                 1083
```

<210> SEQ ID NO 49
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
    210                 215                 220

Ile Phe Trp Val Lys Arg Gly Arg Lys Lys Leu Leu Tyr Ile Phe Lys
225                 230                 235                 240

Gln Pro Phe Met Arg Pro Val Gln Thr Thr Gln Glu Glu Asp Gly Cys
                245                 250                 255

Ser Cys Arg Phe Pro Glu Glu Glu Gly Gly Cys Glu Lys Asn Arg
            260                 265                 270

Lys Ala Lys Ala Lys Pro Val Thr Arg Gly Ala Gly Ala Gly Gly Arg
        275                 280                 285

Gln Arg Gly Gln Asn Lys Glu Arg Pro Pro Val Pro Asn Pro Asp
    290                 295                 300

Tyr Glu Pro Ile Arg Lys Gly Gln Arg Asp Leu Tyr Ser Gly Leu Leu
305                 310                 315                 320

Arg Val Lys Phe Ser Arg Ser Ala Asp Ala Pro Ala Tyr Gln Gln Gly
                325                 330                 335
```

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
355                 360                 365

Pro Arg Arg Lys Asn Pro Gln Glu Gly Leu Tyr Asn Glu Leu Gln Lys
        370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 50
<211> LENGTH: 1296
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggctcttc ctgtgacagc tcttctgctg cccctggccc tgcttctgca tgctgctaga      60
cctttattca accaagaagt ccaaattccc ttgaccgaaa gttactgtgg cccatgtcct     120
aaaaactgga tatgttacaa aaataactgt taccaattct tcgatgaaag taaaaactgg     180
tatgagagcc aggcttcttg tatgtctcaa aatgccagcc ttctgaaagt atacagcaag     240
gaggaccagg atttacttaa actggtgaag tcatatcatt ggatgggact agtacacatt     300
ccaacaaatg gatcttggca gtgggaagac ggctccattc tctcacccaa cctactaaca     360
ataattgaaa tgcagaaggg agactgtgca ctctatgcat cgagctttaa aggctatata     420
gaaaactgtt caactccaaa tacatacatc tgcatgcaaa ggactgtgac cacgacgcca     480
gcgccgcgac caccaacacc ggcgcccacc atcgcgtcgc aacccctgtc cctgcgccca     540
gaggcgtgcc ggccagcggc gggggcgca gtgcacacga gggggctgga cttcgcctgt     600 gattttggg tgctggtggt ggttggtgga gtcctggctt gctatagctt gctagtaaca     660 gtggcctta ttattttctg ggtgaaacgg ggcagaaaga aactcctgta tatattcaaa     720 caaccatttta tgagaccagt acaaactact caagaggaag atggctgtag ctgccgattt     780
ccagaagaag aagaaggagg atgtgaaaag aaccgaaaag caaaagccaa gcctgttaca     840
agaggagcag gggcaggagg ccgacagaga gggcaaaaca agaaaaggcc cccgcccgtc     900
ccaaacccgg attatgagcc aattaggaag ggtcagagag acctgtattc tgggctcctg     960
agagtgaagt tcagcaggag cgcagacgcc cccgcgtacc agcagggcca gaaccagctc    1020
tataacgagc tcaatctagg acgaagagag gagtacgatg ttttggacaa gagacgtggc    1080
cgggaccctg agatgggggg aaagccgaga aggaagaacc ctcaggaagg cctgtacaac    1140
gaactgcaga agataagat ggcggaggcc tacagtgaga ttggcatgaa aggcgagcgc    1200 cggagggggca aggggcacga cggcctttac cagggtctca gtacagccac caaggacacc    1260
tacgacgccc ttcacatgca ggccctgccc cctcgc                              1296

<210> SEQ ID NO 51
<211> LENGTH: 411
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 51

```
Leu Phe Asn Gln Glu Val Gln Ile Pro Leu Thr Glu Ser Tyr Cys Gly
1               5                   10                  15
Pro Cys Pro Lys Asn Trp Ile Cys Tyr Lys Asn Asn Cys Tyr Gln Phe
            20                  25                  30
Phe Asp Glu Ser Lys Asn Trp Tyr Glu Ser Gln Ala Ser Cys Met Ser
        35                  40                  45
Gln Asn Ala Ser Leu Leu Lys Val Tyr Ser Lys Glu Asp Gln Asp Leu
50                  55                  60
Leu Lys Leu Val Lys Ser Tyr His Trp Met Gly Leu Val His Ile Pro
65                  70                  75                  80
Thr Asn Gly Ser Trp Gln Trp Glu Asp Gly Ser Ile Leu Ser Pro Asn
                85                  90                  95
Leu Leu Thr Ile Ile Glu Met Gln Lys Gly Asp Cys Ala Leu Tyr Ala
            100                 105                 110
Ser Ser Phe Lys Gly Tyr Ile Glu Asn Cys Ser Thr Pro Asn Thr Tyr
        115                 120                 125
Ile Cys Met Gln Arg Thr Val Thr Thr Thr Pro Ala Pro Arg Pro Pro
130                 135                 140
Thr Pro Ala Pro Thr Ile Ala Ser Gln Pro Leu Ser Leu Arg Pro Glu
145                 150                 155                 160
Ala Cys Arg Pro Ala Ala Gly Gly Ala Val His Thr Arg Gly Leu Asp
                165                 170                 175
Phe Ala Cys Asp Phe Trp Val Leu Val Val Val Gly Gly Val Leu Ala
            180                 185                 190
Cys Tyr Ser Leu Leu Val Thr Val Ala Phe Ile Ile Phe Trp Val Lys
        195                 200                 205
Arg Gly Arg Lys Lys Leu Leu Tyr Ile Phe Lys Gln Pro Phe Met Arg
210                 215                 220
Pro Val Gln Thr Thr Gln Glu Glu Asp Gly Cys Ser Cys Arg Phe Pro
225                 230                 235                 240
Glu Glu Glu Glu Gly Gly Cys Glu Lys Asn Arg Lys Ala Lys Ala Lys
                245                 250                 255
Pro Val Thr Arg Gly Ala Gly Ala Gly Gly Arg Gln Arg Gly Gln Asn
            260                 265                 270
Lys Glu Arg Pro Pro Pro Val Pro Asn Pro Asp Tyr Glu Pro Ile Arg
        275                 280                 285
Lys Gly Gln Arg Asp Leu Tyr Ser Gly Leu Leu Arg Val Lys Phe Ser
290                 295                 300
Arg Ser Ala Asp Ala Pro Ala Tyr Gln Gln Gly Gln Asn Gln Leu Tyr
305                 310                 315                 320
Asn Glu Leu Asn Leu Gly Arg Arg Glu Glu Tyr Asp Val Leu Asp Lys
                325                 330                 335
Arg Arg Gly Arg Asp Pro Glu Met Gly Gly Lys Pro Arg Arg Lys Asn
            340                 345                 350
Pro Gln Glu Gly Leu Tyr Asn Glu Leu Gln Lys Asp Lys Met Ala Glu
        355                 360                 365
Ala Tyr Ser Glu Ile Gly Met Lys Gly Glu Arg Arg Arg Gly Lys Gly
370                 375                 380
His Asp Gly Leu Tyr Gln Gly Leu Ser Thr Ala Thr Lys Asp Thr Tyr
```

```
                385                 390                 395                 400
Asp Ala Leu His Met Gln Ala Leu Pro Pro Arg
                    405                 410
```

<210> SEQ ID NO 52
<211> LENGTH: 1233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | | | | |
|---|---|---|---|---|
| ttattcaacc | aagaagtcca | aattcccttg | accgaaagtt | actgtggccc atgtcctaaa | 60 |
| aactggatat | gttacaaaaa | taactgttac | caattcttcg | atgaaagtaa aaactggtat | 120 |
| gagagccagg | cttcttgtat | gtctcaaaat | gccagccttc | tgaaagtata cagcaaggag | 180 |
| gaccaggatt | tacttaaact | ggtgaagtca | tatcattgga | tgggactagt acacattcca | 240 |
| acaaatggat | cttggcagtg | ggaagacggc | tccattctct | cacccaacct actaacaata | 300 |
| attgaaatgc | agaagggaga | ctgtgcactc | tatgcatcga | gctttaaagg ctatatagaa | 360 |
| aactgttcaa | ctccaaatac | atacatctgc | atgcaaagga | ctgtgaccac gacgccagcg | 420 |
| ccgcgaccac | caacaccggc | gcccaccatc | gcgtcgcaac | ccctgtccct gcgcccagag | 480 |
| gcgtgccggc | cagcggcggg | gggcgcagtg | cacacgaggg | ggctggactt cgcctgtgat | 540 |
| ttttgggtgc | tggtggtggt | tggtggagtc | ctggcttgct | atagcttgct agtaacagtg | 600 |
| gcctttatta | ttttctgggt | gaaacggggc | agaaagaaac | tcctgtatat attcaaacaa | 660 |
| ccatttatga | gaccagtaca | aactactcaa | gaggaagatg | gctgtagctg ccgatttcca | 720 |
| gaagaagaag | aaggaggatg | tgaaaagaac | cgaaaagcaa | agccaagcc tgttacaaga | 780 |
| ggagcagggg | caggaggccg | acagagaggg | caaaacaaag | aaaggccccc gcccgtccca | 840 |
| aacccggatt | atgagccaat | aggaagggt | cagagagacc | tgtattctgg gctcctgaga | 900 |
| gtgaagttca | gcaggagcgc | agacgccccc | gcgtaccagc | agggccagaa ccagctctat | 960 |
| aacgagctca | atctaggacg | aagagaggag | tacgatgttt | tggacaagag acgtggccgg | 1020 |
| gaccctgaga | tggggggaaa | gccgagaagg | aagaaccctc | aggaaggcct gtacaacgaa | 1080 |
| ctgcagaaag | ataagatggc | ggaggcctac | agtgagattg | gcatgaaagg cgagcgccgg | 1140 |
| aggggcaagg | ggcacgacgg | cctttaccag | ggtctcagta | cagccaccaa ggacacctac | 1200 |
| gacgcccttc | acatgcaggc | cctgccccct | cgc | | 1233 |

<210> SEQ ID NO 53
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
```

```
                50                  55                  60
Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Tyr His Trp Met Gly
                 85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
    210                 215                 220

Ile Phe Trp Val Lys Arg Gly Arg Lys Lys Leu Leu Tyr Ile Phe Lys
225                 230                 235                 240

Gln Pro Phe Met Arg Pro Val Gln Thr Thr Gln Glu Glu Asp Gly Cys
                245                 250                 255

Ser Cys Arg Phe Pro Glu Glu Glu Gly Gly Cys Glu Leu Arg Val
            260                 265                 270

Lys Phe Ser Arg Ser Ala Asp Ala Pro Ala Tyr Gln Gln Gly Gln Asn
        275                 280                 285

Gln Leu Tyr Asn Glu Leu Asn Leu Gly Arg Arg Glu Glu Tyr Asp Val
    290                 295                 300

Leu Asp Lys Arg Arg Gly Arg Asp Pro Glu Met Gly Gly Lys Pro Arg
305                 310                 315                 320

Arg Lys Asn Pro Gln Glu Gly Leu Tyr Asn Glu Leu Gln Lys Asp Lys
                325                 330                 335

Met Ala Glu Ala Tyr Ser Glu Ile Gly Met Lys Gly Glu Arg Arg Arg
            340                 345                 350

Gly Lys Gly His Asp Gly Leu Tyr Gln Gly Leu Ser Thr Ala Thr Lys
        355                 360                 365

Asp Thr Tyr Asp Ala Leu His Met Gln Ala Leu Pro Pro Arg
    370                 375                 380

<210> SEQ ID NO 54
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ala Leu Pro Val Thr Ala Leu Leu Leu Pro Leu Ala Leu Leu Leu
 1               5                  10                  15

His Ala Ala Arg Pro Leu Phe Asn Gln Glu Val Gln Ile Pro Leu Thr
            20                  25                  30
```

-continued

```
Glu Ser Tyr Cys Gly Pro Cys Pro Lys Asn Trp Ile Cys Tyr Lys Asn
             35                  40                  45

Asn Cys Tyr Gln Phe Phe Asp Glu Ser Lys Asn Trp Tyr Glu Ser Gln
 50                  55                  60

Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Tyr His Trp Met Gly
                 85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
            195                 200                 205

Gly Gly Val Leu Ala Cys Tyr Ser Leu Leu Val Thr Val Ala Phe Ile
            210                 215                 220

Ile Phe Trp Val Lys Arg Gly Arg Lys Lys Leu Leu Tyr Ile Phe Lys
225                 230                 235                 240

Gln Pro Phe Met Arg Pro Val Gln Thr Thr Gln Glu Glu Asp Gly Cys
                245                 250                 255

Ser Cys Arg Phe Pro Glu Glu Glu Gly Gly Cys Glu Leu Arg Val Lys Phe Ser Arg Ser Ala Asp Ala Pro Ala Tyr Gln Gln Gly
            260                 265                 270

Lys Ala Lys Ala Lys Pro Val Thr Arg Gly Ala Gly Ala Gly Gly Arg
            275                 280                 285

Gln Arg Gly Gln Asn Lys Glu Arg Pro Pro Val Pro Asn Pro Asp
290                 295                 300

Tyr Glu Pro Ile Arg Lys Gly Gln Arg Asp Leu Tyr Ser Gly Leu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
            355                 360                 365

Pro Arg Arg Lys Asn Pro Gln Glu Gly Leu Tyr Asn Glu Leu Gln Lys
            370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 55
<211> LENGTH: 405
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 55
ttattcaacc aagaagtcca aattcccttg accgaaagtt actgtggccc atgtcctaag     60
aactggatat gttacaaaaa taactgttac caattcttcg atgaatctaa gaattggtat    120
gagagccagg cttcttgtat gtctcaaaat gccagccttc ttaaagtata cagcaaagag    180
gaccaggatt tacttaaact ggtgaagtca tatcattgga tgggactagt acacattcca    240
acaaatggat cttggcagtg gaagacggc tccattctct cacccaacct actaacaata    300
attgaaatgc agaagggaga ctgtgcactc tatgcatcga gctttaaagg ctatatagaa    360
aactgttcaa ctccaaatac atatatttgc atgcaaagga ctgtg                   405

<210> SEQ ID NO 56
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
accacgacgc cagcgccgcg accaccaaca ccggcgccca ccatcgcgtc gcaacccctg     60
tccctgaggc ctgaagcgtg ccggccagcg gcgggcggcg cagtgcacac gagagggctg    120
gacttcgcct gtgat                                                    135

<210> SEQ ID NO 57
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atctacatct gggcgcccctt ggccgggact tgtggggtcc ttctcctgtc actggttatc    60
accctttact gc                                                        72

<210> SEQ ID NO 58
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ctgagagtga agttcagcag gagcgcagac gcccccgcgt accagcaagg gcagaaccag     60
ctctataacg agctcaatct aggacgaaga gaggagtacg atgttttgga caagaggcgt    120
ggccgggacc ctgagatggg gggaaagccg agaaggaaga accctcagga aggcctgtac    180
aatgaactgc agaaagataa gatggcgag gcctacagtg agattgggat gaaaggcgag    240
cgccggaggg gcaaggggca cgatggcctt taccagggtc tcagtacagc caccaaggac    300
acctacgacg cccttcacat gcaagctctg cccctcgct ga                       342

<210> SEQ ID NO 59
<211> LENGTH: 342

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
ctgagagtta agttcagcag gagcgccgac gcccctgcct accagcaagg acagaatcaa      60
ctgtacaacg agctgaacct gggcagacgg gaggaatacg atgtgctgga caagaggaga     120
ggcagagacc ccgagatggg cggcaaacct agaagaaaga accccagga gggcctgtat      180 aacgagctcc agaaggacaa gatggccgag gcctacagcg agatcggcat gaagggcgaa     240
agaagaagag gcaagggcca cgacggcctc taccagggct taagcacagc tacaaaggac     300
acctacgacg ccctgcacat gcaggccctg cccctagat ga                        342

<210> SEQ ID NO 60
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ctgagagtga agttcagcag gagcgcagac gcccccgcgt accagcaagg gcagaaccag      60
ctctataacg agctcaatct aggacgaaga gaggagtacg atgttttgga caagaggcgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaagctctg cccctcgct ga                        342

<210> SEQ ID NO 61
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55

<210> SEQ ID NO 62
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
aagaaccgca aagcaaaggc aaaacccgtc acacgaggag cgggcgcagg gggacgacaa     60
```
cgcggtcaga ataaggaacg cccgcctcca gtaccaaatc cagattatga accaattcgg    120
aagggacaac gcgatctcta ctccggtctc aatcagaggc gaatt    165

<210> SEQ ID NO 63
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 64
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
aagagaggcc ggaagaagct gctgtacatc ttcaagcagc ccttcatgag acctgtgcag    60
accacacagg aggaagacgg ctgcagctgt agattccccg aggaagagga gggcggctgt    120
gagctg    126

<210> SEQ ID NO 65
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atggctcttc ctgtgacagc tcttctgctg cccctggccc tgcttctgca tgctgctaga    60
cct    63

<210> SEQ ID NO 66
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
            35                  40                  45

Gln Asn Ala Ser Leu Leu Lys Val Tyr Ser Lys Glu Asp Gln Asp Leu
            50                  55                  60

Leu Lys Leu Val Lys Ser Tyr His Trp Met Gly Leu Val His Ile Pro
 65                  70                  75                  80

Thr Asn Gly Ser Trp Gln Trp Glu Asp Gly Ser Ile Leu Ser Pro Asn
                 85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
                180                 185                 190

Val Leu Leu Leu Ser Leu Val Ile Thr Leu Tyr Cys Lys Arg Gly Arg
                195                 200                 205

Lys Lys Leu Leu Tyr Ile Phe Lys Gln Pro Phe Met Arg Pro Val Gln
        210                 215                 220

Thr Thr Gln Glu Glu Asp Gly Cys Ser Cys Arg Phe Pro Glu Glu Glu
225                 230                 235                 240

Glu Gly Gly Cys Glu Leu Arg Val Lys Phe Ser Arg Ser Ala Asp Ala
                245                 250                 255

Pro Ala Tyr Gln Gln Gly Gln Asn Gln Leu Tyr Asn Glu Leu Asn Leu
            260                 265                 270

Gly Arg Arg Glu Glu Tyr Asp Val Leu Asp Lys Arg Arg Gly Arg Asp
        275                 280                 285

Pro Glu Met Gly Gly Lys Pro Arg Arg Lys Asn Pro Gln Glu Gly Leu
    290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
                325                 330                 335

Gln Gly Leu Ser Thr Ala Thr Lys Asp Thr Tyr Asp Ala Leu His Met
            340                 345                 350

Gln Ala Leu Pro Pro Arg
        355

<210> SEQ ID NO 67
<211> LENGTH: 2399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
cgtgaggctc cggtgcccgt cagtgggcag agcgcacatc gcccacagtc cccgagaagt      60 tgggggagg ggtcggcaat tgaaccggtg cctagagaag gtggcgcggg gtaaactggg      120
aaagtgatgt cgtgtactgg ctccgccttt ttcccgaggg tgggggagaa ccgtatataa      180
gtgcagtagt cgccgtgaac gttcttttc gcaacgggtt tgccgccaga acacaggtaa      240
gtgccgtgtg tggttcccgc gggcctggcc tctttacggg ttatggccct tgcgtgcctt      300
gaattacttc cacgcccctg ctgcagtac gtgattcttg atcccgagct cgggttgga      360

```
agtgggtggg agagttcgag gccttgcgct taaggagccc cttcgcctcg tgcttgagtt    420
gaggcctggc ttgggcgctg gggccgccgc gtgcgaatct ggtggcacct tcgcgcctgt    480
ctcgctgctt tcgataagtc tctagccatt taaaatttt gatgacctgc tgcgacgctt    540
tttttctggc aagatagtct tgtaaatgcg gccaagatc tgcacactgg tatttcggtt    600
tttggggccg cgggcggcga cggggcccgt gcgtcccagc gcacatgttc ggcgaggcgg    660
ggcctgcgag cgcggccacc gagaatcgga cggggggtagt ctcaagctgg ccggcctgct    720
ctggtgcctg gcctcgcgcc gccgtgtatc gccccgccct gggcggcaag gctggcccgg    780
tcggcaccag ttgcgtgagc ggaaagatgg ccgcttcccg gccctgctgc agggagctca    840
aaatggagga cgcggcgctc gggagagcgg gcgggtgagt cacccacaca aaggaaaagg    900
gcctttccgt cctcagccgt cgcttcatgt gactccacgg agtaccgggc gccgtccagg    960
cacctcgatt agttctcgag cttttggagt acgtcgtctt taggttgggg ggagggttt   1020
tatgcgatgg agtttcccca cactgagtgg gtggagactg aagttaggcc agcttggcac   1080
ttgatgtaat tctccttgga atttgcccctt tttgagtttg gatcttggtt cattctcaag   1140
cctcagacag tggttcaaag ttttttttctt ccatttcagg tgtcgtgaaa actacccccta   1200
aaagccaaag cgccgccacc atggctcttc ctgtgacagc tcttctgctg cccctggccc   1260
tgcttctgca tgctgctaga cctgagcaaa agttgatttc tgaggaagac ctcgccggca   1320
gtttattcaa ccaagaagtc caaattccct tgaccgaaag ttactgtggc ccatgtccta   1380
agaactggat atgttacaaa ataactgtt accaattctt cgatgaatct aagaattggt   1440
atgagagcca ggcttcttgt atgtctcaaa atgccagcct tcttaaagta tacagcaaag   1500
aggaccagga tttacttaaa ctggtgaagt catatcattg gatgggacta gtacacattc   1560
caacaaatgg atcttggcag tgggaagacg gctccattct ctcacccaac ctactaacaa   1620
taattgaaat gcagaaggga gactgtgcac tctatgcatc gagctttaaa ggctatatag   1680
aaaactgttc aactccaaat acatatattt gcatgcaaag gactgtgacc acgacgccag   1740
cgccgcgacc accaacaccg cgcccccacca tcgcgtcgca accccctgtcc ctgaggcctg   1800
aagcgtgccg gccagcggcg ggcggcgcag tgcacacgag agggctggac ttcgcctgtg   1860
atatctacat ctgggcgccc ttggccggga cttgtggggt ccttctcctg tcactggtta   1920
tcaccccttta ctgcaaacgg ggcagaaaga aactcctgta tatattcaaa caaccattta   1980
tgagaccagt acaaactact caagaggaag atggctgtag ctgccgattt ccagaagaag   2040
aagaaggagg atgtgaactg agagtgaagt tcagcaggag cgcagacgcc cccgcgtacc   2100
agcaagggca gaaccagctc tataacgagc tcaatctagg acgaagagag gagtacgatg   2160
ttttggacaa gaggcgtggc cgggaccctg agatgggggg aaagccgaga aggaagaacc   2220
ctcaggaagg cctgtacaat gaactgcaga agataagat ggcggaggcc tacagtgaga   2280
ttgggatgaa aggcgagcgc cggaggggca agggcacga tggcctttac cagggtctca   2340
gtacagccac caaggacacc tacgacgccc ttcacatgca agctctgccc cctcgctga   2399
```

<210> SEQ ID NO 68
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
                100                 105                 110

Ser Ser Phe Lys Gly Tyr Ile Glu Asn Cys Ser Thr Pro Asn Thr Tyr
            115                 120                 125

Ile Cys Met Gln Arg Thr Val Thr Thr Pro Ala Pro Arg Pro Pro
            130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Phe Trp Val Leu Val Val Gly Val Leu Ala
                180                 185                 190

Cys Tyr Ser Leu Leu Val Thr Val Ala Phe Ile Ile Phe Trp Val Lys
            195                 200                 205

Arg Gly Arg Lys Lys Leu Leu Tyr Ile Phe Lys Gln Pro Phe Met Arg
210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
            245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
            275                 280                 285

Gly Arg Asp Pro Glu Met Gly Gly Lys Pro Arg Arg Lys Asn Pro Gln
            290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
            325                 330                 335

Gly Leu Tyr Gln Gly Leu Ser Thr Ala Thr Lys Asp Thr Tyr Asp Ala
                340                 345                 350

Leu His Met Gln Ala Leu Pro Pro Arg
            355                 360

<210> SEQ ID NO 69
<211> LENGTH: 2408
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 69

```
cgtgaggctc cggtgcccgt cagtgggcag agcgcacatc gcccacagtc cccgagaagt      60
tgggggagg ggtcggcaat tgaaccggtg cctagagaag gtggcgcggg gtaaactggg      120
aaagtgatgt cgtgtactgg ctccgccttt ttcccgaggg tgggggagaa ccgtatataa      180
gtgcagtagt cgccgtgaac gttctttttc gcaacgggtt tgccgccaga acacaggtaa      240
gtgccgtgtg tggttcccgc gggcctggcc tctttacggg ttatggccct tgcgtgcctt      300
gaattacttc cacgcccctg ctgcagtac gtgattcttg atcccgagct tcgggttgga      360
agtgggtggg agagttcgag gccttgcgct taaggagccc cttcgcctcg tgcttgagtt      420
gaggcctggc ttgggcgctg gggccgccgc gtgcgaatct ggtggcacct tcgcgcctgt      480
ctcgctgctt tcgataagtc tctagccatt taaaattttt gatgacctgc tgcgacgctt      540
tttttctggc aagatagtct tgtaaatgcg ggccaagatc tgcacactgg tatttcggtt      600
tttgggccg cgggcggcga cggggcccgt gcgtcccagc gcacatgttc ggcgaggcgg      660
ggcctgcgag cgcggccacc gagaatcgga cgggggtagt ctcaagctgg ccggcctgct      720
ctggtgcctg gcctcgcgcc gccgtgtatc gccccgccct gggcggcaag gctggcccgg      780
tcggcaccag ttgcgtgagc ggaaagatgg ccgcttcccg gccctgctgc agggagctca      840
aaatggagga cgcggcgctc gggagagcgg gcgggtgagt cacccacaca aaggaaaagg      900
gccttccgt cctcagccgt cgcttcatgt gactccacgg agtaccgggc gccgtccagg      960
cacctcgatt agttctcgag cttttggagt acgtcgtctt taggttgggg ggaggggttt     1020
tatgcgatgg agtttcccca cactgagtgg gtggagactg aagttaggcc agcttggcac     1080
ttgatgtaat tctccttgga atttgccctt tttgagtttg gatcttggtt cattctcaag     1140
cctcagacag tggttcaaag ttttttttctt ccatttcagg tgtcgtgaaa actaccccta     1200
aaagccaaag cgccgccacc atggctcttc ctgtgacagc tcttctgctg ccctggccc      1260
tgcttctgca tgctgctaga cctgagcaaa agttgatttc tgaggaagac ctcgccggca     1320
gtttattcaa ccaagaagtc caaattccct tgaccgaaag ttactgtggc ccatgtccta     1380
agaactggat atgttacaaa ataactgttt accaattctt cgatgaatct aagaattggt     1440
atgagagcca ggcttcttgt atgtctcaaa atgccagcct tcttaaagta tacagcaaag     1500
aggaccagga tttacttaaa ctggtgaagt catatcattg gatgggacta gtacacattc     1560
caacaaatgg atcttggcag tgggaagacg gctccattct ctcacccaac ctactaacaa     1620
taattgaaat gcagaaggga gactgtgcac tctatgcatc gagctttaaa ggctatatag     1680
aaaactgttc aactccaaat acatatattt gcatgcaaag gactgtgacc acgacgccag     1740
cgccgcgacc accaacaccg gcgcccacca tcgcgtcgca acccctgtcc ctgaggcctg     1800
aagcgtgccg gccagcggcg ggcggcgcag tgcacacgag agggctggac ttcgcctgtg     1860
atttttgggt gctggtggtg gttggtggag tcctggcttg ctatagcttg ctagtaacag     1920
tggcctttat tattttctgg gtcaaacggg gcagaaagaa actcctgtat atattcaaac     1980
aaccatttat gagaccagta caaactactc aagaggaaga tggctgtagc tgccgatttc     2040
cagaagaaga agaaggagga tgtgaactga gagtgaagtt cagcaggagc gcagacgccc     2100
ccgcgtacca gcaagggcag aaccagctct ataacgagct caatctagga cgaagagagg     2160
agtacgatgt tttggacaag aggcgtggcc gggaccctga gatgggggga aagccgagaa     2220
ggaagaaccc tcaggaaggc ctgtacaatg aactgcagaa agataagatg gcggaggcct     2280
acagtgagat tgggatgaaa ggcgagcgcc ggaggggcaa ggggcacgat ggcctttacc     2340
```

-continued

```
agggtctcag tacagccacc aaggacacct acgacgccct tcacatgcaa gctctgcccc    2400
ctcgctga                                                             2408
```

<210> SEQ ID NO 70
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Ile Tyr Ile Trp Ala Pro Leu Ala Gly Thr Cys Gly Val Leu
            180                 185                 190

Leu Leu Ser Leu Val Ile Thr Leu Tyr Cys Lys Arg Gly Arg Lys Lys
        195                 200                 205

Leu Leu Tyr Ile Phe Lys Gln Pro Phe Met Arg Pro Val Gln Thr Thr
    210                 215                 220

Gln Glu Glu Asp Gly Cys Ser Cys Arg Phe Pro Glu Glu Glu Glu Gly
225                 230                 235                 240

Gly Cys Glu Leu Lys Asn Arg Lys Ala Lys Ala Lys Pro Val Thr Arg
                245                 250                 255

Gly Ala Gly Ala Gly Gly Arg Gln Arg Gly Gln Asn Lys Glu Arg Pro
            260                 265                 270

Pro Pro Val Pro Asn Pro Asp Tyr Glu Pro Ile Arg Lys Gly Gln Arg
        275                 280                 285

Asp Leu Tyr Ser Gly Leu Asn Gln Arg Arg Ile Leu Arg Val Lys Phe
    290                 295                 300

Ser Arg Ser Ala Asp Ala Pro Ala Tyr Gln Gln Gly Gln Asn Gln Leu
305                 310                 315                 320

Tyr Asn Glu Leu Asn Leu Gly Arg Arg Glu Glu Tyr Asp Val Leu Asp
                325                 330                 335
```

```
Lys Arg Arg Gly Arg Asp Pro Glu Met Gly Gly Lys Pro Arg Arg Lys
                340                 345                 350

Asn Pro Gln Glu Gly Leu Tyr Asn Glu Leu Gln Lys Asp Lys Met Ala
            355                 360                 365

Glu Ala Tyr Ser Glu Ile Gly Met Lys Gly Glu Arg Arg Arg Gly Lys
        370                 375                 380

Gly His Asp Gly Leu Tyr Gln Gly Leu Ser Thr Ala Thr Lys Asp Thr
385                 390                 395                 400

Tyr Asp Ala Leu His Met Gln Ala Leu Pro Pro Arg
                405                 410

<210> SEQ ID NO 71
<211> LENGTH: 1832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
cgcggaatga aagaccccac ctgtaggttt ggcaagctag cttaagtaac gccattttgc      60
aaggcatgga aaatacataa ctgagaatag agaagttcag atcaaggtta ggaacagaga    120
gacagcagaa tatgggccaa acaggatatc tgtggtaagc agttcctgcc ccggctcagg    180
gccaagaaca gatggtcccc agatgcggtc ccgccctcag cagtttctag gaaccatca    240 gatgtttcca gggtgcccca aggacctgaa atgaccctgt gccttatttg aactaaccaa    300
tcagttcgct tctcgcttct gttcgcgcgc ttctgctccc cgagctcaat aaaagagccc    360
acaacccctc actcggcgcg ccagtccttc gaagtagatc tttgtcgatc ctaccatcca    420
ctcgacacac ccgccagcgg ccgctgccaa gcttccgagc tctcgaatta attcacgccg    480
ccaccatggc tcttcctgtg acagctcttc tgctgcccct ggccctgctt ctgcatgctg    540
ctagacctga gcaaaagttg atttctgagg aagacctcgc cggcagttta ttcaaccaag    600
aagtccaaat tcccttgacc gaaagttact gtggcccatg tcctaagaac tggatatgtt    660
acaaaaataa ctgttaccaa ttcttcgatg aatctaagaa ttggtatgag gccaggcttc    720 ttgtatgtc tcaaaatgcc agccttctta agtatacag caaagaggac caggatttac     780
ttaaactggt gaagtcatat cattggatgg gactagtaca cattccaaca aatgatcttc    840
ggcagtggga gacggctcc attctctcac ccaacctact aacaataatt gaaatgcaga     900
agggagactg tgcactctat gcatcgagct ttaaaggcta tatagaaaac tgttcaactc    960
caaatacata tatttgcatg caaaggactg tgaccaccac tcctgctcca agacctccta   1020 ccccgctcc tacaatcgcc agccaacctc tgagcctgag accggaggca tgcagacctg    1080 cggcagggg agcagttcac acaagaggct tggacttcgc ttgcgacatc tacatctggg    1140 ccctctggc cggcacatgc ggagttcttc ttcttagcct ggtgatcacc ctgtactgca    1200
agagaggccg gaagaagctg ctgtacatct tcaagcagcc cttcatgaga cctgtgcaga    1260
ccacacagga ggaagacggc tgcagctgta gattccccga ggaagaggag gcggctgtg    1320 agctgaagaa ccgcaaagca aggcaaaaac ccgtcacacg aggagcgggc caggggggac    1380
gacaacgcgg tcagaataag gaacgcccgc ctccagtacc aaatccagat tatgaaccaa    1440
ttcggaaggg acaacgcgat ctctactccg gtctcaatca gaggcgaatt ctgagagtta    1500
agttcagcag gagcgccgac gcccctgcct accagcaagg acagaatcaa ctgtacaacg    1560 agctgaaccct gggcagacgg gaggaatacg atgtgctgga caagaggaga ggcagagacc    1620
```

-continued

```
ccgagatggg cggcaaacct agaagaaaga accccagga gggcctgtat aacgagctcc    1680
agaaggacaa gatggccgag gcctacagcg agatcggcat gaagggcgaa agaagaagag    1740
gcaagggcca cgacggcctc taccagggct taagcacagc tacaaaggac acctacgacg    1800
ccctgcacat gcaggccctg cccctagat ga                                  1832
```

<210> SEQ ID NO 72
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
            180                 185                 190

Val Leu Leu Leu Ser Leu Val Ile Thr Leu Tyr Cys Lys Arg Gly Arg
        195                 200                 205

Lys Lys Leu Leu Tyr Ile Phe Lys Gln Pro Phe Met Arg Pro Val Gln
    210                 215                 220

Thr Thr Gln Glu Glu Asp Gly Cys Ser Cys Arg Phe Pro Glu Glu Glu
225                 230                 235                 240

Glu Gly Gly Cys Glu Lys Asn Arg Lys Ala Lys Ala Lys Pro Val Thr
                245                 250                 255

Arg Gly Ala Gly Ala Gly Gly Arg Gln Arg Gly Gln Asn Lys Glu Arg
            260                 265                 270

Pro Pro Pro Val Pro Asn Pro Asp Tyr Glu Pro Ile Arg Lys Gly Gln
        275                 280                 285

Arg Asp Leu Tyr Ser Gly Leu Leu Arg Val Lys Phe Ser Arg Ser Ala
    290                 295                 300

Asp Ala Pro Ala Tyr Gln Gln Gly Gln Asn Gln Leu Tyr Asn Glu Leu
305                 310                 315                 320
```

```
Asn Leu Gly Arg Arg Glu Glu Tyr Asp Val Leu Asp Lys Arg Arg Gly
            325                 330                 335

Arg Asp Pro Glu Met Gly Gly Lys Pro Arg Arg Lys Asn Pro Gln Glu
        340                 345                 350

Gly Leu Tyr Asn Glu Leu Gln Lys Asp Lys Met Ala Glu Ala Tyr Ser
    355                 360                 365

Glu Ile Gly Met Lys Gly Glu Arg Arg Arg Gly Lys Gly His Asp Gly
    370                 375                 380

Leu Tyr Gln Gly Leu Ser Thr Ala Thr Lys Asp Thr Tyr Asp Ala Leu
385                 390                 395                 400

His Met Gln Ala Leu Pro Pro Arg
                405

<210> SEQ ID NO 73
<211> LENGTH: 1814
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
```

| | | | | | |
|---|---|---|---|---|---|
| cgcggaatga | aagacccccac | ctgtaggttt | ggcaagctag | cttaagtaac | gccattttgc | 60 |
| aaggcatgga | aaatacataa | ctgagaatag | agaagttcag | atcaaggtta | ggaacagaga | 120 |
| gacagcagaa | tatgggccaa | acaggatatc | tgtggtaagc | agttcctgcc | ccggctcagg | 180 |
| gccaagaaca | gatggtcccc | agatgcggtc | ccgccctcag | cagtttctag | aaaccatca | 240 |
| gatgtttcca | gggtgcccca | aggacctgaa | atgaccctgt | gccttatttg | aactaaccaa | 300 |
| tcagttcgct | ctcgcttct | gttcgcgcgc | ttctgctccc | cgagctcaat | aaaagagccc | 360 |
| acaacccctc | actcggcgcg | ccagtccttc | gaagtagatc | tttgtcgatc | ctaccatcca | 420 |
| ctcgacacac | ccgccagcgg | ccgctgccaa | gcttccgagc | tctcgaatta | attcacgccg | 480 |
| ccaccatggc | tcttcctgtg | acagctcttc | tgctgcccct | ggccctgctt | ctgcatgctg | 540 |
| ctagacctga | gcaaaagttg | atttctgagg | aagacctcgc | cggcagttta | ttcaaccaag | 600 |
| aagtccaaat | tcccttgacc | gaaagttact | gtggcccatg | tcctaagaac | tggatatgtt | 660 |
| acaaaaataa | ctgttaccaa | ttcttcgatg | aatctaagaa | ttggtatgag | agccaggctt | 720 |
| cttgtatgtc | tcaaaatgcc | agccttctta | agtatacag | caaagaggac | caggatttac | 780 |
| ttaaactggt | gaagtcatat | cattggatgg | gactagtaca | cattccaaca | aatggatctt | 840 |
| ggcagtggga | agacggctcc | attctctcac | ccaacctact | aacaataatt | gaaatgcaga | 900 |
| agggagactg | tgcactctat | gcatcgagct | ttaaaggcta | tagaaaaac | tgttcaactc | 960 |
| caaatacata | tatttgcatg | caaaggactg | tgaccacgac | gccagcgccg | cgaccaccaa | 1020 |
| caccggcgcc | caccatcgcg | tcgcaacccc | tgtccctgag | gcctgaagcg | tgccggccag | 1080 |
| cggcgggcgg | cgcagtgcac | acgagagggc | tggacttcgc | ctgtgatatc | tacatctggg | 1140 |
| cgcccttggc | cgggacttgt | ggggtccttc | tcctgtcact | ggttatcacc | ctttactgca | 1200 |
| aacggggcag | aaagaaactc | ctgtatatat | tcaaacaacc | attatgaga | ccagtacaaa | 1260 |
| ctactcaaga | ggaagatggc | tgtagctgcc | gatttccaga | agaagaagaa | ggaggatgtg | 1320 |
| aaaagaaccg | aaaagcaaaa | gccaagcctg | ttacaagagg | agcaggggca | ggaggccgac | 1380 |
| agagagggca | aacaaagaa | aggccccgc | ccgtcccaaa | cccggattat | gagccaatta | 1440 |
| ggaagggtca | gagagacctg | tattctgggc | tcctgagagt | gaagttcagc | aggagcgcag | 1500 |

```
acgcccccgc gtaccagcaa gggcagaacc agctctataa cgagctcaat ctaggacgaa      1560
gagaggagta cgatgttttg gacaagaggc gtggccggga ccctgagatg ggggaaagc       1620 cgagaaggaa gaaccctcag gaaggcctgt acaatgaact gcagaaagat aagatggcgg      1680
aggcctacag tgagattggg atgaaaggcg agcgccggag gggcaagggg cacgatggcc      1740
tttaccaggg tctcagtaca gccaccaagg acacctacga cgcccttcac atgcaagctc     1800
tgccccctcg ctga                                                       1814
```

<210> SEQ ID NO 74
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Phe Trp Val Leu Val Val Val Gly Gly Val Leu Ala
            180                 185                 190

Cys Tyr Ser Leu Leu Val Thr Val Ala Phe Ile Ile Phe Trp Val Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Lys Asn Arg Lys Ala Lys Ala Lys
                245                 250                 255

Pro Val Thr Arg Gly Ala Gly Ala Gly Gly Arg Gln Arg Gly Gln Asn
            260                 265                 270

Lys Glu Arg Pro Pro Pro Val Pro Asn Pro Asp Tyr Glu Pro Ile Arg
        275                 280                 285

Lys Gly Gln Arg Asp Leu Tyr Ser Gly Leu Leu Arg Val Lys Phe Ser
```

```
                290                 295                 300
Arg Ser Ala Asp Ala Pro Ala Tyr Gln Gln Gly Gln Asn Gln Leu Tyr
305                 310                 315                 320

Asn Glu Leu Asn Leu Gly Arg Arg Glu Glu Tyr Asp Val Leu Asp Lys
                325                 330                 335

Arg Arg Gly Arg Asp Pro Glu Met Gly Gly Lys Pro Arg Lys Asn
                340                 345                 350

Pro Gln Glu Gly Leu Tyr Asn Glu Leu Gln Lys Asp Lys Met Ala Glu
            355                 360                 365

Ala Tyr Ser Glu Ile Gly Met Lys Gly Glu Arg Arg Arg Gly Lys Gly
            370                 375                 380

His Asp Gly Leu Tyr Gln Gly Leu Ser Thr Ala Thr Lys Asp Thr Tyr
385                 390                 395                 400

Asp Ala Leu His Met Gln Ala Leu Pro Pro Arg
                405                 410

<210> SEQ ID NO 75
<211> LENGTH: 1823
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cgcggaatga aagaccccac ctgtaggttt ggcaagctag cttaagtaac gccattttgc      60
aaggcatgga aaatacataa ctgagaatag agaagttcag atcaaggtta ggaacagaga     120
gacagcagaa tatgggccaa acaggatatc tgtggtaagc agttcctgcc ccggctcagg     180
gccaagaaca gatggtcccc agatgcggtc ccgccctcag cagtttctag agaaccatca     240
gatgtttcca gggtgcccca aggacctgaa atgaccctgt gccttatttg aactaaccaa     300
tcagttcgct tctcgcttct gttcgcgcgc ttctgctccc cgagctcaat aaaagagccc     360
acaacccctc actcggcgcg ccagtccttc gaagtagatc tttgtcgatc ctaccatcca     420
ctcgacacac ccgccagcgg ccgctgccaa gcttccgagc tctcgaatta attcacgccg     480
ccaccatggc tcttcctgtg acagctcttc tgctgccccg ggccctgctt ctgcatgctg     540
ctagacctga gcaaaagttg atttctgagg aagacctcgc cggcagttta ttcaaccaag     600
aagtccaaat tcccttgacc gaaagttact gtggcccatg tcctaagaac tggatatgtt     660
acaaaaataa ctgttaccaa ttcttcgatg aatctaagaa ttggtatgag agccaggctt     720
cttgtatgtc tcaaaatgcc agccttctta agtatacag caaagaggac caggatttac     780
ttaaactggt gaagtcatat cattggatgg gactagtaca cattccaaca aatggatctt     840
ggcagtggga agacggctcc attctctcac ccaacctact aacaataatt gaaatgcaga     900
agggagactg tgcactctat gcatcgagct ttaaaggcta tatagaaaac tgttcaactc     960
caaatacata tatttgcatg caaaggactg tgaccacgac gccagcgccg cgaccaccaa    1020
caccggcgcc caccatcgcg tcgcaacccc tgtccctgag gcctgaagcg tgccggccag    1080
cggcgggcgg cgcagtgcac acgagagggc tggacttcgc ctgtgatttt tgggtgctgg    1140
tggtggttgg tggagtcctg gcttgctata gcttgctagt aacagtggcc tttattattt    1200
tctgggtcaa acggggcaga aagaaactcc tgtatatatt caaacaacca tttatgagac    1260
cagtacaaac tactcaagag gaagatggct gtagctgccg atttccagaa gaagaagaag    1320
gaggatgtga aagaaccgaa aagcaaaag ccaagcctgt acaagagga gcaggggcag    1380
```

```
gaggccgaca gagagggcaa aacaaagaaa ggcccccgcc cgtcccaaac ccggattatg    1440
agccaattag gaagggtcag agagacctgt attctgggct cctgagagtg aagttcagca    1500
ggagcgcaga cgcccccgcg taccagcaag ggcagaacca gctctataac gagctcaatc    1560
taggacgaag agaggagtac gatgttttgg acaagaggcg tggccgggac cctgagatgg    1620
ggggaaagcc gagaaggaag aaccctcagg aaggcctgta caatgaactg cagaaagata    1680
agatggcgga ggcctacagt gagattggga tgaaaggcga cgccggagg ggcaaggggc     1740 acgatggcct ttaccagggt ctcagtacag ccaccaagga cacctacgac gcccttcaca    1800
tgcaagctct gccccctcgc tga                                            1823
```

<210> SEQ ID NO 76
<211> LENGTH: 416
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Phe Trp Val Leu Val Val Val Gly Gly Val Leu Ala
            180                 185                 190

Cys Tyr Ser Leu Leu Val Thr Val Ala Phe Ile Ile Phe Trp Val Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Lys Asn Arg Lys Ala Lys Ala Lys
                245                 250                 255

Pro Val Thr Arg Gly Ala Gly Ala Gly Gly Arg Gln Arg Gly Gln Asn
            260                 265                 270
```

```
Lys Glu Arg Pro Pro Val Pro Asn Pro Asp Tyr Glu Pro Ile Arg
            275                 280                 285

Lys Gly Gln Arg Asp Leu Tyr Ser Gly Leu Asn Gln Arg Arg Ile Leu
    290                 295                 300

Arg Val Lys Phe Ser Arg Ser Ala Asp Ala Pro Ala Tyr Gln Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
    370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415

<210> SEQ ID NO 77
<211> LENGTH: 1838
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cgcggaatga aagaccccac ctgtaggttt ggcaagctag cttaagtaac gccattttgc      60
aaggcatgga aaatacataa ctgagaatag agaagttcag atcaaggtta ggaacagaga    120
gacagcagaa tatgggccaa acaggatatc tgtggtaagc agttcctgcc ccggctcagg    180
gccaagaaca gatggtcccc agatgcggtc ccgccctcag cagtttctag aaaccatca    240 gatgtttcca gggtgcccca aggacctgaa atgaccctgt gccttatttg aactaaccaa    300
tcagttcgct tctcgcttct gttcgcgcgc ttctgctccc cgagctcaat aaaagagccc    360 acaaccccctc actcggcgcg ccagtccttc gaagtagatc tttgtcgatc ctaccatcca    420
ctcgacacac ccgccagcgg ccgctgccaa gcttccgagc tctcgaatta attcacgccg    480
ccaccatggc tcttcctgtg acagctcttc tgctgcccct ggccctgctt ctgcatgctg    540
ctagacctga gcaaaagttg atttctgagg aagacctcgc cggcagttta ttcaaccaag    600
aagtccaaat tcccttgacc gaaagttact gtggcccatg tcctaagaac tggatatgtt    660
acaaaaataa ctgttaccaa ttcttcgatg aatctaagaa ttggtatgag gccaggctt    720 cttgtatgtc tcaaaatgcc agccttctta agtatacag caaagaggac caggatttac    780
ttaaactggt gaagtcatat cattggatgg gactagtaca cattccaaca aatgatcttt    840
ggcagtggga agacggctcc attctctcac ccaacctact aacaataatt gaaatgcaga    900
agggagactg tgcactctat gcatcgagct ttaaaggcta tagaaaac tgttcaactc    960 caaatacata tatttgcatg caaggactg tgaccacgac gccagcgccg cgaccaccaa   1020
caccggcgcc caccatcgcg tcgcaacccc tgtccctgag gcctgaagcg tgccggccag   1080
cggcgggcgg cgcagtgcac acgagagggc tggacttcgc ctgtgatttt tgggtgctgg   1140
tggtggttgg tggagtcctg gcttgctata gcttgctagt aacagtggcc tttattattt   1200
tctgggtcaa acggggcaga aagaaactcc tgtatatatt caaacaacca tttatgagac   1260
```

```
cagtacaaac tactcaagag gaagatggct gtagctgccg atttccagaa gaagaagaag   1320
gaggatgtga aaagaaccgc aaagcaaagg caaaacccgt cacacgagga gcgggcgcag   1380
ggggacgaca acgcggtcag aataaggaac gcccgcctcc agtaccaaat ccagattatg   1440
aaccaattcg aagggacaa cgcgatctct actccggtct caatcagagg cgaattctga    1500
gagtgaagtt cagcaggagc gcagacgccc ccgcgtacca gcaagggcag aaccagctct   1560
ataacgagct caatctagga cgaagagagg agtacgatgt tttggacaag aggcgtggcc   1620
gggaccctga gatgggggga aagccgagaa ggaagaaccc tcaggaaggc ctgtacaatg   1680
aactgcagaa agataagatg gcggaggcct acagtgagat tgggatgaaa ggcgagcgcc   1740
ggaggggcaa ggggcacgat ggcctttacc agggtctcag tacagccacc aaggacacct   1800
acgacgccct tcacatgcaa gctctgcccc ctcgctga                           1838
```

<210> SEQ ID NO 78  
<211> LENGTH: 50  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<221> NAME/KEY: SITE  
<222> LOCATION: (1)..(5)  
<223> OTHER INFORMATION: This region may encompass 1-5 residues  
<220> FEATURE:  
<221> NAME/KEY: SITE  
<222> LOCATION: (6)..(10)  
<223> OTHER INFORMATION: This region may encompass 1-5 residues  
<220> FEATURE:  
<221> NAME/KEY: SITE  
<222> LOCATION: (11)..(15)  
<223> OTHER INFORMATION: This region may encompass 1-5 residues  
<220> FEATURE:  
<221> NAME/KEY: SITE  
<222> LOCATION: (16)..(20)  
<223> OTHER INFORMATION: This region may encompass 1-5 residues  
<220> FEATURE:  
<221> NAME/KEY: SITE  
<222> LOCATION: (21)..(25)  
<223> OTHER INFORMATION: This region may encompass 1-5 residues  
<220> FEATURE:  
<221> NAME/KEY: SITE  
<222> LOCATION: (26)..(30)  
<223> OTHER INFORMATION: This region may encompass 1-5 residues  
<220> FEATURE:  
<221> NAME/KEY: SITE  
<222> LOCATION: (31)..(35)  
<223> OTHER INFORMATION: This region may encompass 1-5 residues  
<220> FEATURE:  
<221> NAME/KEY: SITE  
<222> LOCATION: (36)..(40)  
<223> OTHER INFORMATION: This region may encompass 1-5 residues  
<220> FEATURE:  
<221> NAME/KEY: SITE  
<222> LOCATION: (41)..(45)  
<223> OTHER INFORMATION: This region may encompass 1-5 residues  
<220> FEATURE:  
<221> NAME/KEY: SITE  
<222> LOCATION: (46)..(50)  
<223> OTHER INFORMATION: This region may encompass 1-5 residues  
<220> FEATURE:  
<221> NAME/KEY: SITE  
<222> LOCATION: (1)..(50)  
<223> OTHER INFORMATION: This sequence may encompass 1-5 "(G)n(S)n" repeating units wherein n = 1-5

<400> SEQUENCE: 78

Gly Gly Gly Gly Gly Ser Ser Ser Ser Ser Gly Gly Gly Gly Gly Ser  
1               5                   10                  15

-continued

```
Ser Ser Ser Ser Gly Gly Gly Gly Ser Ser Ser Ser Ser Gly Gly
            20              25              30
Gly Gly Gly Ser Ser Ser Ser Ser Gly Gly Gly Gly Ser Ser Ser
        35              40              45
Ser Ser
    50
```